United States Patent
Becker et al.

(10) Patent No.: US 11,180,518 B2
(45) Date of Patent: Nov. 23, 2021

(54) PHENYL-HETEROCYCLE-PHENYL DERIVATIVES FOR USE IN THE TREATMENT OR PREVENTION OF MELANOMA

(71) Applicants: MAX-PLANCK-GESELLSCHAFT ZUR FÖRDERUNG DER WISSENSCHAFTEN E.V., Munich (DE); LUDWIG-MAXIMILIANS-UNIVERSITÄT MÜNCHEN, Munich (DE)

(72) Inventors: Dorothea Becker, Göttingen (DE); Thomas M. Jovin, Göttingen (DE); Christian Griesinger, Göttingen (DE); Andrei Leonov, Göttingen (DE); Sergey Ryazanov, Göttingen (DE); Armin Giese, Munich (DE); Tiago F. Outeiro, Göttingen (DE); Diana F. Lazaro, Göttingen (DE); Michael P. Schön, Bovenden (DE); Margarete Schön, Bovenden (DE)

(73) Assignees: MAX-PLANCK-GESELLSCHAFT ZUR FÖRDERUNG DER WISSENSCHAFTEN E.V., Munich (DE); LUDWIG-MAXIMILIANS-UNIVERSITÄT MÜNCHEN, Munich (DE)

(*) Notice: Subject to any disclaimer, the term of this patent is extended or adjusted under 35 U.S.C. 154(b) by 0 days.

(21) Appl. No.: 16/612,717

(22) PCT Filed: May 11, 2018

(86) PCT No.: PCT/EP2018/062236
§ 371 (c)(1),
(2) Date: Nov. 11, 2019

(87) PCT Pub. No.: WO2018/206778
PCT Pub. Date: Nov. 15, 2018

(65) Prior Publication Data
US 2020/0165279 A1    May 28, 2020

(30) Foreign Application Priority Data
May 12, 2017 (EP) .................................... 17170855

(51) Int. Cl.
| | | |
|---|---|---|
| *C07F 9/6503* | (2006.01) |
| *A61P 35/00* | (2006.01) |
| *C07D 231/12* | (2006.01) |
| *C07D 261/08* | (2006.01) |
| *C07D 271/06* | (2006.01) |
| *C07D 403/10* | (2006.01) |
| *C07D 405/10* | (2006.01) |
| *C07D 413/10* | (2006.01) |
| *A61K 31/675* | (2006.01) |
| *A61K 31/4155* | (2006.01) |
| *A61K 31/415* | (2006.01) |

(52) U.S. Cl.
CPC .......... *C07F 9/65031* (2013.01); *A61P 35/00* (2018.01); *C07D 231/12* (2013.01); *C07D 261/08* (2013.01); *C07D 271/06* (2013.01); *C07D 403/10* (2013.01); *C07D 405/10* (2013.01); *C07D 413/10* (2013.01); *A61K 31/415* (2013.01); *A61K 31/4155* (2013.01); *A61K 31/675* (2013.01)

(58) Field of Classification Search
CPC .............. A61K 31/675; A61K 31/4155; A61K 31/415; A61P 35/00
See application file for complete search history.

(56) References Cited

U.S. PATENT DOCUMENTS

| | | | |
|---|---|---|---|
| 3,773,919 A | 11/1973 | Boswell et al. |
| 4,485,045 A | 11/1984 | Rogen |
| 4,544,545 A | 10/1985 | Ryan et al. |
| 8,101,641 B2* | 1/2012 | Almstead ................ A61P 35/00 |
| | | | 514/364 |
| 10,435,373 B2* | 10/2019 | Giese ...................... A61P 21/02 |

FOREIGN PATENT DOCUMENTS

| | | | |
|---|---|---|---|
| EP | 0 036 676 B2 | 9/1981 |
| EP | 0 052 322 A2 | 5/1982 |
| EP | 0 058 481 B2 | 8/1982 |
| EP | 0 088 046 A2 | 9/1983 |

(Continued)

OTHER PUBLICATIONS

Liu et al., "Synthesis, biological evaluation of novel 4,5-dihydro-2H-pyrazole 2-hydroxyphenyl derivatives as BRAF inhibitors", Bioorganic & Medicinal Chemistry, vol. 20, No. 20, pp. 6089-6096 (2012).*

(Continued)

*Primary Examiner* — Kevin E Weddington
(74) *Attorney, Agent, or Firm* — Foley & Lardner LLP

(57) ABSTRACT

The present invention relates to a compound represented by the formula (E) which is useful for treating or preventing melanoma.

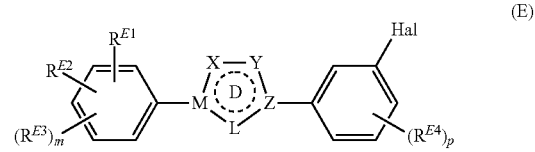

9 Claims, 18 Drawing Sheets

(56) References Cited

FOREIGN PATENT DOCUMENTS

| | | |
|---|---|---|
| EP | 0 102 324 A2 | 3/1984 |
| EP | 0 133 988 A2 | 3/1985 |
| EP | 0 142 641 A2 | 5/1985 |
| EP | 0 143 949 B1 | 6/1985 |
| EP | 2 133 355 A1 | 12/2009 |
| EP | 3 181 572 A1 | 6/2017 |
| WO | WO-98/17652 A1 | 4/1998 |
| WO | WO-2004/052280 A2 | 6/2004 |
| WO | WO-2004/072050 A1 | 8/2004 |
| WO | WO-2004/080972 A1 | 9/2004 |
| WO | WO-2008/131148 A1 | 10/2008 |
| WO | WO-2010/000372 A2 | 1/2010 |
| WO | WO-2017046737 A1 * 3/2017 ............... A61P 9/06 |

OTHER PUBLICATIONS

Baykov et al., "The first one-pot ambient-temperature synthesis of 1,2,4-oxadiazoles from amidoximes and carboxylic acid esters", Tetrahedron, 2017, pp. 945-951, vol. 73, Elsevier Ltd.

Becker et al., "Proliferation of human malignant melanomas is inhibited by antisense oligodeoxynucleotides targeted against basic fibroblast growth factor", The EMBO Journal, 1989, pp. 3685-3691, vol. 8, No. 12, IRL Press.

Besselièvre et al., "Ligandless Microwave-Assisted Pd/Cu-Catalyzed Direct Arylation of Oxazoles", Journal of Organic Chemistry, 2008, pp. 3278-3280, vol. 73, No. 8, American Chemical Society.

Chen et al., "DJ-1: a promising marker in metastatic uveal melanoma", Journal of Cancer Research and Clinical Oncology, 2015, pp. 315-321, vol. 141, Springer-Verlag Berlin Heidelberg 2014.

Choong et al., "Knockdown of α-Synuclein Enhances Susceptibility to Staurosporine-Induced Apoptosis in Human SK-MEL28 Cells", Journal of Biological Sciences, 2011, pp. 135-145, vol. 11, No. 2, Asian Network for Scientific Information.

Ellis et al., "Prognostic Impact of p62 Expression in Cutaneous Malignant Melanoma", Journal of Investigative Dermatology, 2014, pp. 1476-1478, vol. 134.

Eppstein et al., "Biological activity of liposome-encapsulated murine interferon is mediated by a cell membrane receptor", Proceedings of the National Academy of Sciences of the United States of America, Jun. 1985, pp. 3688-3692, vol. 82.

Extended European Search Report issued in European Application No. 17170855.5 dated Nov. 24, 2017, 10 pages.

Galluzzi et al., "Autophagy in malignant transformation and cancer progression", The EMBO Journal, 2015, pp. 856-880, vol. 34, No. 7, The Authors.

Goodall et al., "Development of potent autophagy inhibitors that sensitize oncogenic BRAF V600E mutant melanoma tumor cells to vemurafenib", Autophagy, Jun. 2014, pp. 1120-1136, vol. 10, Issue 6, Landes Bioscience.

Hansen et al., "α-Synuclein propagates from mouse brain to grafted dopaminergic neurons and seeds aggregation in cultured human cells", The Journal of Clinical Investigation, Feb. 2011, pp. 715-725, vol. 121, No. 2.

Hintsala et al., "Dysregulation of redox-state-regulating enzymes in melanocytic skin tumours and the surrounding microenvironment", Histopathology, 2015, pp. 348-357, vol. 67, John Wiley & Sons Ltd.

Hwang et al., "Hepatic uptake and degradation of unilamellar sphingomyelin/cholesterol liposomes: A kinetic study", Proceedings of the National Academy of Sciences of the United States of America, Jul. 1980, pp. 4030-4034, vol. 77, No. 7.

International Search Report and Written Opinion of the International Searching Authority, issued in International Application No. PCT/EP2018/062236 dated Jun. 26, 2018.

Israeli et al., "α-Synuclein Expression Selectively Affects Tumorigenesis in Mice Modeling Parkinson's Disease", PLoS one, May 2011, pp. 1-9, vol. 6, Issue 5, e19622.

Kroemer et al., "Autophagic cell death: the story of a misnomer", Nature Reviews | Molecular Cell Biology, (Advance Online Publication) 2008, pp. 1-7, vol. 9, Macmillan Publishers Limited.

Langer et al., "Biocompatibility of polymeric delivery systems for macromolecules", Journal of Biomedical Materials Research, 1981, pp. 267-277, vol. 15, John Wiley & Sons, Inc.

Langer et al., "Controlled Release of Macromolecules: Biological Studies", Journal of Controlled Release, 1985, pp. 331-341, vol. 2, Elsevier Science Publishers B.V., Amsterdam.

Langer, "Controlled release of macromolecules", Chemtech, 1982, pp. 98-105, vol. 12.

Lee et al., "Design, Synthesis, and Biological Evaluations of 2,5-Diaryl-2,3-dihydro-1,3,4-oxadiazoline Analogs of Combretastatin-A4", Journal of Medicinal Chemistry, 2010, pp. 325-334, vol. 53, No. 1, American Chemical Society.

Lee et al., "Facile Synthesis of Oxazoles Starting from Ketones", Synthetic Communications, 2003, pp. 1611-1614, vol. 33, No. 9, Marcel Dekker, Inc., New York, NY.

Lee et al., "Role of Ser129 phosphorylation of α-synuclein in melanoma cells", Journal of Cell Science, 2012, pp. 696-704, vol. 126, No. 2, The Company of Biologists Ltd.

Levin et al., "The oligomer modulator anle138b inhibits disease progression in a Parkinson mouse model even with treatment started after disease onset", Acta Neuropathologica, 2014, pp. 779-780, vol. 127, Springer.

Lopes Da Fonseca et al., "ATP13A2 and Alpha-synuclein: a Metal Taste in Autophagy", Experimental Neurobiology, Dec. 2014, pp. 314-323, vol. 23, No. 4.

Ma et al., "Targeting ER stress-induced autophagy overcomes BRAF inhibitor resistance in melanoma", The Journal of Clinical Investigation, Mar. 2014, pp. 1406-1417, vol. 124, No. 3.

Maddodi et al., "Induction of Autophagy and Inhibition of Melanoma Growth In Vitro and In Vivo by Hyperactivation of Oncogenic BRAF", Journal of Investigative Dermatology, 2010, pp. 1657-1667, vol. 130, The Society for Investigative Dermatology.

Maes et al., "Autophagy and mitophagy interplay in melanoma progression", Mitochondrion, 2014, pp. 58-68, vol. 19, Elsevier B.V. and Mitochondria Research Society.

Margolin, "The Promise of Molecularly Targeted and Immunotherapy for Advanced Melanoma", Current Treatment Options in Oncology, 2016, pp. 1-14, vol. 17, No. 48, Springer Science Business Media New York.

Matsuo et al., "Parkinson's Disease-Related Protein, α-Synuclein, in Malignant Melanoma", PLoS ONE, May 2010, pp. 1-8, vol. 5, Issue 5, e10481.

Miracco et al., "Beclin 1 and LC3 autophagic gene expression in cutaneous melanocytic lesions", Human Pathology, 2010, pp. 503-512, vol. 41, Elsevier Inc.

Müller, "Prodrug Approaches for Enhancing the Bioavailability of Drugs with Low Solubility", Chemistry & Biodiversity, 2009, pp. 2071-2083, vol. 6, Verlag Helvetica Chimica Acta AG, Zurich.

Ono et al., "Development of novel β-amyloid probes based on 3,5-diphenyl-1,2,4-oxadiazole", Bioorganic & Medicinal Chemistry, 2008, pp. 6867-6872, vol. 16, Elsevier Ltd.

Pardo et al., "The characterization of the invasion phenotype of uveal melanoma tumour cells shows the presence of MUC18 and HMG-1 metastasis markers and leads to the identification of DJ-1 as a potential serum biomarker", International Journal of Cancer, 2006, pp. 1014-1022, vol. 119, Wiley-Liss, Inc.

Prieto et al., "Targeted Therapies Combined With Immune Checkpoint Therapy", The Cancer Journal, Mar./Apr. 2016, pp. 138-146, vol. 22, No. 2, Wolters Kluwer Health, Inc.

Rao et al., "Synthesis and Studies on Some New Fluorine Containing Hydroxypyrazolines and 1H Pyrazoles-as Possible Antiproliferative Agents", Journal of Pharmacology and Toxicology, 2008, pp. 102-110, vol. 3, No. 2, Academic Journals Inc.

Sidman et al., "Controlled Release of Macromolecules and Pharmaceuticals from Synthetic Polypeptides Based on Glutamic Acid", Biopolymers, 1983, pp. 547-556, vol. 22, John Wiley & Sons, Inc.

Smith et al., "Whole-genome expression profiling of the melanoma progression pathway reveals marked molecular differences between

(56) References Cited

OTHER PUBLICATIONS nevi/melanoma in situ and advanced-stage melanomas", Cancer Biology & Therapy, Sep. 2005, pp. 1018-1029, vol. 4, No. 9, Landes Bioscience.

Turriani et al., "Treatment with diphenyl-pyrazole compound anle138b/c reveals that α-synuclein protects melanoma cells from autophagic cell death", Proceedings of the National Academy of Sciences of the United States of America, 2017, pp. E4971-E4977, vol. 114, No. 25.

Wagner et al., "Anle138b: a novel oligomer modulator for disease-modifying therapy of neurodegenerative diseases such as prion and Parkinson's disease", Acta Neuropathologica, 2013, pp. 795-813, vol. 125, Springer.

Wagner et al., "Reducing tau aggregates with anle138b delays disease progression in a mouse model of tauopathies", Acta Neuropathologica, 2015, pp. 619-631, vol. 130, Springer.

Watson-Hurst et al., "The role of N-Cadherin, MCAM, and $\beta_3$ integrin in melanoma progression, proliferation, migration and invasion", Cancer Biology & Therapy, Oct. 2006, pp. 1375-1382, vol. 5, Issue 10, Landes Bioscience.

Welinder et al., "Analysis of Alpha-Synuclein in Malignant Melanoma-Development of a SRM Quantification Assay", PLoS ONE, Oct. 2014, pp. 1-9, vol. 9, Issue 10, e110804.

White, "Deconvoluting the context-dependent role for autophagy in cancer", Nature Reviews | Cancer, Jun. 2012, pp. 401-410, vol. 12, Macmillan Publishers Limited.

White, "The role for autophagy in cancer", The Journal of Clinical Investigation, Jan. 2015, pp. 42-46, vol. 125, No. 1.

Xie et al., "Atg7 Overcomes Senescence and Promotes Growth of $Braf^{600E}$-Driven Melanoma", Cancer Discovery, Apr. 2015, pp. 411-423, vol. 5, American Association for Cancer Research.

Yang et al., "Design, biological evaluation and 3D QSAR studies of novel dioxin-containing triaryl pyrazoline derivatives as potential B-Raf inhibitors", Bioorganic & Medicinal Chemistry, 2016, pp. 3052-3061, vol. 24, No. 13, Elsevier Ltd.

Yoshizumi et al., "Synthesis of 2,5-diaryloxazoles through van Leusen reaction and copper-mediated direct arylation", Tetrahedron Letters, 2009, pp. 3273-3276, vol. 50, Elsevier Ltd.

\* cited by examiner

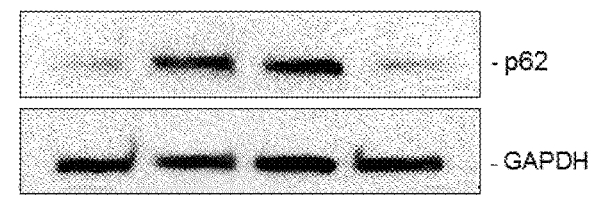

WM983-A

WM983-B

SK-MEL-5

WM1158

PHENYL-HETEROCYCLE-PHENYL DERIVATIVES FOR USE IN THE TREATMENT OR PREVENTION OF MELANOMA

RELATED APPLICATIONS

The present application claims priority under 37 U.S.C. § 371 to International Patent Application No. PCT/EP2018/062236, filed May 11, 2018, which claims priority to and the benefit of European Patent Application No. 17170855.5, filed on May 12, 2017. The contents of these applications are hereby incorporated by reference in their entireties.

SUMMARY OF THE INVENTION

The present invention relates to a compound represented by formula (E) for use in the treatment or prevention of melanoma.

Several documents are cited throughout the text of this specification. The disclosure content of the documents cited herein (including any manufacturer's specifications, instructions, etc.) is herewith incorporated by reference.

BACKGROUND OF THE INVENTION

Melanoma is the most aggressive type of skin cancer. The risk of developing of melanoma has more than quadrupled over the past 25 years, and the worldwide incidence of melanoma continues to rise at an alarming rate. Melanoma also accounts for 75% of all skin cancer-related deaths, and in women aged 25 to 29, it is now the prevalent cancer second only to breast cancer in women aged 30 to 34. The American Cancer Society estimates that in the US alone, approximately 91,270 new melanomas will be diagnosed in 2018, and about 9,320 people will die from melanoma. In the majority of melanoma patients, the disease has a sporadic onset and in approximately 10% of all cases, it is inherited. Furthermore, individuals with certain risk factors, such as skin that burns easily during exposure to sun light are more likely than others to develop melanoma.

The stages defining melanoma progression are: atypical nevi (AN)>melanoma in situ (MIS), the first stage of melanoma development, which is noninvasive>melanoma in the radial growth phase (RGP melanoma), which has penetrated through the basal layer into the dermis and as such represents the first stage of invasive melanoma>primary melanoma in the vertical growth phase (VGP melanoma), which has invaded deep into the dermis and beyond>metastatic melanoma (MGP melanoma), which has spread to lymph nodes, distant organs, and not infrequently the brain. The clinical prognosis for patients with melanoma is directly related to the size and depth of invasion of the melanoma at the time of diagnosis. However, the prognosis is grave once melanoma metastasizes because chemotherapy and/or radiation treatment do not affect the course of advanced melanoma. Hence, there is a need to identify novel compounds for the treatment and prevention of melanoma, and a durable response rate to immune checkpoint inhibitor therapy is still not seen in more than 40% of melanoma patients treated. Hence, there is a continuing need to identify novel compounds for the treatment and prevention of melanoma.

In WO2010/00372, compounds were disclosed, which have been shown to be effective in inhibiting aggregation of proteins. A broad screen was based on a combination of scanning for intensely fluorescent targets (SIFT) and cellular assays measuring the amount of aggregation of α-synuclein (PD) and prion protein (CJD). In this screen certain compounds including 3,5-diphenyl pyrazole (DPP) compounds turned out to be a highly active scaffold that could be easily modified by organic synthesis. An array of around 250 compounds in this class was synthesized and the compounds were assessed for oral availability and efficacy in animal models mimicking the various mentioned diseases (AD, CJD, PD). The compound termed "anle138b" having the following structure:

5-(3-Bromophenyl)-3-(3,4-methylenedioxyphenyl)-1H-pyrazole has been identified as being efficacious in modulating the oligomer formation in animal models mimicking Parkinson's disease (PD) as well as Creutzfeldt-Jakob's disease (CJD) (J. Wagner et al., Acta Neuropathol. 125, 795-813 (2013); J. Levin et al., Act. Neuropath. 127, 779-780 (2014)) and Alzheimer's disease (AD) (J. Wagner, et al., Act. Neuropath. 130, 619-631 (2015) (doi: 10.1007/s0041-015-1483-3)).

EP15199972.9 discloses derivatives of the compounds according to WO2010/00372 that have improved water solubility.

α-Synuclein is an intrinsically disordered protein whose physiological function remains unclear. However, when it aggregates, it forms toxic oligomers and eventually fibrils, which form Lewy bodies that are a hallmark of Parkinson's disease (PD). The formation of toxic oligomers is likely the reason for neuronal dysfunction and, eventually, neuronal death. By removing α-synuclein toxic oligomers, anle138b and related DPP compounds rescue dopaminergic neurons from the adverse effects of α-synuclein aggregation. As explained in Examples 1 and 2, the high-level expression of α-synuclein ensures the survival of melanoma cells, which is the exact opposite of the effect that α-synuclein has on dopaminergic neurons. Since anle138b and related DPP compounds are beneficial to the function and survival of dopaminergic neurons, they likewise are expected to benefit the function and survival of melanoma cells. As explained in Example 3, the effect of anle138b and related DPP compounds on melanoma cells turns out to be the exact opposite. This was completely unforeseeable and unpredictable, even to experts in the fields of cancer and neurodegeneration.

A. Images of select normal skin, nevus, and VGP and MGP melanoma TMA cores probed with an anti-α-synuclein antibody and counterstained with hematoxylin. Bar graph: Expression of the SNCA gene, determined via previously conducted whole-genome expression profiling, in normal skin (NS), benign nevi (BN), atypical nevi (AN), melanoma in situ (MIS), VGP melanoma, and MGP melanoma.

B. Select images of a nevus, a VGP melanoma, and an MGP melanoma (subcutaneous metastasis) probed with an antibody to LRRK2 and counterstained with hematoxylin. Bar graph: Expression of the PARK8 (LRRK2) gene, determined via previously conducted whole-genome expression profiling, in normal skin (NS), benign nevi (BN), atypical nevi (AN), melanoma in situ (MIS), VGP melanoma, and MGP melanoma.

C. Select images of a nevus, a VGP melanoma, and an MGP melanoma (subcutaneous metastasis) probed with an anti-Parkin antibody and counterstained with hematoxylin. Bar graph: Expression of the PARK2 gene, determined via previously conducted whole-genome expression profiling, in normal skin (NS), benign nevi (BN), atypical nevi (AN), melanoma in situ (MIS), VGP melanoma, and MGP melanoma.

Figure 2:
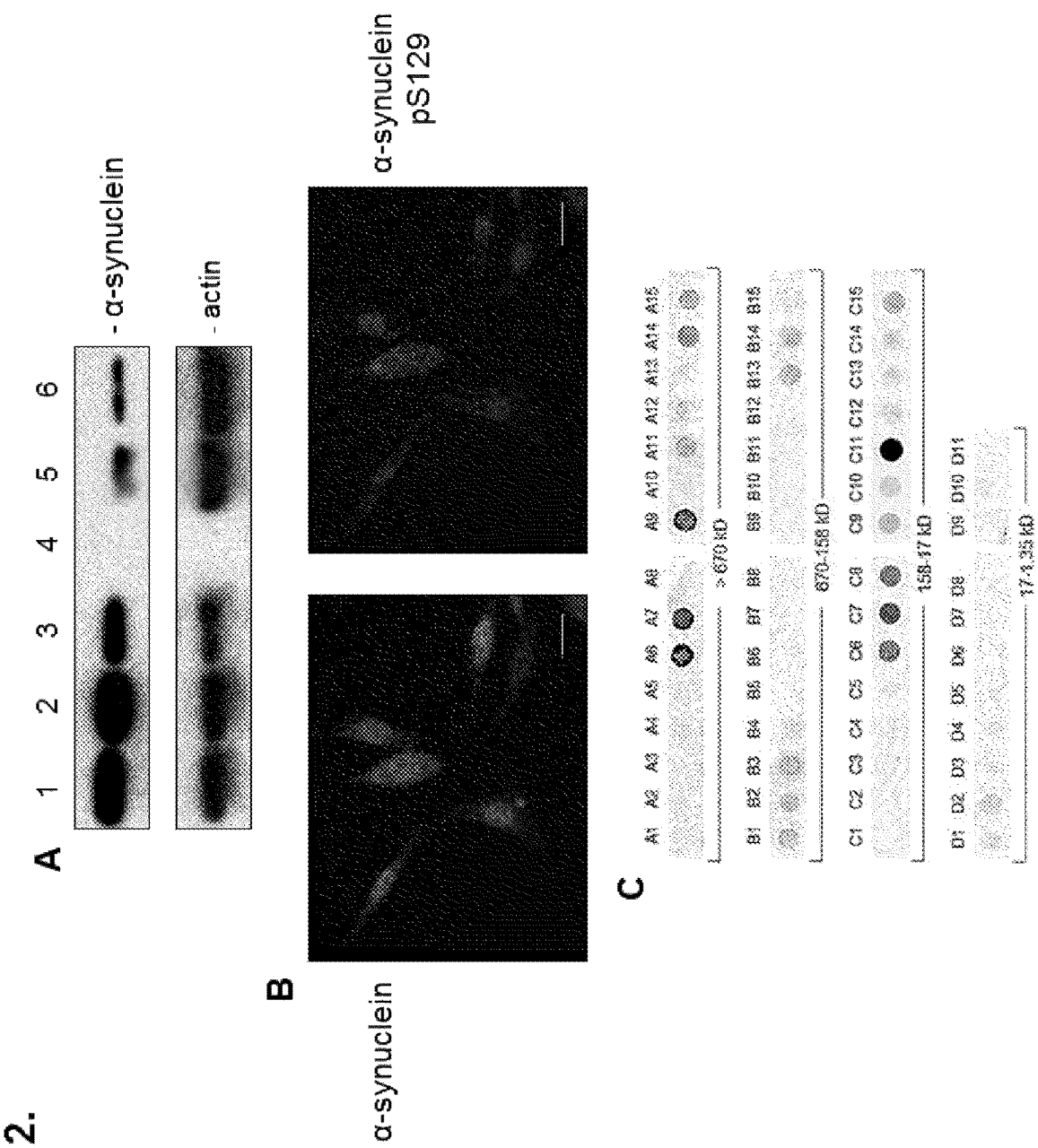

FIG. 2. Expression and presence of monomeric as well as oligomeric species of α-synuclein protein in melanoma cells.

A. Immunoblot analysis of α-synuclein expression in the VGP melanoma cell line WM983-A (lane 1), in the MGP melanoma cell lines WM983-B (lane 2), SK-MEL-5 (lane 3), WM852 (lane 4), and in the RGP/VGP melanoma cell line WM1158 (lane 5). 10 μg each of whole-cell lysate were loaded in lanes in 1, 2, and 3. To clearly visualize expression of α-synuclein protein in the low-level α-synuclein-expressing melanoma cell lines, WM852 and WM1158, 20 μg each of whole-cell lysate were loaded in lanes 5 and 6 (lane 4 was left blank). Probing with an anti-actin antibody served as loading control.

B. Immunofluorescence analysis of α-synuclein expression in WM983-B melanoma cells probed with antibody to α-synuclein or phosphorylated α-synuclein (pSer129).

C. Presence of monomeric as well as α-synuclein oligomeric species in WM983-B melanoma cells detected by SEC—filter trap assay. Collected fractions (A1>A15, B1>B15, C1>C15, D1>D11), applied to nitrocellulose membrane, were probed with an anti-α-synuclein antibody.

Figure 3:
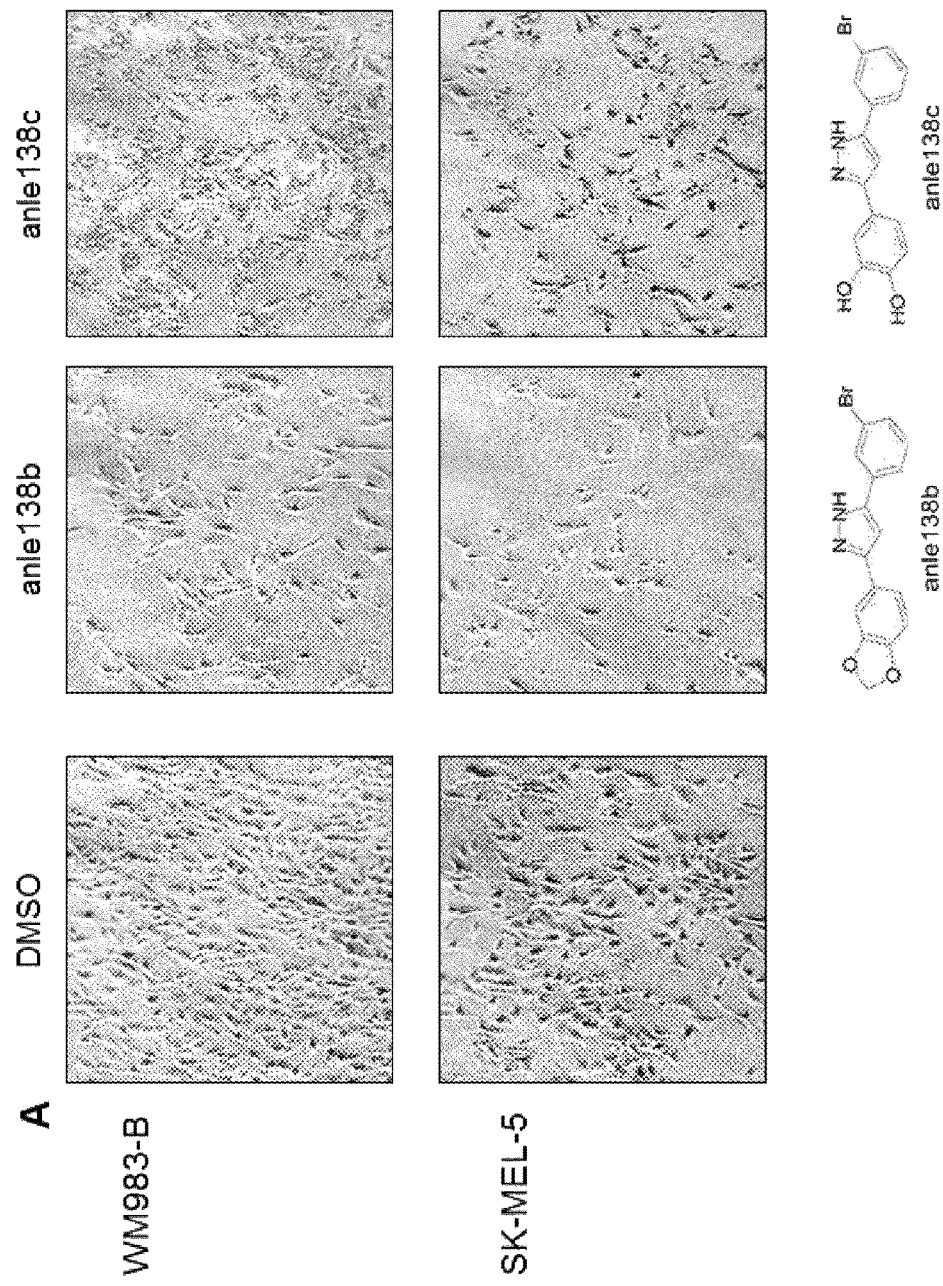
Figure 3:
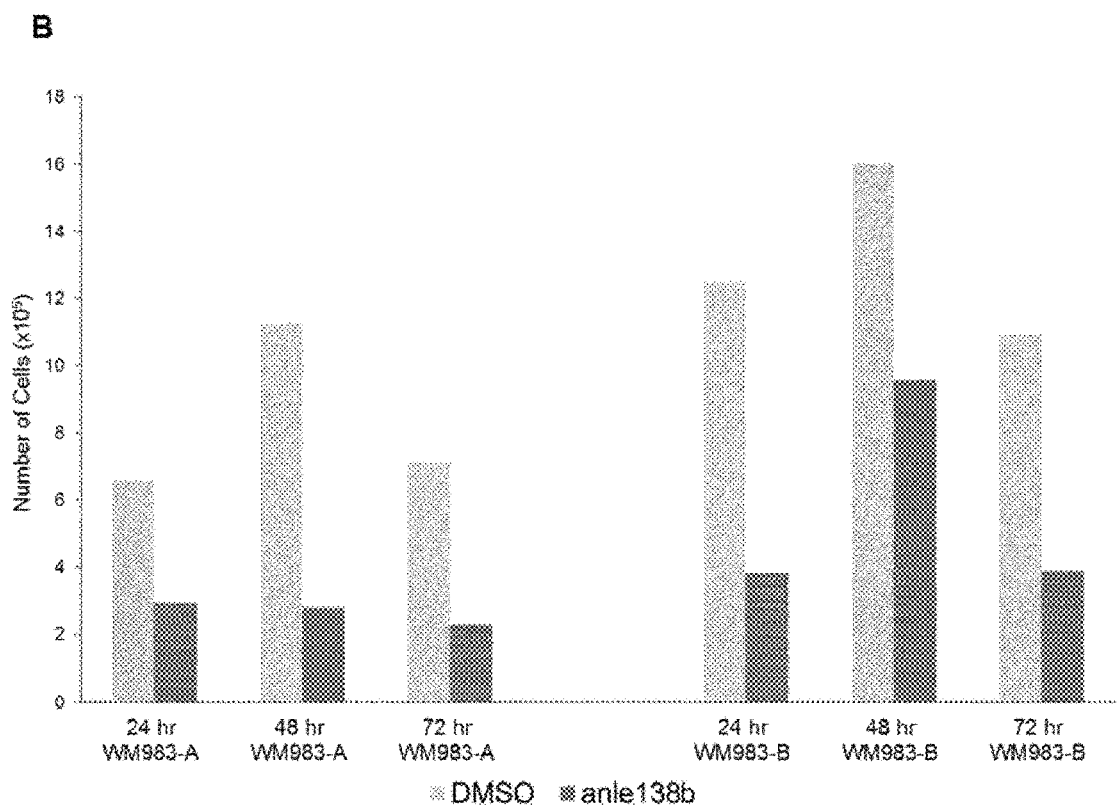

FIG. 3. Treatment of melanoma cells with the α-synuclein oligomer modulators, anle138b or anle138c, changes the cells' morphology and inhibits their proliferation.

A. Phase-contrast images, captured at 10× magnification, showing the morphology of WM983-B and SK-MEL-5 melanoma cells that for 48 hr had received DMSO only, or were treated for 48 hr with a single dose (10 μM) of anle138b or anle138c.

B. Proliferation of WM983-A and WM983-B melanoma cells that had received DMSO only, or were treated with 10 μM of anle138b for 24, 48 or 72 hr, with replenishment of 10 μM of the compound at 48 hr. Shown for each time point and cell line is the mean of triplicate samples analyzed (n=1).

Figure 4:
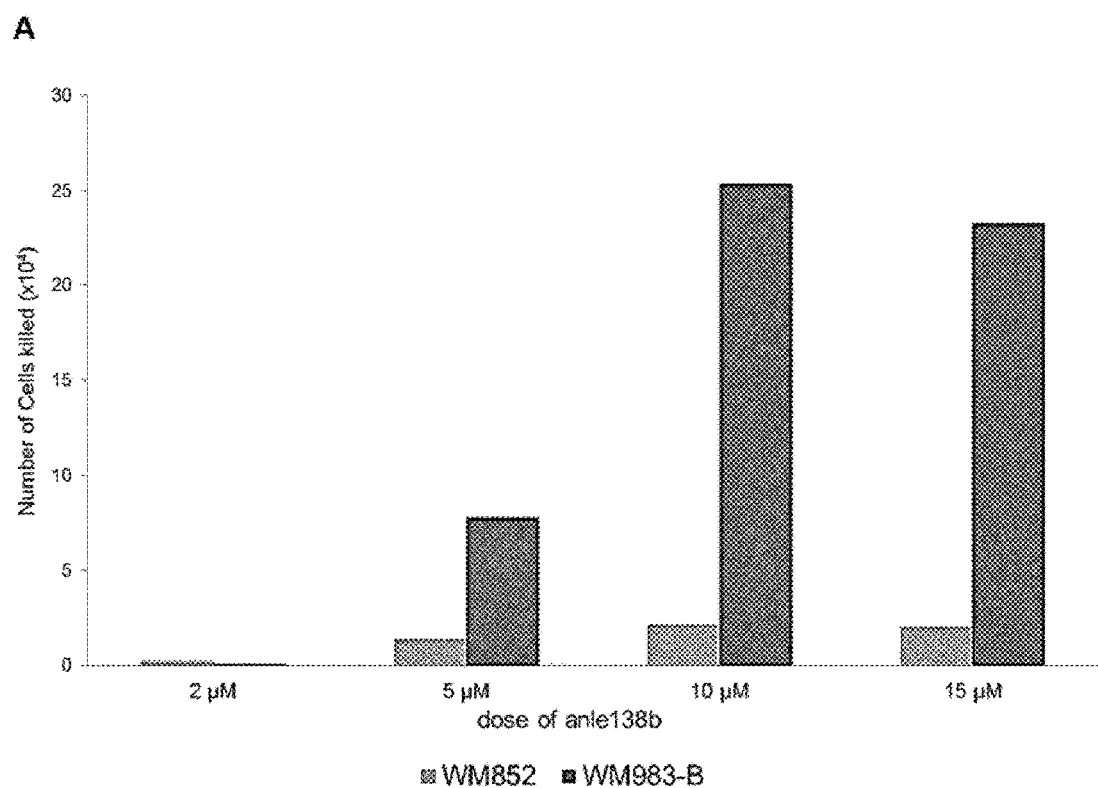
Figure 4:
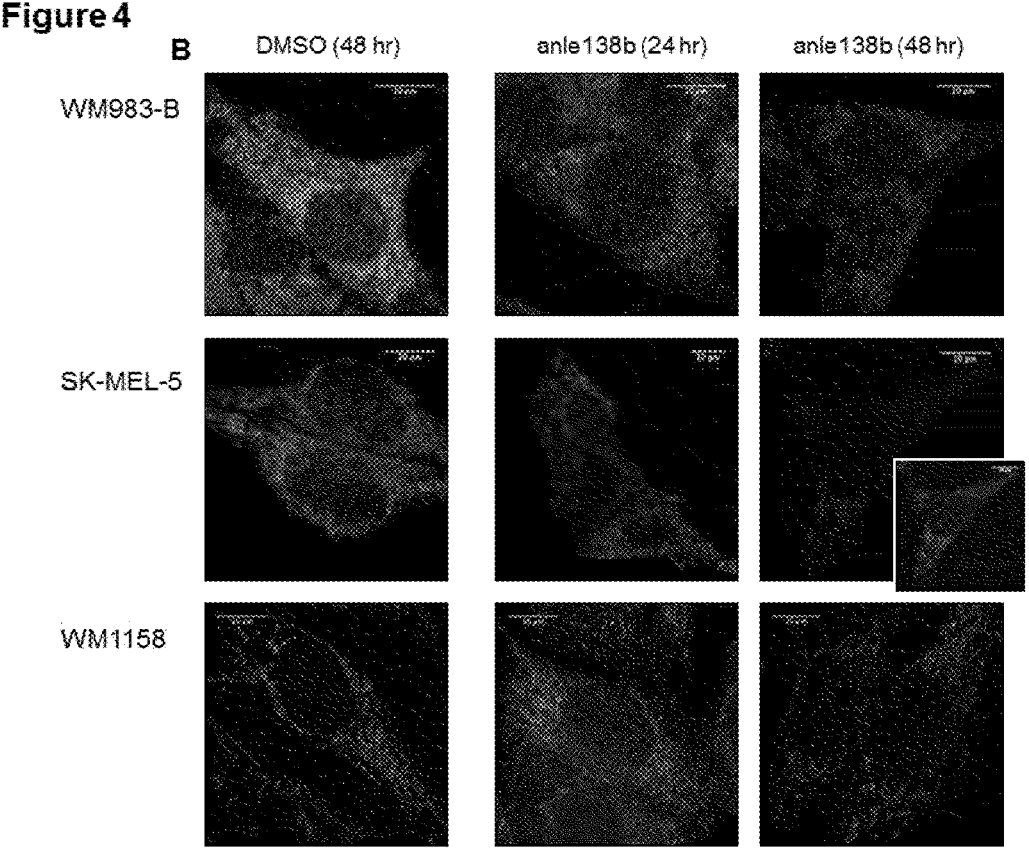
Figure 4:
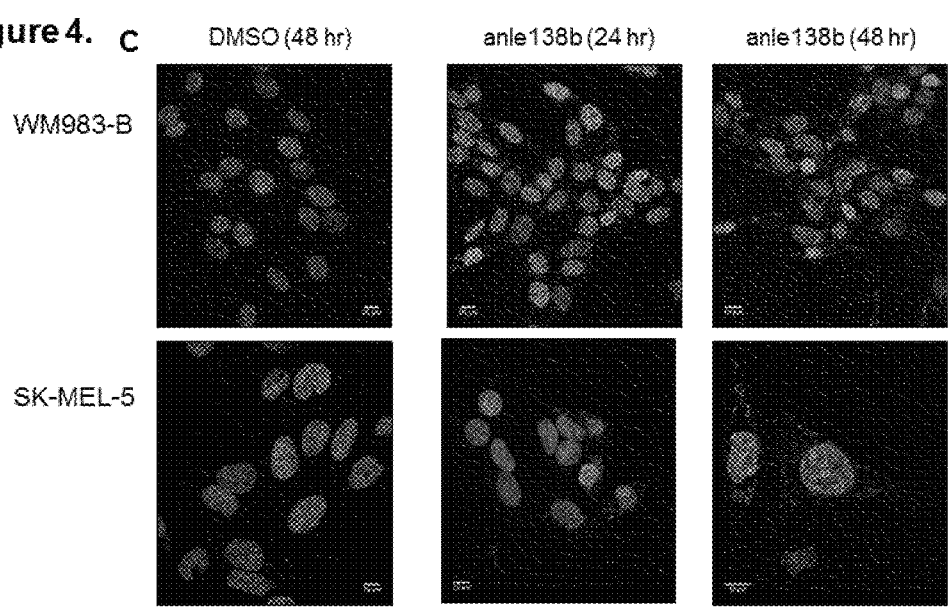

FIG. 4. Treatment of melanoma cells with the α-synuclein oligomer modulator, anle138b, leads to melanoma cell killing due to plasma membrane damage, mitochondrial dysfunction, and dysregulation of melanoma cell autophagy.

A. LDH release-based quantitation of anle138b treatment-induced cell killing of WM852 and WM983-B melanoma cells that were treated with 2, 5, 10 or 15 μM of the oligomer modulator for 96 hr, with replenishment of each equivalent dose at 48 hr. Shown for each dose and cell line is the mean of four replicates analyzed (n=1).

B. Maximum intensity projections of confocal image stacks of MitoTracker dye-stained WM983-B, SK-MEL-5, and WM1158 melanoma cells that for 48 hr had received DMSO only, or were treated for 24 or 48 hr with a single dose (10 μM) of anle138b. The inset in the image of SK-MEL-5 melanoma cells, treated for 48 hr with anle138b, was captured at 5× higher laser power to make the fluorescence visible.

C. Confocal immunofluorescence image analysis of LC3 expression in WM983-B and SK-MEL-5 melanoma cells that for 48 hr had received DMSO only, or were treated with a single dose (10 μM) of anle138b for 24 or 48 hr. The anti-LC3B antibody-probed melanoma cells were counterstained with fluorescent DRAQ5.

D. Immunoblot analysis of p62/SQSTM1 expression in WM983-B melanoma cells that were treated with anle138b (7.5 μM) for 24 (lane 1), 48 (lane 2) or 72 hr (lane 3), with replenishment of an equivalent dose at 48 hr. WM983-B melanoma cells that for 72 hr, with replenishment at 48 hr, had received DMSO only (lane 4), served as the control. The immunoblot was probed with an anti-GAPDH antibody for loading control.

Figure 5:
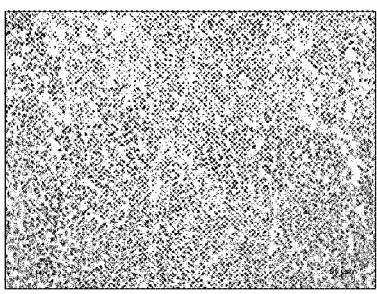
Figure 5:
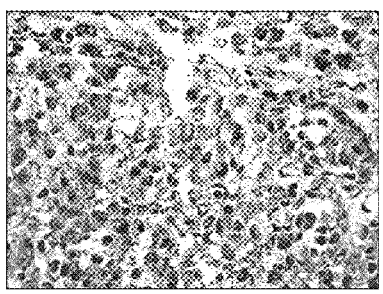
Figure 5:
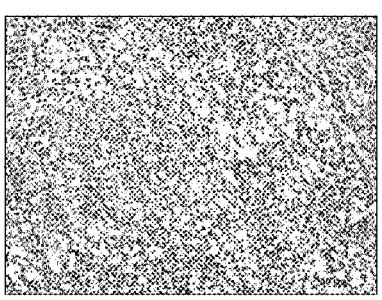
Figure 5:
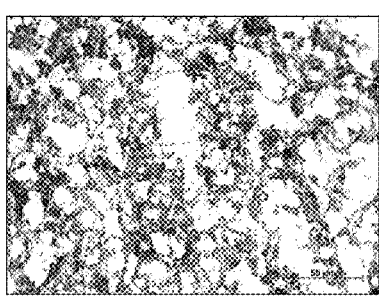
Figure 5:
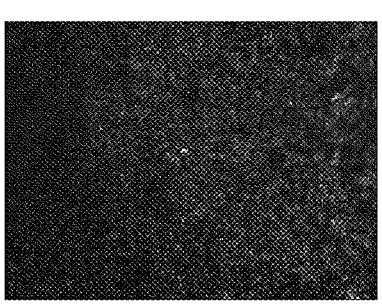
Figure 5:
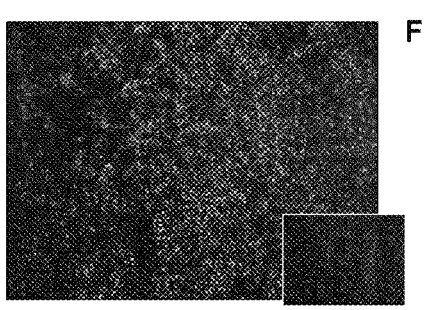

FIG. 5. Systemic administration of anle138b to high-level α-synuclein-expressing human melanoma xenografts affects their morphology and autophagy.

A-D. Hematoxylin and eosin (H&E)-stained tissue sections, prepared from one of the WM983-B human melanoma xenografts that did not contain anle138b A. B., and from one of the WM983-B human melanoma xenografts that had been resected from the animal that had received food pellets mixed with anle138b C. D. The photographs, shown in A. C. were taken at 100× magnification, and in B. D. at 40× magnification. E and F. LC3 immunohistochemical staining of a tissue section (100× magnification), prepared from one of the WM983-B human melanoma xenografts that had been resected from the animal that had received food pellets not containing anle138b and (E) from one of the WM983-B human melanoma xenografts that had been resected from the animal that had received food pellets mixed with anle138b (F). The inset in (F) shows a tissue section from the anle138b-containing WM983-B tumor, probed with Alexa-488 secondary antibody only and counterstained.

Figure 6:
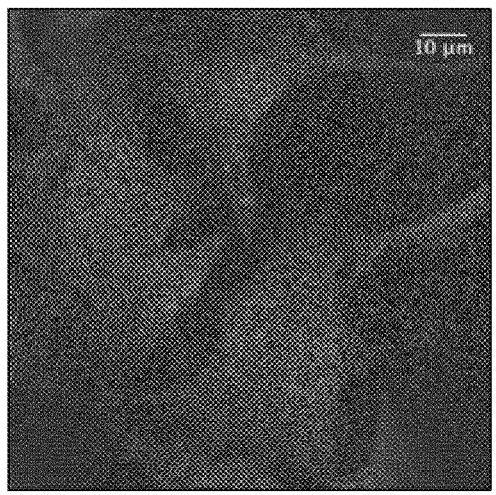
Figure 6:
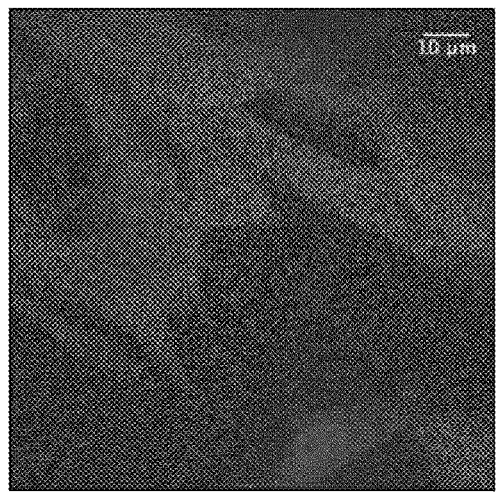
Figure 6:
Figure 6:
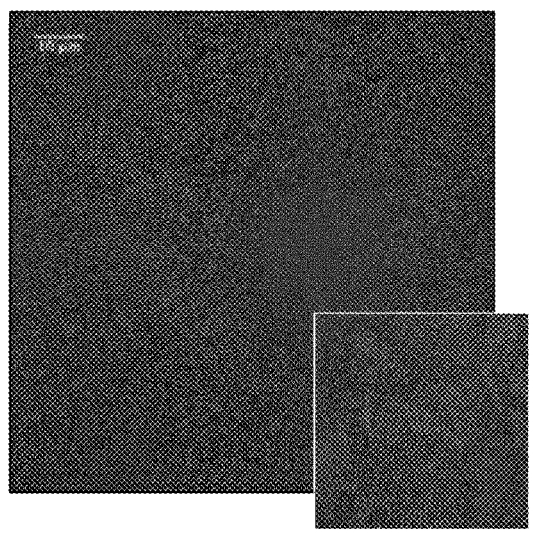

FIG. 6. Immunofluorescence analysis of expression of α-synuclein protein in melanoma cell lines WM983-A, WM983-B, SK-MEL-5, and WM1158.

The background-subtracted and mean-filtered fluorescence images, captured at 63× magnification, of the anti-α-synuclein antibody-probed melanoma cells are maximum intensity projections of 12 to 16 sections taken at the same laser power and gain settings. The inset in the image of WM1158 melanoma cells was captured at 3× higher laser power to make the cellular fluorescence visible.

Figure 7:
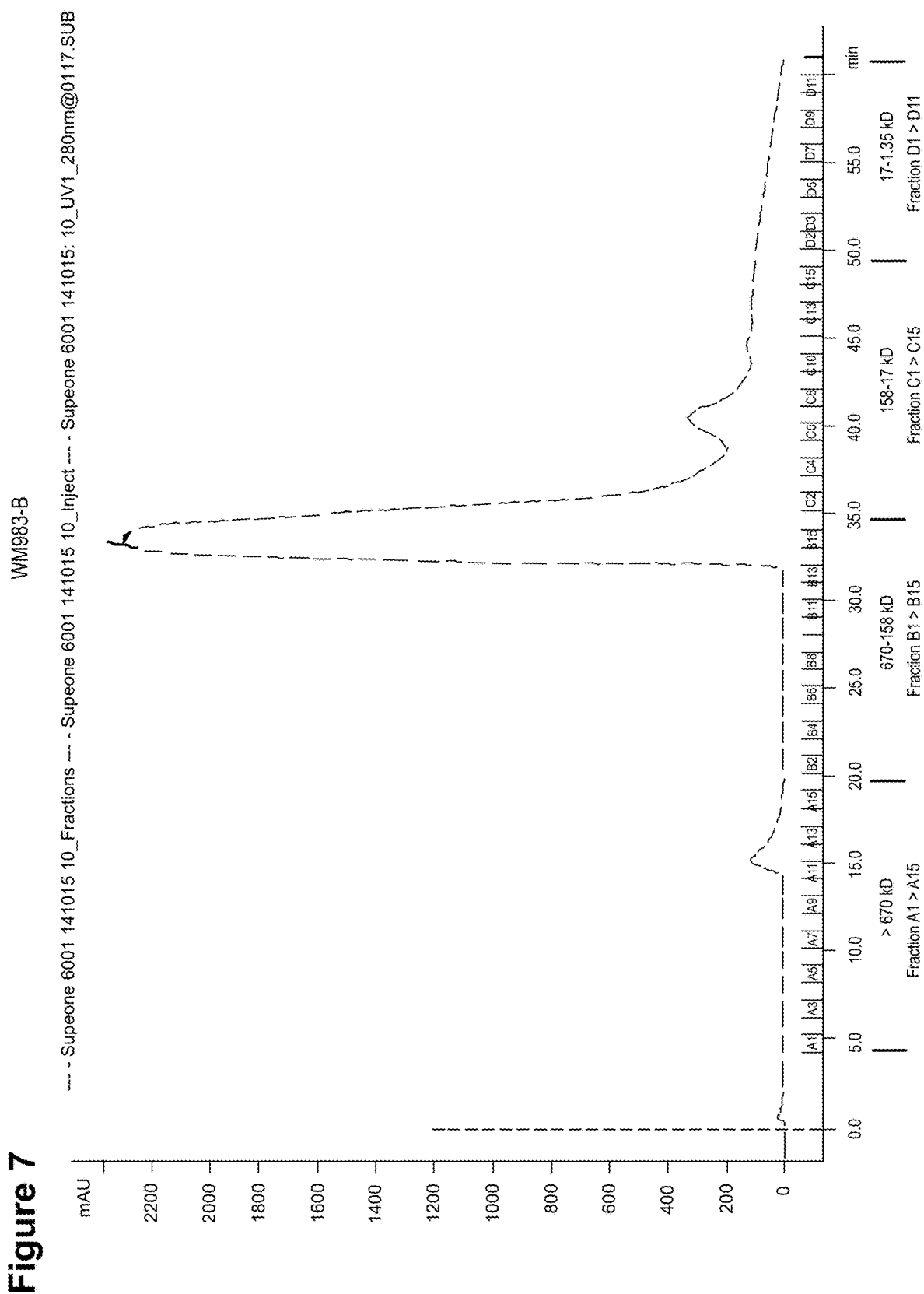

FIG. 7. Size exclusion chromatography elution profile of WM983-B melanoma whole-cell lysate.

Chromatogram of WM983-B melanoma whole-cell lysate separated by size exclusion chromatography. A total of 56 fractions were collected. Molecular weight sizes for the fractions were assessed using a gel filtration standard (bovine thyroglobulin-670 kD, bovine y-globulin-158 kD, chicken albumin-44 kD, horse myoglobin-17 kD, vitamin B12-1.35 kD).

Figure 8A:
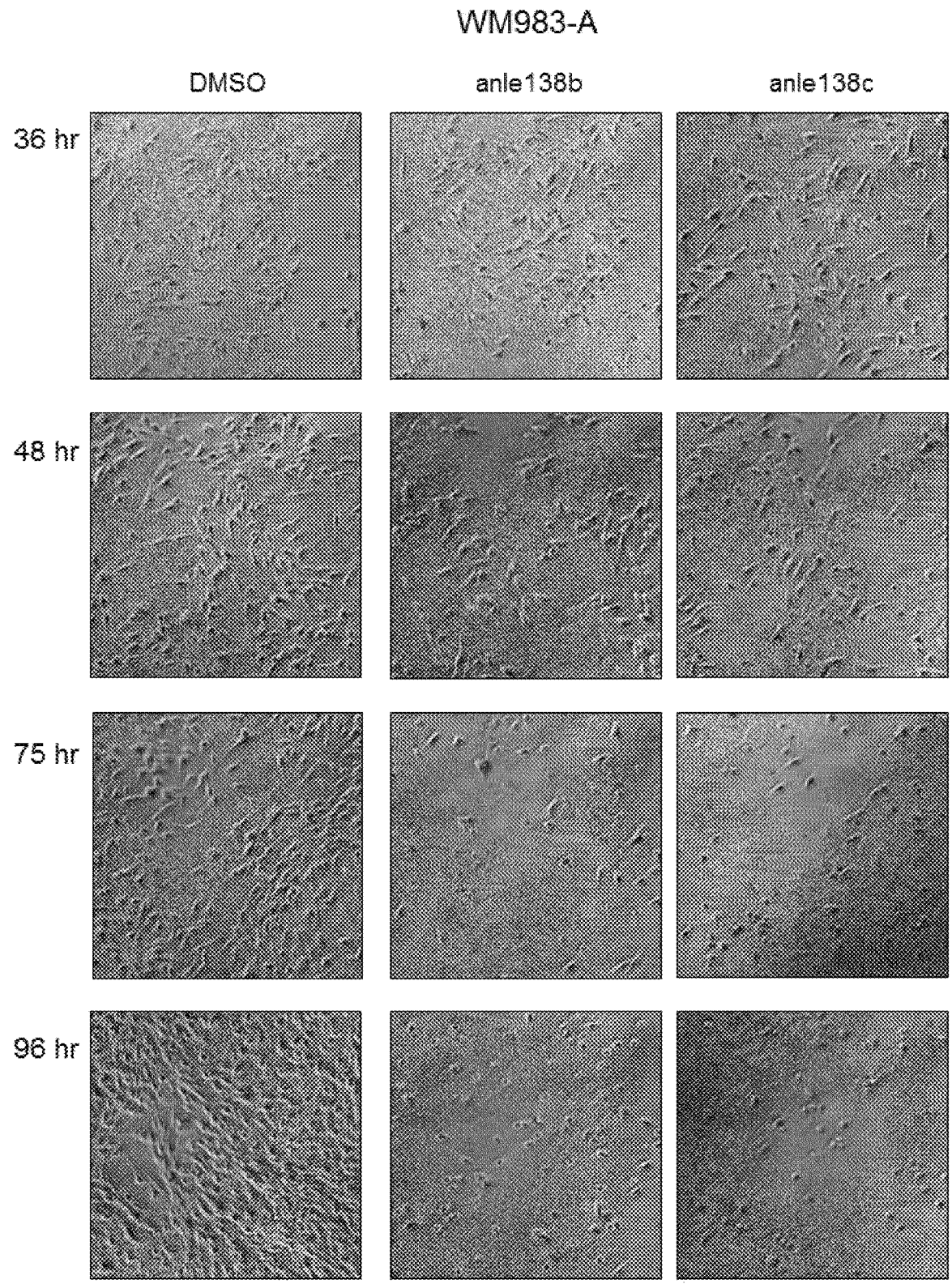
Figure 8B:
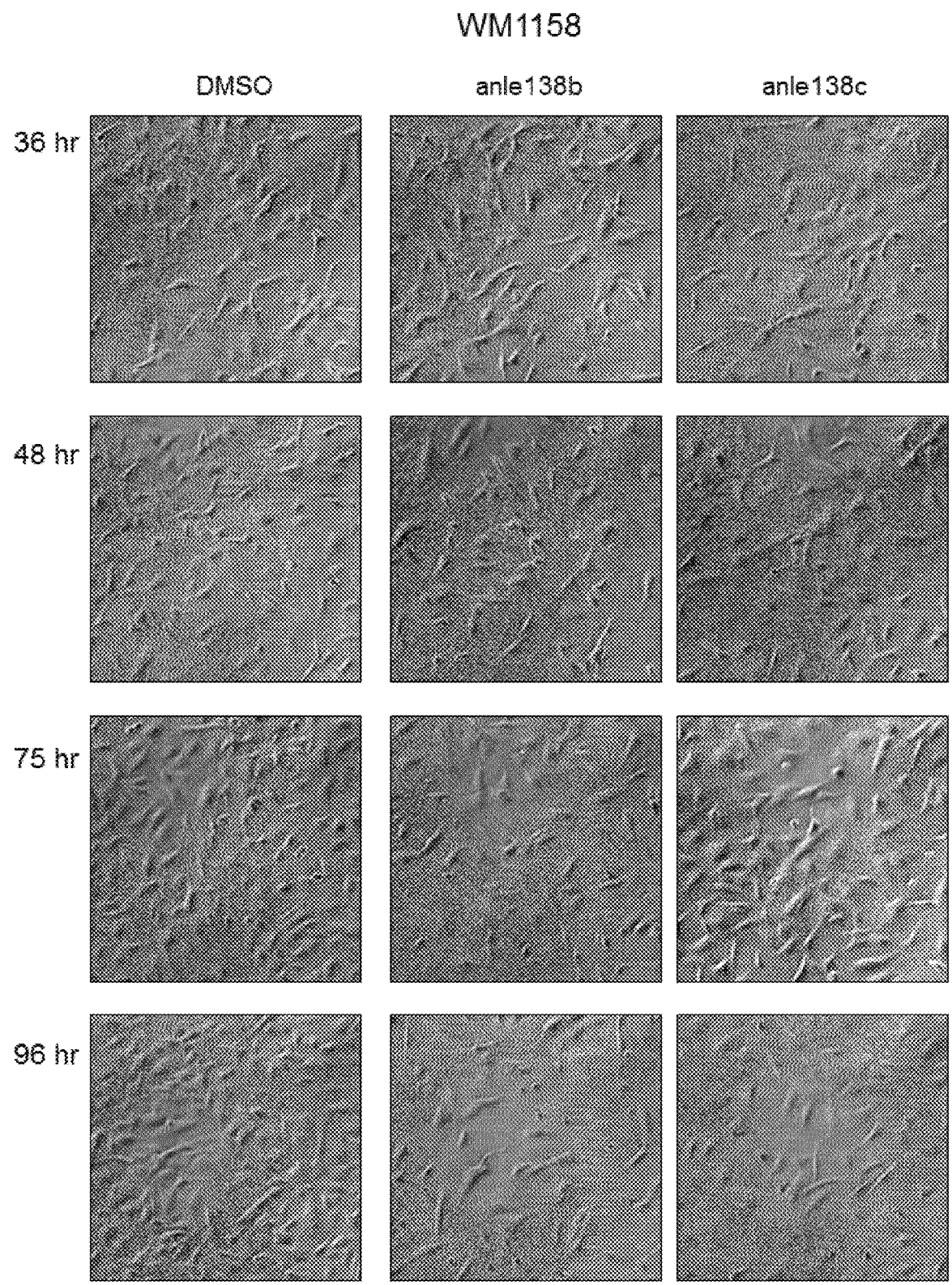

FIG. 8. Morphology of WM983-A (VGP) and WM1158 (RGP/VGP) melanoma cells treated with anle138b or anle138c.

Phase-contrast images, captured at 10× magnification, showing the morphology of A. WM983-A and B. WM1158 melanoma cells that had received DMSO only, or had been treated with a single dose (10 μM) of anle138b or anle138c for 36, 48, 75 or 96 hr, with replenishment of an equivalent dose of each compound or DMSO only at 48 hr.

Figure 9:
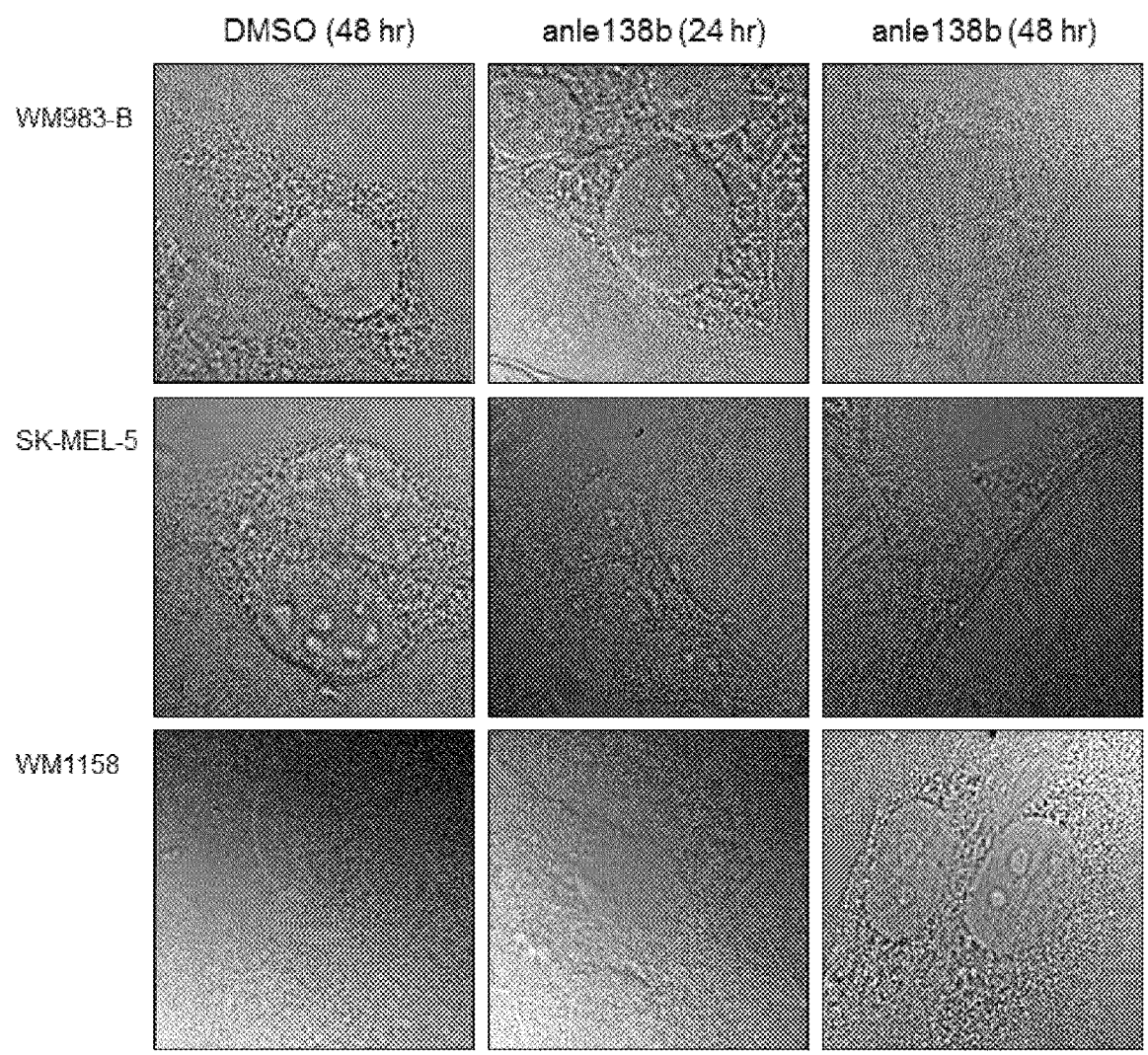

FIG. 9. Differential interference contrast images of the MitoTracker dye-stained WM983-B, SK-MEL-5, and WM1158 melanoma cells treated with anle138b. Differential interference contrast images showing the morphology of the MitoTracker dye-stained WM983-B, SK-MEL-5, and WM1158 melanoma cells that for 48 hr had received DMSO only, or were treated for 24 or 48 hr with a single dose (10 μM) of anle138b.

FIG. 10. Analytical high-performance liquid chromatography of high-level α-synuclein-expressing WM983-B human melanoma xenografts resected from a nude mouse that had received food pellets mixed with anle138b, and from a nude mouse that had received food pellets not containing anle138b.

A. B. Chromatograms showing the presence of anle138b in the two tumors resected from the animal that received food pellets mixed with anle138b.

C. Chromatogram of one the tumors resected from the animal that had received food pellets not containing anle138b.

D. Chromatogram of the anle138b DPP compound (reference sample).

DETAILED DESCRIPTION OF THE INVENTION

The invention is summarized by the embodiments listed in the claims. It is understood that combinations of all of the preferred embodiments listed hereinafter and in the claims are contemplated as being within the scope of the present invention.

The present invention relates to a compound represented by the general formula (E) for use in the treatment or prevention of melanoma.

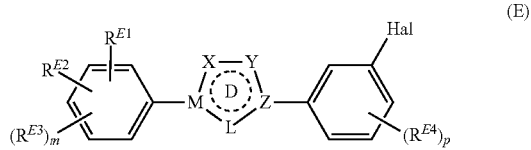

(E)

In the ring D X, Y and L are independently non-directionally selected from —C($R^1$)($R^2$)—, —C($R^3$)=, —N($R^4$)—, —N=, —O— and —S—;

M and Z are independently non-directionally selected from

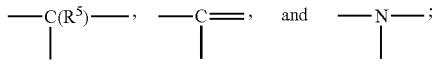

and

- - - - represent an optional double bond.

It is self-evident that X, Y, Z, L and M will be selected as valency and stability permits.

$R^1$, $R^2$, $R^3$, $R^4$, and $R^5$ are selected independently from hydrogen; $C_{1-4}$ alkyl; —$CH_2O$—P(=O)(OR)(OR); —$C_{1-4}$ alkylene-halogen; —$C_{1-4}$ alkylene-OH; —$C_{1-4}$ alkylene-$C_{1-4}$ alkoxy; —C(O)—$C_{1-4}$ alkyl; and $C_{6-10}$ aryl, wherein the aryl ring can be optionally substituted by $C_{1-4}$ alkyl or halogen. The $C_{6-10}$ aryl group is not particularly limited and can be, e.g., selected from phenyl and naphthyl. The halogen atom can be F, Cl, Br or I and is typically F or Cl.

Preferably $R^1$, $R^2$, $R^3$, $R^4$, and $R^5$ are selected independently from hydrogen; $C_{1-4}$ alkyl; —$CH_2O$—P(=O)(OR) (OR); —$C_{1-4}$ alkylene-halogen; —$C_{1-4}$ alkylene-OH; —$C_{1-4}$ alkylene-$C_{1-4}$ alkoxy; and —C(O)—$C_{1-4}$ alkyl. More preferably $R^1$, $R^2$, $R^3$, $R^4$ and $R^5$ are selected from hydrogen; $C_{1-4}$ alkyl; —$CH_2O$—P(=O)(OR)(OR); and —$C_{1-4}$ alkylene-halogen.

The choice of the substituent can depend on the intended use of the compounds of the formula (E). In one preferred embodiment at least one of $R^1$, $R^2$, $R^3$, $R^4$, and $R^5$ (more preferably $R^4$) is —$C_{1-4}$ alkylene-halogen. This is particularly useful if the compounds are to be employed as a probe for imaging deposits of aggregated proteins because it is then possible to label them quickly and efficiently with a detectable label such as a detectable halogen isotope. Examples of detectable halogen isotopes include $^{18}F$, $^{125}I$, $^{123}I$, $^{131}I$, $^{77}Br$ and $^{76}Br$, in particular $^{18}F$. It is of course possible to use a detectable halogen isotope as any of the other halogen atoms present in the compounds useful in the present invention, such as the halogen atoms attached to the phenyl ring.

In an alternative preferred embodiment, $R^1$, $R^2$, $R^3$, $R^4$, and $R^5$ are selected independently from hydrogen and $C_{1-4}$ alkyl, preferably hydrogen.

In another embodiment, at least one of $R^1$, $R^2$, $R^3$, $R^4$, and $R^5$ is selected from —$CH_2O$—P(=O)(OR)(OR). In a preferred embodiment, $R^4$ is —$CH_2O$—P(=O)(OR)(OR) and $R^1$, $R^2$, $R^3$, and $R^5$ are selected independently from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; —C(O)—$C_{1-4}$ alkyl; and $C_{6-10}$ aryl, wherein the aryl ring can be optionally substituted by $C_{1-4}$ alkyl or halogen. The $C_{6-10}$ aryl group is not particularly limited and can be, e.g., selected from phenyl and naphthyl. The halogen atom can be F, Cl, Br or I and is typically F or Cl. Preferably $R^1$, $R^2$, $R^3$, and $R^5$ are selected independently from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; and —C(O)—$C_{1-4}$ alkyl. More preferably $R^1$, $R^2$, $R^3$, and $R^5$ are selected from hydrogen; $C_{1-4}$ alkyl; and —$C_{1-4}$ alkylene-halogen. These compounds are particularly advantageous because they have increased water solubility.

The ring D is not particularly limited. Typical examples thereof include

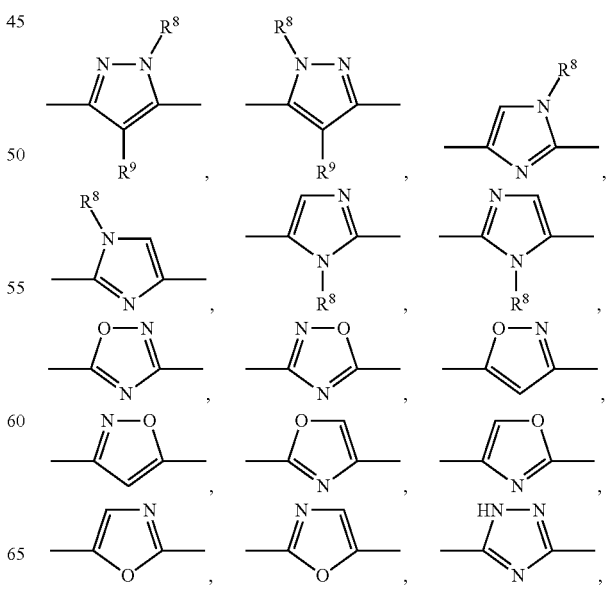

-continued

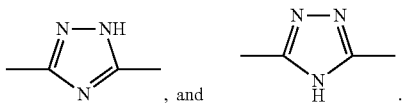, and

In one embodiment, examples include

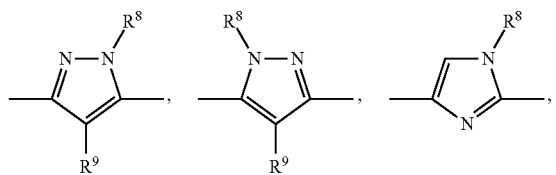

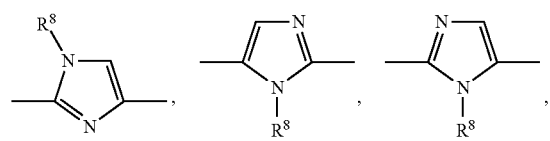

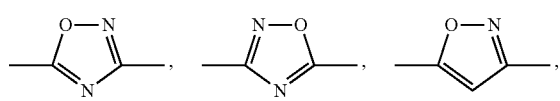

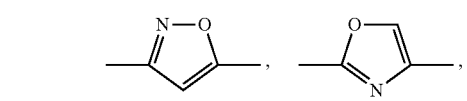

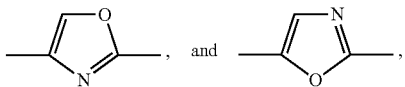

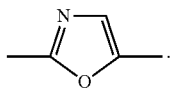

In another embodiment, examples thereof include

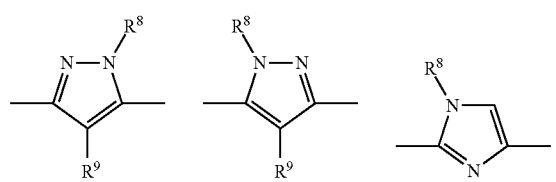

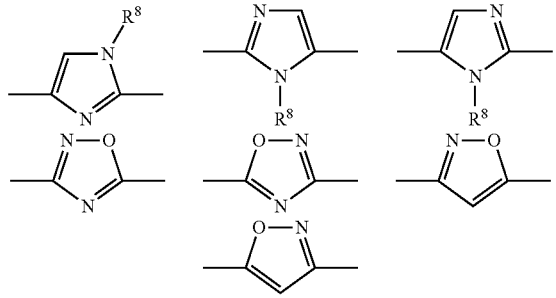

Preferred examples of ring D are

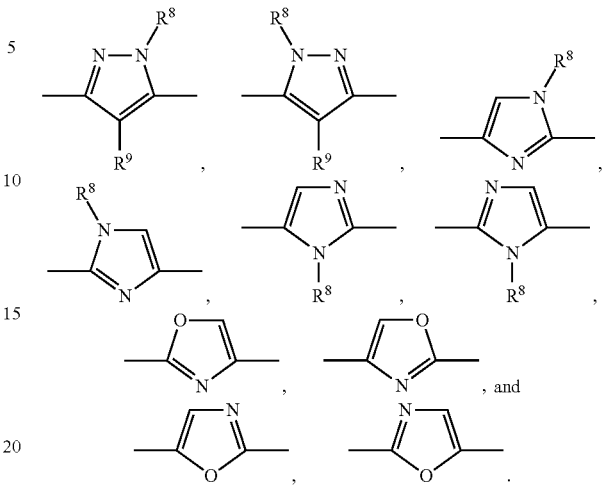

Particularly preferred examples of ring D are

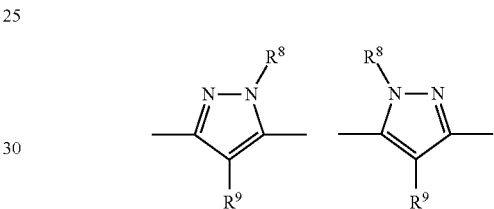

In the above formulae, $R^8$ is selected from hydrogen; $C_{1-4}$ alkyl; —$CH_2O$—$P(=O)(OR)(OR)$; —$C_{1-4}$ alkylene-halogen; —$C_{1-4}$ alkylene-OH; —$C_{1-4}$ alkylene-$C_{1-4}$ alkoxy; —$C(O)$—$C_{1-4}$ alkyl; and $C_{6-10}$ aryl (such as phenyl and naphthyl), wherein the aryl ring can be optionally substituted by $C_{1-4}$ alkyl or halogen. Preferably $R^8$ is selected from hydrogen; $C_{1-4}$ alkyl; —$CH_2O$—$P(=O)(OR)(OR)$; $C_{1-4}$ alkylene-halogen; —$C_{1-4}$ alkylene-OH; —$C_{1-4}$ alkylene-$C_{1-4}$ alkoxy; and —$C(O)$—$C_{1-4}$ alkyl. Further preferably $R^8$ is selected from hydrogen; $C_{1-4}$ alkyl; —$CH_2O$—$P(=O)(OR)(OR)$; —$C_{1-4}$ alkylene-halogen; and $C_{6-10}$ aryl (such as phenyl and naphthyl), wherein the aryl ring can be optionally substituted by $C_{1-4}$ alkyl or halogen. More preferably $R^8$ is selected from hydrogen; $C_{1-4}$ alkyl; —$CH_2O$—$P(=O)(OR)(OR)$; —$C_{1-4}$ alkylene-halogen. In one embodiment $R^8$ is selected from hydrogen; and $C_{1-4}$ alkyl, more preferably hydrogen. In an alternative embodiment $R^8$ is —$C_{1-4}$ alkylene-halogen. In another preferred embodiment, $R^8$ is —$CH_2O$—$P(=O)(OR)(OR)$. As was explained above, $R^8$ can be detectably labelled, if desired.

In the above formulae, $R^9$ is selected from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; —$C(O)$—$C_{1-4}$ alkyl; and $C_{6-10}$ aryl, wherein the aryl ring can be optionally substituted by $C_{1-4}$ alkyl or halogen. Preferably $R^9$ is selected from hydrogen; $C_{1-4}$ alkyl; $C_{1-4}$ alkylene-halogen; —$C_{1-4}$ alkylene-OH; —$C_{1-4}$ alkylene-$C_{1-4}$ alkoxy; and —$C(O)$—$C_{1-4}$ alkyl. More preferably $R^9$ is selected from hydrogen; $C_{1-4}$ alkyl; —$C_{1-4}$ alkylene-halogen. In one embodiment $R^9$ is selected from hydrogen; and $C_{1-4}$ alkyl, more preferably hydrogen. In an alternative embodiment $R^9$ is —$C_{1-4}$ alkylene-halogen. As was explained above, $R^9$ can be detectably labelled, if desired.

In a further embodiment, $R^8$ and $R^9$ are hydrogen. In yet another embodiment $R^8$ is —$C_{1-4}$ alkylene-halogen and $R^9$ is hydrogen. In yet another embodiment $R^8$ is —CH$_2$O—P(=O)(OR)(OR) and $R^9$ is hydrogen.

In one embodiment, the ring D is selected preferably from

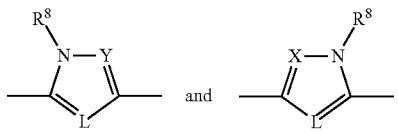

wherein $R^8$, X, Y and L are as defined above. More preferably the ring D is selected from

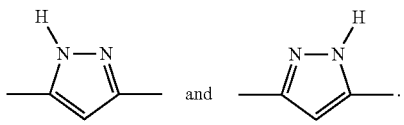

In one embodiment, the ring D is selected preferably from

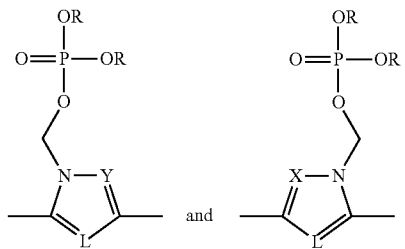

wherein X, Y and L are as defined above and R is as defined below. More preferably, the ring D is selected from

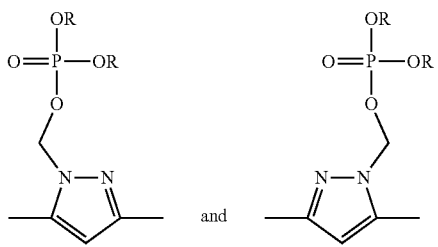

wherein R is as defined below.

Hal is selected from F, Cl, Br, and I and is preferably F, Cl or Br, more preferably Cl or Br, most preferably Br.

$R^{E1}$ is selected from hydroxy, $C_{1-6}$ alkoxy, and —NR$^{E5}$R$^{E6}$.

$R^{E2}$ is selected from hydrogen, halogen, hydroxy, $C_{1-6}$ alkoxy, and —NR$^{E5}$R$^{E6}$, preferably $R^{E2}$ is selected from hydrogen, hydroxy, $C_{1-6}$ alkoxy, and —NR$^{E5}$R$^{E6}$.

In an alternative embodiment, $R^{E1}$ and $R^{E2}$ together can non-directionally form a structure -T-(CR$^{E7}$R$^{E8}$)$_n$—V— as well as corresponding structures in which a double bond is present, if they are attached to adjacent carbon atoms. In this structure, T is selected from CR$^{E9}$R$^{E10}$, NR* and O and V is selected from CR$^{E9}$R$^{E10}$, NR* and O. In one embodiment, T is selected from CR$^{E9}$R$^{E10}$, NH and O and V is selected from CR$^{E9}$R$^{E10}$, NH and O. Preferably at least one of T and V is NR* or O, e.g., NH or O. Examples of such structures include —O—(CR$^{E7}$R$^{E8}$)$_n$—O—, —O—(CR$^{E7}$R$^{E8}$)$_n$—CR$^{E9}$R$^{E10}$, —NR*—(CR$^{E7}$R$^{E8}$)$_n$—NR*—, —NR*—(CR$^{E7}$R$^{E8}$)$_n$—O—, —NR*—(CR$^{E7}$R$^{E8}$)$_n$—CR$^{E9}$R$^{E10}$— or a corresponding structure in which a double bond is present. Further examples of such structures include —O—(CH$_2$)$_n$—O—, —O—(CF$_2$)$_n$—O—, —O—(CH$_2$)$_n$—CH$_2$—, —NR*—(CH$_2$)$_n$—NR*—, —NR*—(CF$_2$)$_n$—NR*—, —NR*—(CH$_2$)$_n$—O—, —NR*—(CF$_2$)$_n$—O—, —NR*—(CH$_2$)$_n$—CH$_2$— or a corresponding structure in which a double bond is present. Even further preferred examples of such structures include —O—(CH$_2$)$_n$—O—, —O—(CF$_2$)$_n$—O—, —O—(CH$_2$)$_n$—CH$_2$—, —NH—(CH$_2$)$_n$—NH—, —NH—(CF$_2$)$_n$—NH—, —NH—(CH$_2$)$_n$—CH$_2$— or a corresponding structure in which a double bond is present. As used herein, the expression "a corresponding structure in which a double bond is present" means that one or more double bonds can be present in the corresponding structure. For instance, if n=1 then —N=CH—NH— is a structure in which a double bond is present and which corresponds to —NH—CH$_2$—NH—. —O—CH=CH— is a further example of a structure in which a double bond is present. It corresponds to —O—(CH$_2$)$_n$—CH$_2$—. For instance, if n=2 then —N=CH—CH=N— is a structure in which a double bond is present and which corresponds to —NH—CH$_2$—CH$_2$—NH—. In these moieties one or more of the H can be replaced by a $C_{1-4}$ alkyl (e.g. methyl) group or halogen atom (e.g., F).

Examples of -T-(CR$^{E7}$R$^{E8}$)$_n$—V— include —O—(CH$_2$)—O—, —O—(CH$_2$)$_2$—O—, —O—(CH$_2$)$_3$—O—, —N=CH—CH=N—, —O—(CH$_2$)$_2$—NR*—, —CH$_2$—(CH$_2$)$_2$—O—, —CH=CH—O—, —CH=CH—NH—, and CH=CH—CH=CH—. In these moieties one or more of the H can be replaced by a $C_{1-4}$ alkyl (e.g. methyl) group or halogen atom (e.g., F).

Preferably $R^{E1}$ and $R^{E2}$ together form a structure —O—(CH$_2$)$_n$—O—. Examples thereof include —O—(CH$_2$)—O—, —O—(CH$_2$)$_2$—O— and —O—(CH$_2$)$_3$—O—, preferably —O—(CH$_2$)—O— and —O—(CH$_2$)$_2$—O—. It is assumed that this group might also be hydrolysed in vivo to the corresponding hydroxy groups.

n is 1 to 3; preferably n is 1 or 2. In one embodiment, n is 2. In another embodiment, n is 1.

$R^{E5}$ and $R^{E6}$ are selected independently from hydrogen and $C_{1-6}$ alkyl; preferably, $R^{E5}$ and $R^{E6}$ are selected independently from hydrogen and $C_{1-4}$ alkyl.

$R^{E7}$ and $R^{E8}$ are independently H, F, or $C_{1-6}$ alkyl, are preferably independently H or F, and are more preferably H.

$R^{E9}$ and $R^{E10}$ are independently H, F, or $C_{1-6}$ alkyl, are preferably independently H or F, and are more preferably H.

The position at which $R^{E1}$ and $R^{E2}$ are attached to the phenyl ring can vary.

In one embodiment, $R^{E1}$ and $R^{E2}$ are independently hydroxy or alkoxy are attached meta and para compared to the carbon atom which binds the phenyl ring to ring D.

In a second embodiment $R^{E1}$ and $R^{E2}$ are a structure -T-(CR$^{E7}$R$^{E8}$)$_n$—V— or a corresponding structure in which a double bond is present and are attached meta and para compared to the carbon atom which binds the phenyl ring to ring D. The above preferred definitions for the structure -T-(CR$^{E7}$R$^{E8}$)$_n$—V— apply analogously to this embodiment.

In a third embodiment $R^{E1}$ is —NR$^{E5}$R$^{E6}$ and is attached in para position compared to the carbon atom, which binds the phenyl ring to ring D.

Further substituents $R^{E3}$ can be optionally present on the phenyl ring in addition to $R^{E1}$, and $R^{E2}$. $R^{E3}$ can be a $C_{1-6}$ alkyl group or a $C_{6-10}$ aryl group (such as a phenyl or naphthyl group), preferably a $C_{1-6}$ alkyl group, more preferably a $C_{1-4}$ alkyl group. The number of substituents, m, is not particularly limited and is typically in the range of 0 to 2, preferably 0 or 1, typically 0.

Further substituents $R^{E4}$ can also be present. They are typically a halogen atom, a $C_{1-6}$ alkyl group or a $C_{6-10}$ aryl group (such as a phenyl or naphthyl group), preferably a halogen atom or a $C_{1-6}$ alkyl group, more preferably a $C_{1-6}$ alkyl group, most preferably a $C_{1-4}$ alkyl group. The number of substituents, p, is not particularly limited and is typically in the range of 0 to 2, preferably 0 or 1, typically 0.

R is a hydrogen atom or a cation. The cation can be any cation that is pharmaceutically acceptable for this type of compound. Examples are sodium, lithium, potassium, ammonium, in particular sodium. Further examples for groups compatible with the phosphate group of the compounds include groups of the structure R'R''R'''N such as ethanolamine, choline, lysine, meglumine, piperazine, and tromethamine. In the compounds both R can be hydrogen, both R can be cations (the same or different cations), or one R can be hydrogen and the other one can be a cation. Bivalent cations such as $Ca^{2+}$, $Mg^{2+}$, and $Zn^{2+}$ or trivalent cations such as $Al^{3+}$ are not suitable, as the resulting salts are not sufficiently water-soluble to be suitable as a prodrug. In a preferred embodiment, both R are sodium.

R* is a hydrogen atom or a $C_{1-6}$ alkyl group, preferably R* is a hydrogen atom or a $C_{1-4}$ alkyl group, more preferably a hydrogen atom.

Preferred examples of the compound represented by the formula (E) include compounds represented by formula (A)

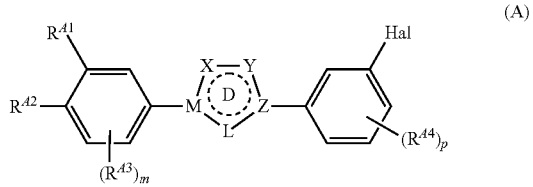

The definitions of X, Y, Z, M, L, ring D, m, p and Hal given above with respect to formula (E) apply analogously to formula (A).

$R^{A1}$ and $R^{A2}$ are each selected independently from hydrogen, halogen, hydroxy, $C_{1-6}$ alkoxy, and $-NR^{A5}R^{A6}$, with the proviso that at least one of $R^{A1}$ and $R^{A2}$ is hydroxy, $C_{1-6}$ alkoxy, or $-NR^{A5}R^{A6}$. Preferably $R^{A1}$ and $R^{A2}$ are selected independently from hydrogen, hydroxy, $C_{1-6}$ alkoxy, and $-NR^{A5}R^{A6}$.

Alternatively $R^{A1}$ and $R^{A2}$ can together non-directionally form a structure -T-$(CR^{E7}R^{E8})_n$—V—. The explanations give above with respect to $R^{E1}$ and $R^{E2}$ forming such a structure and in particular the above definitions of $R^{E7}$, $R^{E8}$, T, n and V apply analogously to $R^{A1}$ and $R^{A2}$ forming this structure.

In one embodiment $R^{A1}$ and $R^{A2}$ are independently hydroxy or alkoxy.

In a second embodiment $R^{A1}$ and $R^{A2}$ are a structure -T-$(CR^{E7}R^{E8})_n$—V— or a corresponding structure in which a double bond is present. The above preferred definitions for the structure -T-$(CR^{E7}R^{E8})_n$—V— apply analogously to this embodiment.

In a third embodiment $R^{A1}$ is $-NR^{A5}R^{A6}$ and $R^{A2}$ is hydrogen.

Further substituents $R^{A3}$ can be optionally present on the phenyl ring in addition to $R^{A1}$, and $R^{A2}$. $R^{A3}$ can be a $C_{1-6}$ alkyl group or a $C_{6-10}$ aryl group (such as a phenyl or naphthyl group), preferably a $C_{1-6}$ alkyl group, more preferably a $C_{1-4}$ alkyl group.

Further substituents $R^{A4}$ can also be present. They are typically a halogen atom, a $C_{1-6}$ alkyl group or a $C_{6-10}$ aryl group (such as a phenyl or naphthyl group), preferably a halogen atom or a $C_{1-6}$ alkyl group, more preferably a $C_{1-6}$ alkyl group, most preferably a $C_{1-4}$ alkyl group.

$R^{A5}$ and $R^{A6}$ are selected independently from hydrogen and $C_{1-6}$ alkyl; preferably, $R^{A5}$ and $R^{A6}$ are selected independently from hydrogen and $C_{1-4}$ alkyl.

Preferred examples of the compound represented by the formula (E) include compounds represented by formula (B)

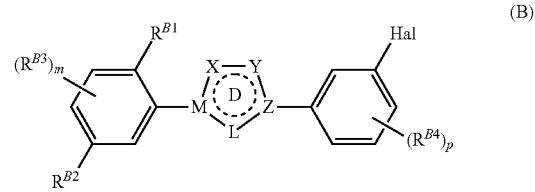

The definitions of X, Y, Z, M, L, ring D, m, p and Hal given above with respect to formula (E) apply analogously to formula (B).

$R^{B1}$ is selected from hydroxy, $C_{1-6}$ alkoxy, and $-NR^{B5}R^{B6}$. Preferably $R^{B1}$ is hydroxy or $C_{1-6}$ alkoxy.

$R^{B2}$ is selected from hydrogen, halogen, hydroxy, $C_{1-6}$ alkoxy; and $-NR^{B5}R^{B6}$, preferably $R^{B2}$ is selected from hydrogen, hydroxy, $C_{1-6}$ alkoxy; and $-NR^{B5}R^{B6}$.

In one embodiment $R^{B1}$ is hydroxy or $C_{1-6}$ alkoxy and $R^{B2}$ is hydrogen.

$R^{B5}$ and $R^{B6}$ are selected independently from hydrogen and $C_{1-6}$ alkyl, preferably $R^{B5}$ and $R^{B6}$ are selected independently from hydrogen and $C_{1-4}$ alkyl.

Further substituents $R^{B3}$ can be optionally present on the phenyl ring in addition to $R^{B1}$, and $R^{B2}$, $R^{B3}$ can be a $C_{1-6}$ alkyl group or a $C_{6-10}$ aryl group (such as a phenyl or naphthyl group), preferably a $C_{1-6}$ alkyl group, more preferably a $C_{1-4}$ alkyl group.

Further substituents $R^{B4}$ can also be present. They are typically a halogen atom, a $C_{1-6}$ alkyl group or a $C_{6-10}$ aryl group (such as a phenyl or naphthyl group), preferably a halogen atom or a $C_{1-6}$ alkyl group, more preferably a $C_{1-6}$ alkyl group, most preferably a $C_{1-4}$ alkyl group.

Preferred compounds which are useful in the present invention include

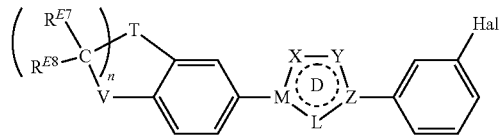

as well as corresponding structures in which a double bond is present in -T-$(CR^{E7}R^{E8})_n$—V—,

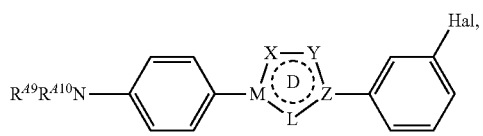

-continued
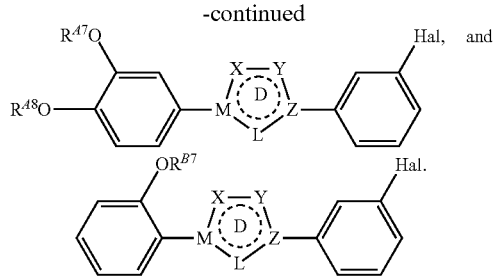
Further preferred compounds include
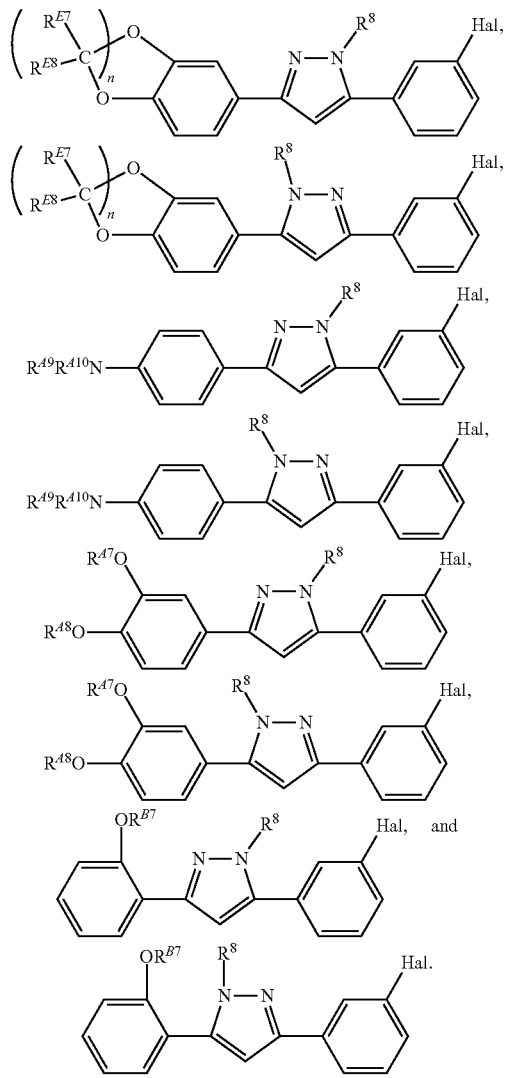
Further preferred compounds include
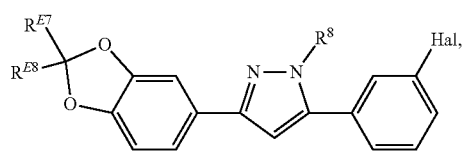
-continued
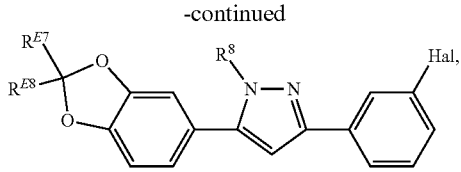
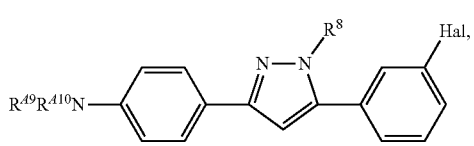
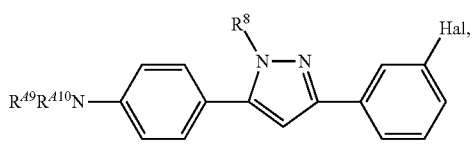
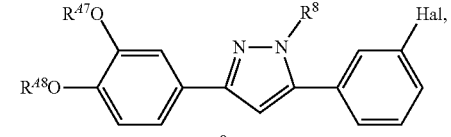
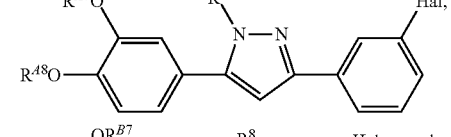
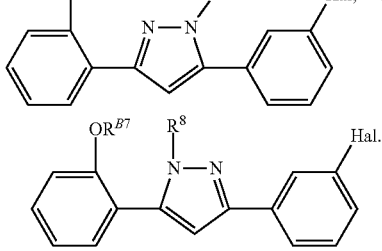
More preferred compounds include
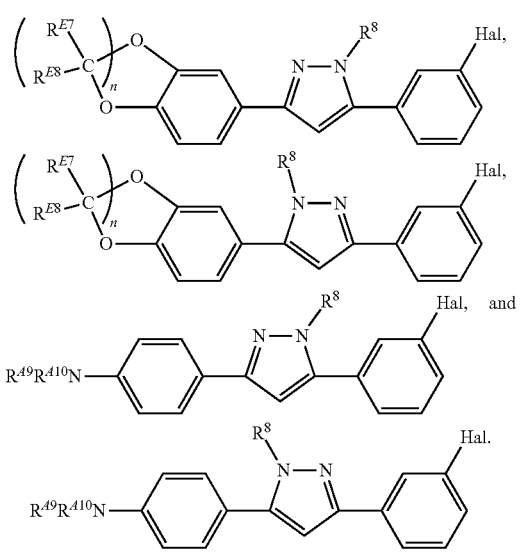

More preferred compounds include

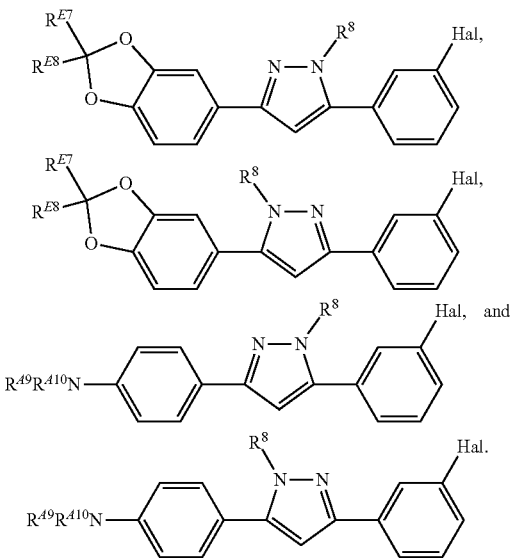

The definitions given above with respect to X, Y, Z, M, L, ring D, T, V, n, $R^{E7}$, $R^{E8}$, $R^{A7}$, $R^{A8}$, $R^{A9}$, $R^{A10}$, $R^{B7}$, $R^8$ and Hal apply analogously to these compounds.

$R^{A7}$ is H or $C_{1-6}$ alkyl, preferably H or $C_{1-4}$ alkyl.
$R^{A8}$ is H or $C_{1-6}$ alkyl, preferably H or $C_{1-4}$ alkyl.
$R^{A9}$ is H or $C_{1-6}$ alkyl, preferably H or $C_{1-4}$ alkyl.
$R^{A10}$ is H or $C_{1-6}$ alkyl, preferably H or $C_{1-4}$ alkyl.
$R^{B7}$ is H or $C_{1-6}$ alkyl, preferably H or $C_{1-4}$ alkyl.

The following compounds are particularly preferred:

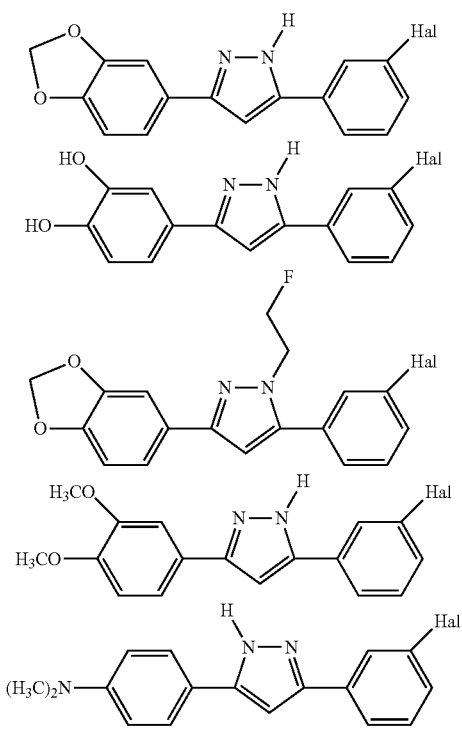

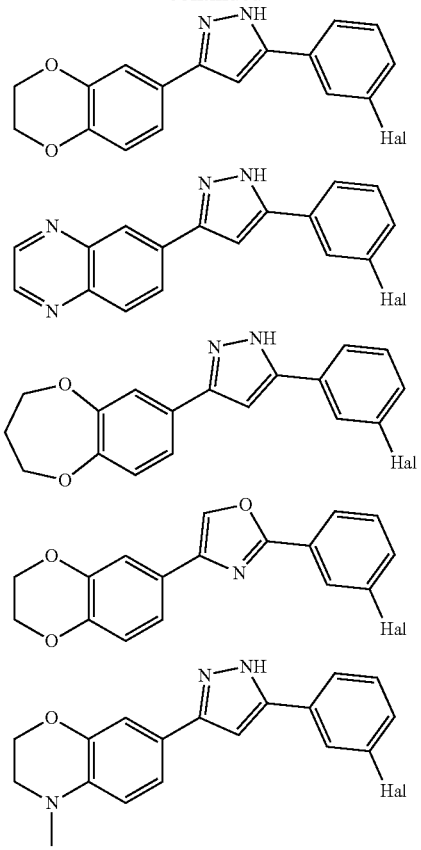

wherein Hal is Cl or Br, preferably Hal is Br.

Most preferred are presently the following compounds

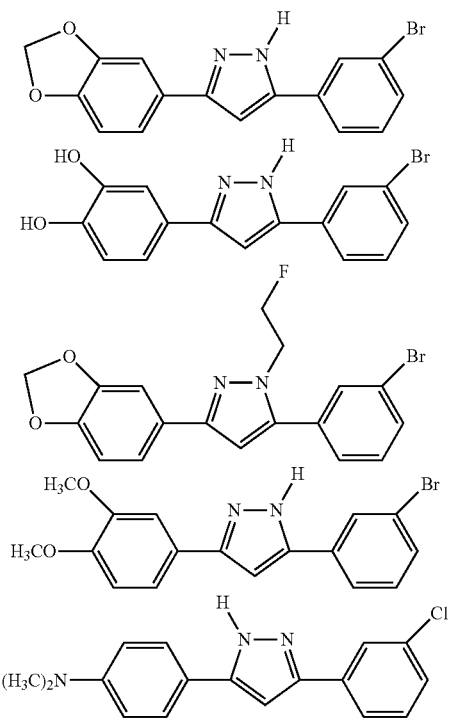

-continued

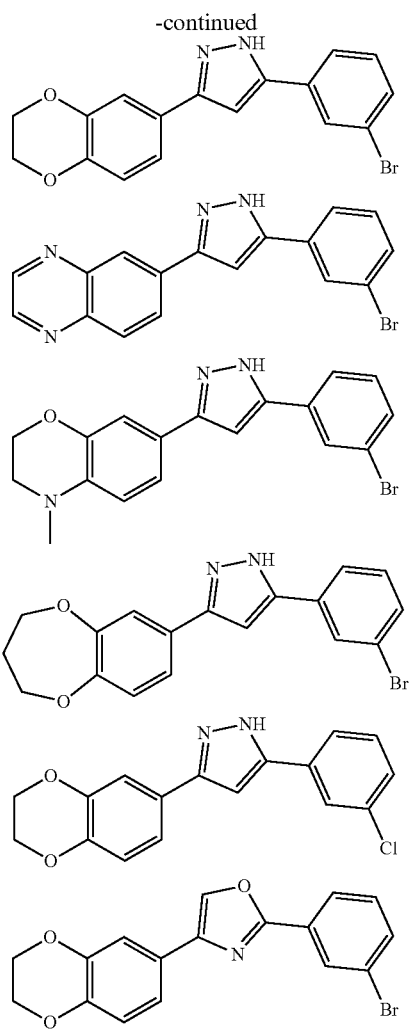

Some specific preferred compounds include:

Anle138b (5-(3-Bromophenyl)-3-(3,4-methylenedioxyphenyl)-1H-pyrazole) which is defined by the following structure:

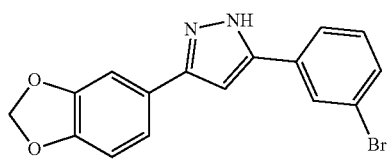 [SMILES: Brc1cccc(-c2cc(-c3ccc4c(c3)OCO4)n[nH]2)c1]

Sery335b (5-(3-Chlorophenyl)-3-(3,4-methylenedioxyphenyl)pyrazole) which is defined by the following structure:

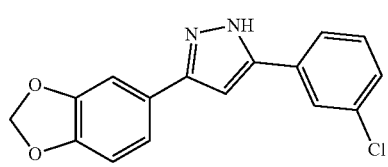 [SMILES: Clc1cccc(-c2cc(-c3ccc4c(c3)OCO4)n[nH]2)c1]

Anle253b (5-(3-Bromophenyl)-3-(4-dimethylaminophenyl)-1H-pyrazole) which is defined by the following structure:

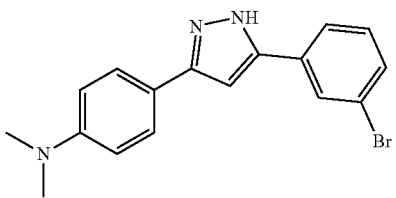 [SMILES: CN(C)c1ccc(-c2cc(-c3cccc(Br)c3)[nH]n2)cc1]

The present compounds including the above-mentioned specific compounds can be provided in the form of phosphate derivatives that are stable and thus, particularly suitable as prodrugs for oral use in humans.

As disclosed in EP15199972.9, a phosphate substitution on the ring D, particularly at one nitrogen in the diazole ring of 3,5-diphenyl-pyrazole or 3,5-diphenyl-imidazole compounds, improves water solubility without impairing stability. This chemical modification leads to the provision of a prodrug of this valuable therapeutic agent, defined by the following isomeric structures:

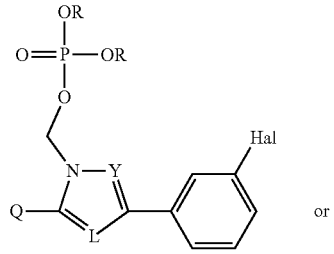

or

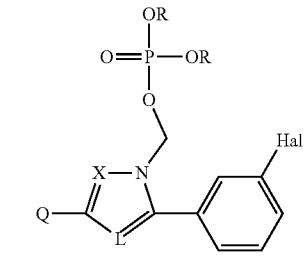

wherein one of Y and L is N or one of X and L is N, respectively, and the other one is $CR^{10}$ wherein $R^{10}$ is selected from hydrogen, $C_{1-4}$ alkyl, $C_{1-4}$ alkyl substituted with at least one halogen; and $C_{6-10}$ aryl, wherein the aryl ring can be optionally substituted by $C_{1-4}$ alkyl or halogen;

wherein Q is

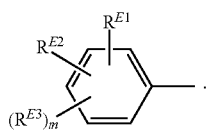

In one embodiment, Q is

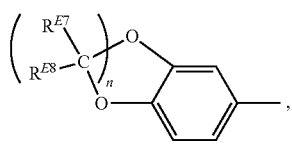

such as

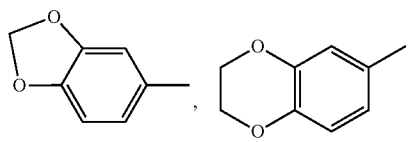

and Hal is halogen selected from chlorine or bromine. In another embodiment, Q is

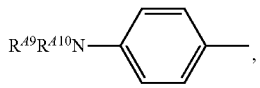

such as

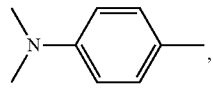

and Hal is bromine; and
wherein each R independently is hydrogen or a cation.

In a preferred embodiment, Y is N and L is —CH— or X is N and L is —CH—, respectively.

In a preferred embodiment the compounds are defined by the following isomeric structures:

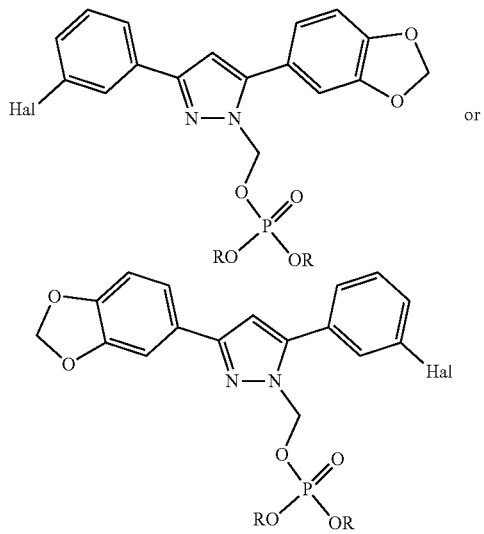

wherein Hal is a halogen selected from chlorine or bromine, and wherein each R independently is selected from hydrogen, or a cation.

In a further preferred embodiment, the compounds are defined by the following isomeric structures:

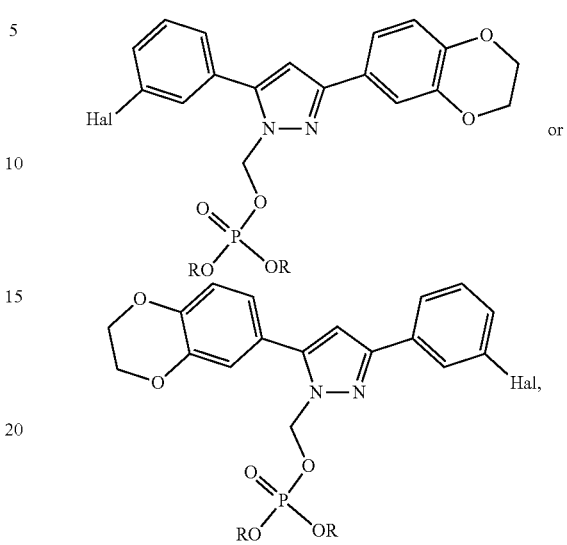

wherein Hal is a halogen selected from chlorine or bromine, and wherein each R independently is selected from hydrogen, or a cation.

In a further preferred embodiment, the derivative of the present compounds is a phosphate derivative of anle253b with the following isomeric structures:

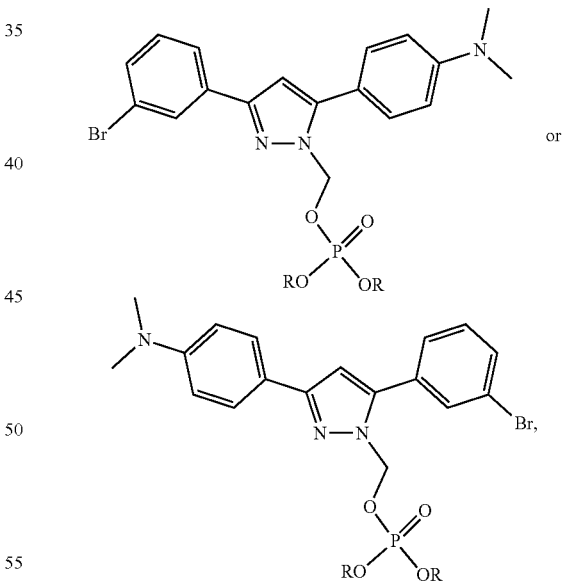

wherein each R independently is selected from hydrogen, or a cation.

In the phosphate derivatives, the cation can be any cation that is pharmaceutically acceptable for this type of compound. Examples are sodium, lithium, potassium, ammonium, in particular sodium. Further examples for groups compatible with the phosphate group of the compounds include groups of the structure R'R"R'"N such as ethanolamine, choline, lysine, meglumine, piperazine, and tromethamine. In the compounds both R can be hydrogen, both R can be cations (the same or different cations), or one R can be hydrogen and the other one can be a cation. Bivalent cations such as $Ca^{2+}$, $Mg^{2+}$, and $Zn^{2+}$ or trivalent cations such as $Al^{3+}$ are not suitable, as the resulting salts are not sufficiently water-soluble to be suitable as a prodrug. In a preferred embodiment, both R are sodium.

Furthermore, the free acid form of the phosphate derivatives is also suitable as a prodrug.

It has been found that the disodium phosphate derivative is stable and yields high levels of active compound in brain and blood.

In a preferred embodiment, the compound is a disodium phosphate of one of the following structures or a mixture thereof:

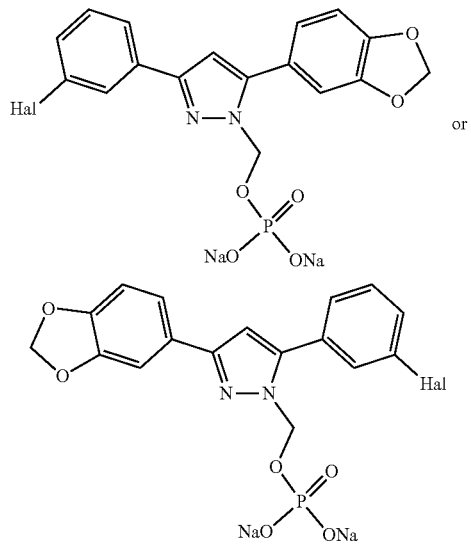

In a preferred embodiment, the phosphate derivative is a disodium methyl phosphate of the therapeutic agent anle138b, i.e. a compound as shown above, wherein Hal is chlorine or bromine. The former derivative is referred to as sery335b, the latter derivative is referred to as sery433. Both can be in the form of one of the isomers or can be a mixture of both isomers. Isomers sery433a or sery433b are shown below:

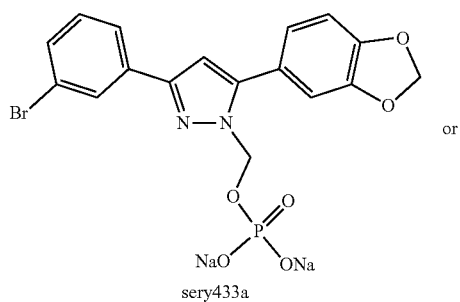

sery433a

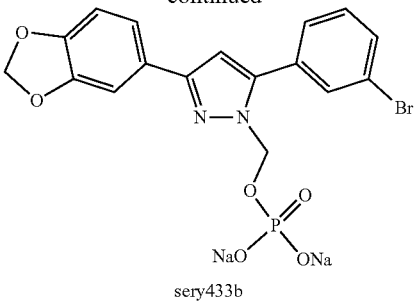

sery433b

In a preferred embodiment sery433 is an isomeric mixture of sery433a and sery433b, for example with a ratio of sery433b:sery433a=2:3 according to experimental data obtained by 2D-NOESY NMR. Both isomeric forms are converted into the bioactive drug within the body.

It has been surprisingly found that the phosphate derivatization provides a therapeutic compound with the following favorable characteristics:
stability under normal storage conditions,
non-toxicity, and
stability during the passage from os to gut.

The phosphate derivatives are characterized by solubility in water of above 1 mM. The phosphate derivatives are also characterized by their stability in water.

When using the phosphate derivatives the therapeutically active compound is found in the brain and the blood in increased amounts. It is assumed, without being bound by theory, that the active therapeutic compound is released from the phosphate derivatives by membrane-bound intestinal alkaline phosphatase (IAP) and, thus, close to the gut epithelium, where it is directly transferred in the blood stream. Possibly the compound is released in a mainly monodisperse form that can then be taken up from the gut to the blood. The pharmacokinetic characteristics of the phosphate derivatives lead to therapeutically useful levels of active compound in the brain and blood in mice and rats.

For example, the active compound anle138b is released from the prodrug sery433 at the intestine wall by enzymatic cleavage of the phosphate group from the compound by the membrane-bound intestinal alkaline phosphatase (IAP). Without being bound by theory, it is contemplated that high levels of active compound in blood and brain are possible because the concentration of the active compound at the intestine wall is below the concentration leading to precipitation of the active compound. Furthermore, it is contemplated that the IAP does not release the active therapeutic compound into the lumen of the gut upon cleavage, but holds on to the compound until it has passed onto and through the gut membrane for passive transport into the blood.

The present compounds can be provided in a composition which comprises at least one of the compounds as defined in the claims and optionally a pharmaceutically acceptable excipient. The composition can comprise one tautomeric form of the present compounds or both tautomeric forms. The composition can also comprise more than one compound and any of the compounds used in a composition can be either one of both tautomers or a mixture thereof. Thus, a therapeutic composition for use in treating melanoma can comprise one of the isomers or a mixture of both isomers. Both isomeric forms are converted into the bioactive drug within the body. The composition can further comprise at least one excipient as is known to the skilled person. An excipient can be any compound known for this purpose and the amounts and types of excipients used for a specific composition are those usually used and depend on the form and type of composition.

The present compounds can also be present in the form of ethers, esters, solvates or salts thereof.

The present compounds form salts, which are also within the scope of this invention. Reference to a compound useful in the present invention herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the present compounds may be formed, for example, by reacting a compound with an amount of acid or base, such as an equivalent amount, in a medium such as one in which the salt precipitates or in an aqueous medium followed by lyophilization.

The compounds which contain a basic moiety, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (e.g., those formed with sulfuric acid), sulfonates (e.g., those mentioned herein), tartrates, thiocyanates, toluenesulfonates such as tosylates, undecanoates, and the like.

The compounds that contain an acidic moiety may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (e.g., organic amines) such as benzathines, dicyclohexylamines, hydrabamines (formed with N,N-bis (dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the invention are also contemplated herein. Solvates of the present compounds include, for example, hydrates.

The term "prodrug" as employed herein denotes a compound that upon administration to a subject undergoes chemical conversion by metabolic or chemical processes to yield a compound as defined in the claims or a salt and/or solvate thereof.

Esters of the present compounds include $C_{1-6}$ alkyl esters, preferably $C_{1-4}$ alkyl esters.

Ethers of the present compounds include $C_{1-6}$ alkyl ethers or halogenated $C_{1-6}$ alkyl ethers (such as $CF_3$), preferably $C_{1-4}$ alkyl ethers or halogenated $C_{1-4}$ alkyl ethers.

The present compounds may exist in their tautomeric form (e.g., as an amide or imino ether). In the case of pyrazoles, for instance, the compounds exist in two tautomeric forms:

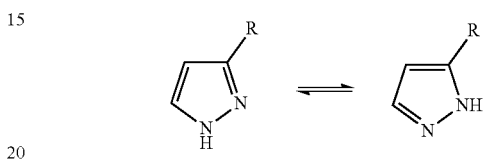

Therefore "anle138b" can be described by the following structural formulae:

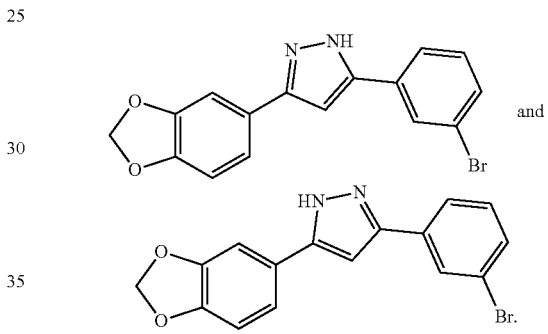

All such tautomeric forms are contemplated herein as part of the present invention. Whenever in the description one of the above-mentioned structures is disclosed, the other structure, as well as mixtures of both structures, are intended to be encompassed. The same applies to other structural formulae describing phosphate derivatives for example phosphate derivatives of DPP compounds, such as sery335b and anle253b.

All stereoisomers of the present compounds (e.g., those which may exist due to asymmetric carbons on various substituents), including enantiomeric forms and diastereomeric forms, are contemplated within the scope of this invention. Individual stereoisomers of the present compounds may, for example, be substantially free of other isomers (e.g., as a pure or substantially pure optical isomer having a specified activity), or may be admixed, for example, as racemates or with all other, or other selected, stereoisomers. The chiral centers of the present compounds may have the S or R configuration as defined by the IUPAC 1974 Recommendations.

The racemic forms can be resolved by physical methods, such as fractional crystallization, separation or crystallization of diastereomeric derivatives or separation by chiral column chromatography. The individual optical isomers can be obtained from the racemates by any suitable method, including without limitation, salt formation with an optically active acid followed by crystallization.

All configurational isomers of the present compounds are contemplated, either in admixture or in pure or substantially pure form. The definition of compounds which are useful in the present invention embraces both cis (Z) and trans (E) alkene isomers, as well as cis and trans isomers of cyclic hydrocarbon or heterocyclo rings.

Throughout the specification, groups and substituents thereof may be chosen to provide stable moieties and compounds.

The compounds of the formula (E) can be provided in the form of a pharmaceutical composition which optionally includes a pharmaceutically acceptable carrier.

The present invention further relates to the compound of the present invention as well as an ether, ester, solvate or salt thereof for the use in the treatment or prevention of melanoma. Further embodiments are the use of a compound of the present invention for the preparation of a pharmaceutical composition for treating or preventing melanoma as well as a method of treating or preventing melanoma comprising administering a therapeutically effective amount of a compound of the present invention to a patient in need thereof.

In accordance with the present invention, the term "pharmaceutical composition" relates to a composition for administration to a patient, preferably a mammal, more preferably a human patient. The pharmaceutical composition comprises the compounds recited above and, optionally, further molecules capable of altering the characteristics of the present compounds thereby, for example, stabilizing, modulating and/or activating their function. The composition may be in solid, liquid or gaseous form and may be, inter alia, in the form of (a) powder(s), (a) tablet(s), (a) solution(s) or (an) aerosol(s). The pharmaceutical composition may comprise, optionally and additionally, a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well-known conventional methods.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations. The skilled person knows that the effective amount of pharmaceutical compositions administered to an individual will depend, inter alia, on the nature of the compound.

Pharmaceutical compositions may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58 481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133 988). Sustained release pharmaceutical composition also include liposomally entrapped compound. Liposomes containing the pharmaceutical composition are prepared by methods known per se: DE 32 18 121; Epstein et al., Proc. Natl. Acad. Sci. (USA) 82:3688-3692 (1985); Hwang et al., Proc. Natl. Acad. Sci. (USA) 77:4030-4034 (1980); EP 52 322; EP 36 676; EP 88 046; EP 143 949; EP 142 641; Japanese Pat. Appl. 83-118008; U.S. Pat. Nos. 4,485,045 and 4,544,545; and EP 102324. Ordinarily, the liposomes are of the small (about 200-800 Angstroms) unilamellar type in which the lipid content is greater than about 30 mol % cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers, or both. Then, if necessary, the product is shaped into the desired formulation. Preferably, the carrier is a parenteral carrier, more preferably a solution that is isotonic with the blood of the recipient. Examples of such carrier vehicles include water, saline, Ringer's solution, and dextrose solution. Non-aqueous vehicles, such as fixed oils and ethyl oleate, are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 µm membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

The present invention further relates to a method of treating or preventing melanoma comprising administering a therapeutically effective amount of a compound of the present invention to a patient in need thereof.

As used herein the term "therapeutically effective amount" refers to an amount sufficient to elicit the desired biological response. In the present invention the desired biological response is the killing/death of melanoma cells.

The present compounds can be used to treat and/or prevent melanoma, including all clinical, pathologic, and histologic types and stages encompassing cutaneous melanoma and non-cutaneous melanoma. It is understood that the instant compounds can be used in preventing all cutaneous and non-cutaneous melanomas and their precursor lesions, and in the treatment of all clinical, pathologic, and histologic stages encompassing all cutaneous and all non-cutaneous melanomas. The present compounds can be used alone or in combination with any other known melanoma targeted therapy or immunotherapy. Examples of known therapies for melanoma are targeted therapies with small molecule inhibitors to BRAF kinase or MEK and immunotherapies with checkpoint inhibitors (Margolin K, The Promise of Molecularly Targeted and Immunotherapy for Advanced Melanoma. Curr Treat Options Oncol. 2016 September; 17(9):48. Prieto P A, Reuben A, Cooper Z A, Wargo J A. Targeted Therapies Combined With Immune Checkpoint Therapy. Cancer J. 2016 March-April; 22(2):138-46).

The compounds, useful in the present invention, are known from WO 2010/000372 and EP15199972.9. The entire disclosure of these documents including the definitions of the compounds and the preferred embodiments as well as the methods of preparing the compounds are incorporated herein by reference. The present compounds can be prepared by any of the applicable techniques of organic synthesis. Many such techniques are elaborated in L. F. Tietze, Th. Eicher "Reaktionen and Synthesen", 2. Auflage (Georg Thieme Verlag, Stuttgart, N Y, 1991), T. W. Greene, P. G. M. Wuts "Protective Groups in Organic Synthesis", Third Edition (John Wiley & Sons, N Y, 1999), as well as J. March "Advanced Organic Chemistry", Third Edition (John Wiley & Sons, N Y, 1985).

Generally, the reaction conditions such as temperature, reaction time, solvents, workup procedures, and the like, will be those common in the art for the particular reaction to be performed. The cited reference material, together with the material cited therein, contains detailed descriptions of such conditions. Typically, the temperatures will be −80° C. to 150° C., solvents will be aprotic or erotic, and reaction times will be 10 seconds to 10 days. Workup typically consists of quenching any unreacted reagents followed by partition between a water/organic layer system (extraction) and separating the layer containing the product.

Standard synthetic techniques such as use of anhydrous reaction conditions (e.g., inert gas environments) are common in the art and will be applied when applicable.

Modifications of each of the below schemes leads to various analogues of the specific exemplary materials produced below. The citations given below describing suitable methods of organic synthesis are applicable to such modifications.

In each of the below exemplary schemes it may be advantageous to separate reaction products from one another and/or from starting materials. The desired products of each step are separated and/or purified (hereinafter separated) to the desired degree of homogeneity by the techniques common in the art. Typically, such separations involve multiphase extractions, crystallisation from a solvent or solvent mixture, distillation, sublimation, or chromatography. Chromatography can involve any number of methods including, for example, size exclusion or ion exchange chromatography, high, medium or low pressure chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction, or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

In particular, the present compounds can be prepared in an manner which is analogous to procedures which are disclosed, for instance, in M. Ono et al. (Bioorganic & Medicinal Chemistry 16 (2008) 6867-6872), WO 2008/131148, WO 2004/080972, WO 2004/072050, and WO 98/17652. Preferable routes are also exemplified in the example section of the present invention as well as in WO 2010/000372 and EP15199972.9.

These methods are intended to illustrate the nature of such preparations and are not intended to limit the scope of applicable methods.

The following examples are intended to illustrate the invention. However, they are not to be construed as limiting.

EXAMPLES

Materials and Methods

All starting materials and solvents were purchased from ABCR, Acros, Alfa Aesar, Fluorochem, Sigma-Aldrich or Merck and used as such unless noted otherwise.

Melting points were determined on a Stuart Scientific (BIBBY, UK) melting point apparatus using open glass capillaries and are uncorrected. Thin layer chromatography (TLC): Macherey-Nagel precoated sheets, 0.25 mm ALUGRAM® SIL G/UV254 plates, detection with UV and/or by charring with 10 wt % ethanolic phosphomolybdic acid reagent followed by heating at 200° C. Flash column chromatography was performed by using Merck silica gel 60 (0.063-0.100 mm). Analytical and preparative high performance liquid chromatography (HPLC) were performed by using a Waters HPLC system with a Waters 996 Photodiode Array Detector. All separations involved a mobile phase of 0.1% trifluoroacetic acid (TFA) (v/v) in water (solvent A) and 0.1% TFA in acetonitrile (solvent B). HPLC was performed by using a reversed-phase (RP) column Eurospher RP 18, 100 Å, 5 µm, 250×4.6 mm (analytical) and 250×16 mm (preparative) at flow rates of 1 mL·min$^{-1}$ (analytical) and 7 mL·min$^{-1}$ (preparative). Electrospray ionization mass spectrometry (ESI-MS) and liquid chromatography/mass spectrometry (LC/MS) analyses were obtained by using a Waters Micromass ZQ 4000 mass spectrometer in conjunction with the Waters HPLC apparatus described above. NMR spectra were recorded at a temperature of 298 K by using a 400 MHz Bruker Avance spectrometer (Bruker AG, Rheinstetten, Germany) equipped with a TXI HCN z-gradient probe. All spectra were processed by using TOPSPIN2 (Bruker AG, Karlsruhe, Germany). $^{1}$H NMR chemical shifts (δ) are reported in parts per million (ppm) relative to CHCl$_3$ and [D$_5$]DMSO as internal standards. Data are reported as follows: chemical shift, multiplicity (s=singlet, d=doublet, t=triplet, b=broadened, m=multiplet), coupling constants (J, given in Hz), integration. $^{13}$C NMR chemical shifts (δ) are reported in parts per million (ppm) relative to CDCl$_3$ and [D$_6$]DMSO as internal standards. The following experiments were used to record the resonances of the compounds: $^{1}$H-1D, $^{13}$C-1D NMR spectra and $^{13}$C-APT (attached proton test with a single J-evolution time of 1/145 s, spectra are processed such that quaternary and methylene groups have positive sign and methyl and methine groups negative sign). To resolve overlap of resonances and recover undetectable resonances in $^{1}$H and APT spectra, 2D-[$^{13}$C,$^{1}$H]-HSQC (heteronuclear single quantum coherence), 2D-[$^{13}$C,$^{1}$H]-HMBC (heteronuclear multiple bond correlation) and 2D-NOESY were recorded for some compounds. 1,3-Diarylpropane-1,3-diones are presented in the figures as diketones despite the fact that the enol form dominates the spectra.

Following compounds have been reported previously and synthesized according to published protocols[1]: anle138b, anle138c, anle145c, anle186b, anle253b, anle270, sery85, sery109, sery117, sery140, sery292b, sery315b, sery335b, sery345, sery363a, sery320c, sery383, sery392b.

Synthesis Example 1: Synthesis of Sery433, a Prodrug of anle138b to be Cleaved by IAP

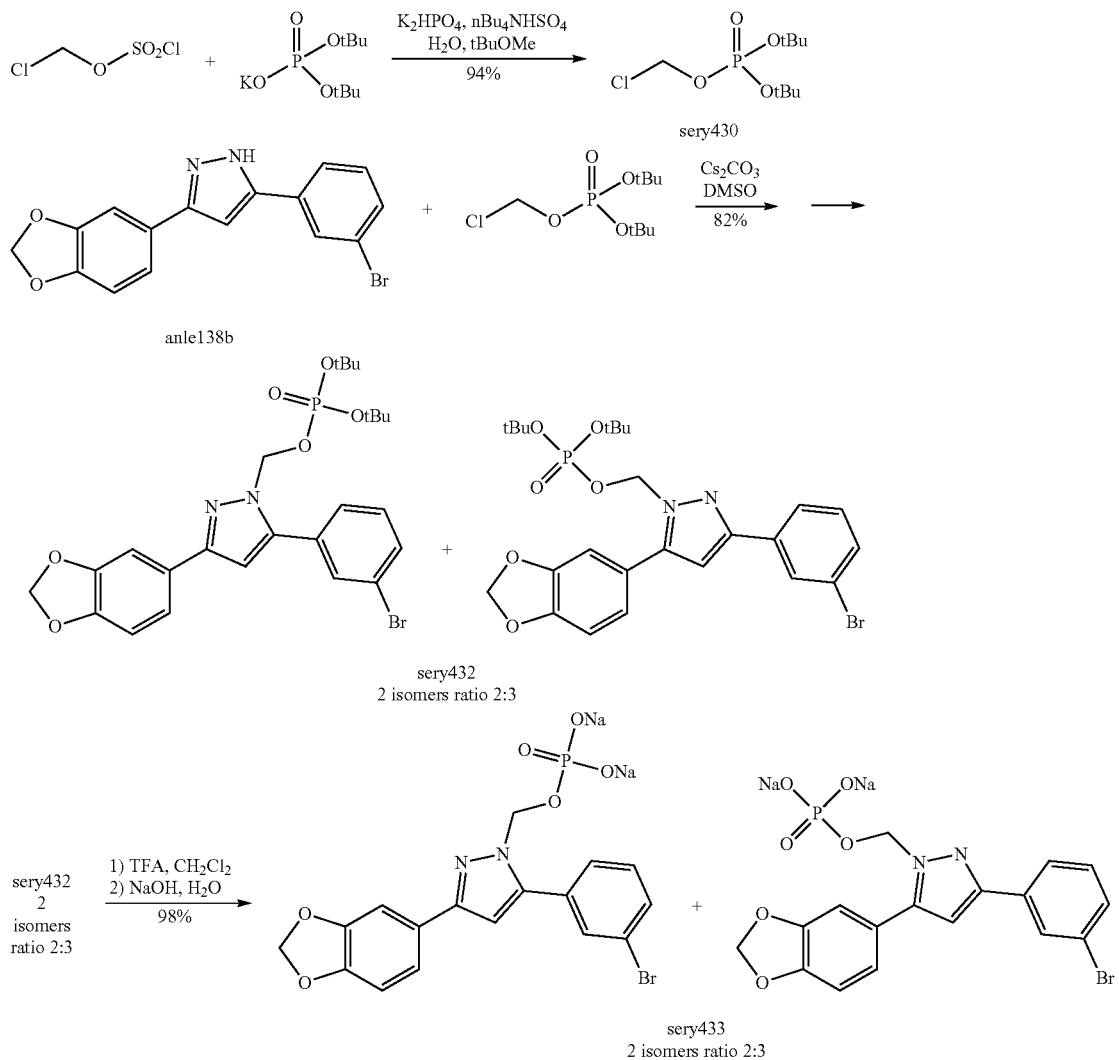

Di-Tert-Butyl Chloromethyl Phosphate (Sery430)

The compound sery433 was prepared according to published protocol (C. E. Müller, "Prodrug approaches for enhancing the bioavailability of drugs with low solubility" Chem. Biodiversity 6, 2071-2083 (2009); EP2133355A1 2009). To a mixture of di-tert-butyl potassium phosphate (35 g, 141 mmol), K$_2$HPO$_4$.3H$_2$O (127 g, 557 mmol), n-Bu$_4$NHSO$_4$ (4 g, 11 mmol), H$_2$O (125 ml) and tBuOMe (170 ml) a solution of chloromethyl chlorosulfate (35 g, 212 mmol) in tBuOMe (35 ml) was added dropwise with continuous vigorous stirring in 25 minutes at 0° C. After the addition was completed, stirring was continued for 2 hours at room temperature (the reaction mixture was cooled if internal temperature exceeded 30° C.). The reaction mixture was quenched with H₂O (350 ml) and tBuOMe (200 ml), the organic phase was separated, washed with aqueous 1M K₂HPO₄ solution (200 ml), water (200 ml), brine (50 ml) and dried over Na₂SO₄. After sodium sulfate was filtered, n-Bu₃N (3 ml) was added to the solution and the solution was concentrated under a reduced pressure to provide the product as oil (34.4 g, 94%). An additional portion of n-Bu₃N (3 mL) was added to the product in order to increase the stability during the storage in the freezer (−21° C.).
Sery432

To a mixture of anle138b (1) (25 g, 72.8 mmol), Cs₂CO₃ (35.6 g, 109 mmol) in DMSO (200 ml) di-tert-butyl chloromethyl phosphate (28.1 g, 109 mmol) was added in one portion. After stirring at room temperature for 5 hours the reaction mixture was diluted with water (1200 ml) and extracted with diethyl ether (500+200+100 ml). Combined organic fractions were washed with water (500 ml), brine (100 ml) and dried over Na₂SO₄. After sodium sulfate was filtered the solution was concentrated under a reduced pressure to provide the product as oil (49.5 g total, 40.8 g sery432, 82%, mixture of two isomers with ratio 2:3). The resulting product also contains 10.5% of sery430 and 7.1% Bu₃N based on ¹H NMR spectrum. The product was used in the next step without further purification. Sery432 is the mixture of isomers in ratio 2:3 CH NMR).
Sery433

To a cooled solution of sery432 (34.4 g, 60.9 mmol) in DCM (400 ml) TFA (23.5 ml) was added in 5 minutes with continuous vigorous stirring at 0° C. After 2 hours an additional portion of TFA (23 ml) was added and the reaction mixture was stirred at 0° C. for 8 hours. After dilution with cold toluene (300 ml) the reaction mixture was concentrated under a reduced pressure at 0° C., the residue was mixed with cold toluene (300 ml) and concentrated once again at 0° C. (DCM was evaporated at 50-100 mbar, TFA and toluene were evaporated with a high vacuum rotor evaporator). The resulting mixture was diluted with cold acetonitrile (300 ml), and stirred for one hour at 0° C. A white precipitate was filtered off and dried under reduced pressure to provide sery433 in acid form (31.0 g total, 29.0 g of sery433 in acid form and 2 g acetonitrile). To the crude sery433 in acid form 1M aqueous NaOH solution (129 ml, 129 mmol, 2 eq) and water (80 ml) were added, the resulting solution was filleted off (Millipore Express Plus filter) and filtrate was lyophilized to provide disodium salt sery433 (30.0 g, 99%, mixture of two isomers with ratio 2:3) as a white powder.

The two isomers of sery433, a phosphate derivative, are shown below.

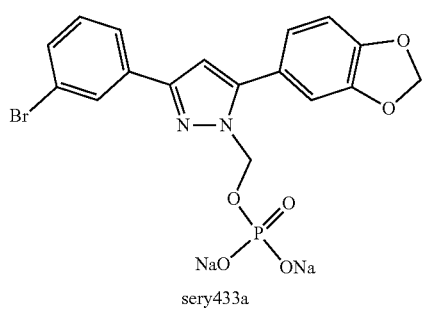

sery433a

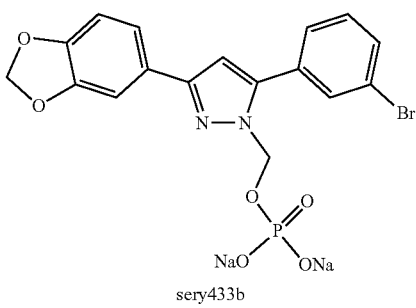

sery433b

Synthesis Example 2: Synthesis of anle423b (Prodrug of anle253b)

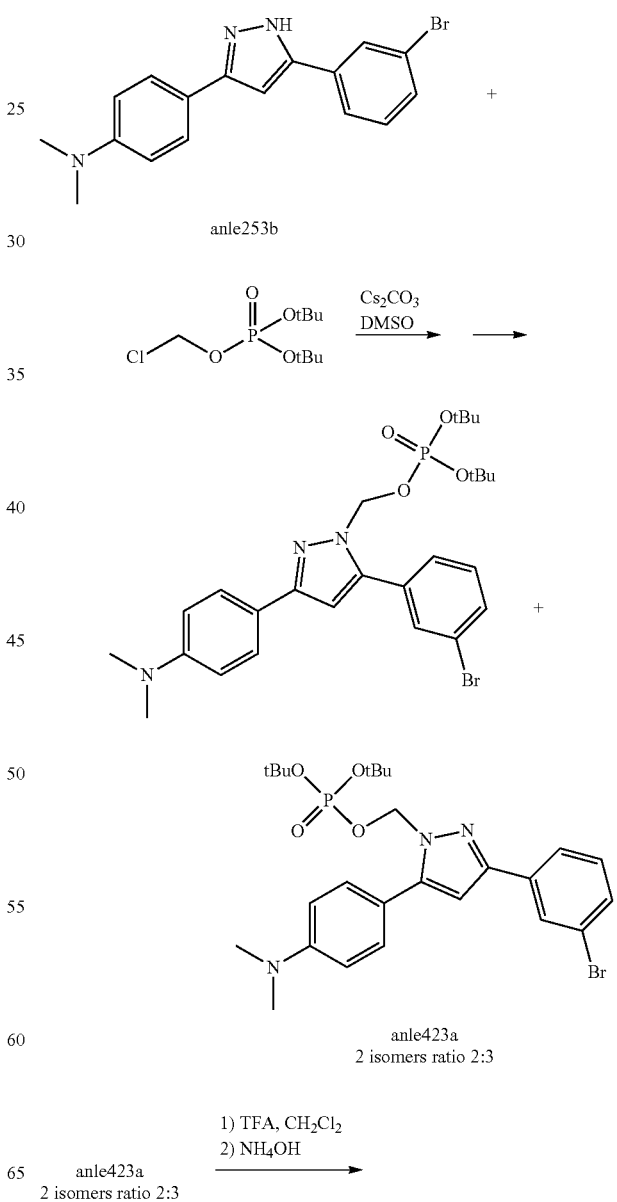

anle253b anle423a
2 isomers ratio 2:3

1) TFA, CH₂Cl₂
2) NH₄OH anle423a
2 isomers ratio 2:3

33
-continued

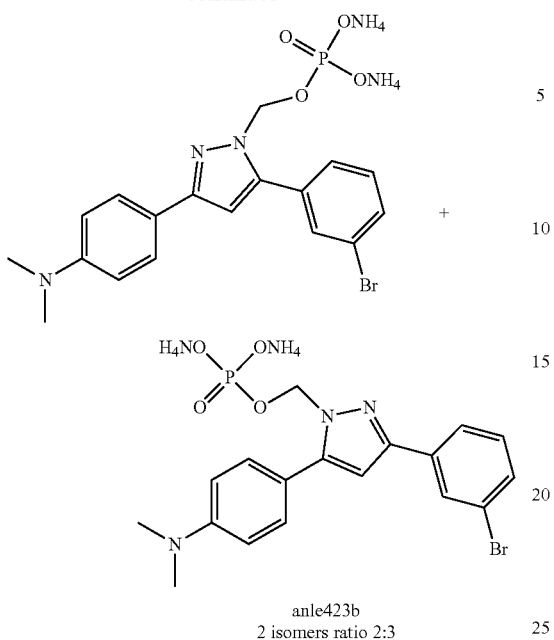

anle423b
2 isomers ratio 2:3

Anle423a

To a mixture of anle253b (500 mg, 1.46 mmol), Cs$_2$CO$_3$ (620 mg, 1.9 mmol) in DMSO (5 ml) di-tert-butyl chloromethyl phosphate (525 mg, 1.9 mmol) was added in one portion. After 15 hours of stirring at room temperature completeness of reaction was shown by Thin layer chromatography (TLC) (SiO$_2$, hexane:EtOAc=2:1, Rf educt 0.33, Rf product 0.18). The reaction mixture was diluted with water (30 ml) and extracted with ethyl acetate (2×15 ml). The combined extracts were washed with water (10 ml), brine (10 ml), dried over Na$_2$SO$_4$, and concentrated under reduced pressure to provide the product as oil (1.08 g). The product was used in next step without further purification.

Anle423b (Diammonium Salt)

To a cooled suspension of anle423a (1.08 g) in DCM (10 ml) TFA (2 ml) was added within 1 minute with continuous vigorous stirring at 0° C. and the reaction mixtures was stirred at 0° C. for 8 hours. The mixture was filtered (GHP 0.45 µm), diluted with toluene (10 ml), and concentrated under reduced pressure at 20° C., the residue was mixed with toluene (10 ml) and concentrated once again at 20° C. (DCM was evaporated at 50-100 mbar, TFA and toluene were evaporated with a high vacuum rotor evaporator). The resulting glassy viscous residue was triturated with cold acetone (30 ml), stirred for one hour at 0° C. A white precipitate was filtered off, washed with acetone (10 mL) and dried under reduced pressure to provide anle423b in acid form (448 mg, 0.99 mmol, 68%, mixture of two isomers with ratio anle423ba:anle423bb=3:2 according to 2D-NOESY NMR experiment) as a yellowish powder. To anle423b (diacid, 156 mg, 0.345 mmol) water (3 mL) and 25% NH$_4$OH (12.6M, 150 µL, 1.89 mmol) were added. The mixture was stirred until dissolution was complete, the resulting solution was frozen and lyophilized to provide diammonium salt anle423b (161 mg, 331 µmol, 96%, mixture of two isomers with ratio anle423ba:anle423bb=3:2) as a yellowish powder.

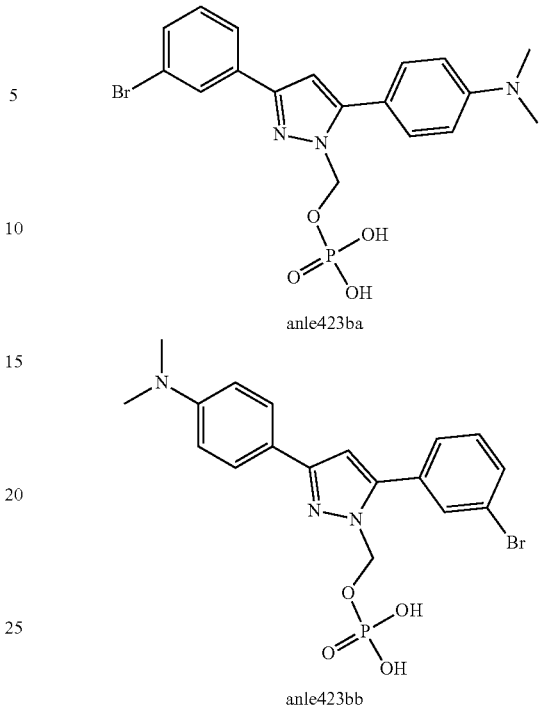

anle423ba anle423bb

Example 1

It has been reported that α-synuclein is expressed in melanoma (Matsuo Y & Kamitani T, 2010. Parkinson's disease-related protein, alpha-synuclein, in malignant melanoma. PLoS One 5(5):e10481.), and that its overexpression enhances the proliferation of B16 murine melanoma (Israeli E, et al. 2011. α-Synuclein expression selectively affects tumorigenesis in mice modeling Parkinson's disease. PLoS One 6(5):e19622.) However, scientific data regarding status and level of expression of the three major PD-related genes/proteins—α-synuclein/SNCA, LRRK2/PARK8, and parkin/PARK2—alongside one another in nevi and melanoma were not available. Therefore, to determine which of these three genes/proteins are expressed in the different stages of melanoma development and to what extent, we probed the same tissues of a nevus>melanoma progression tissue microarray (TMA) (Watson-Hurst K & Becker D 2006 The role of N-cadherin, MCAM and beta3 integrin in melanoma progression, proliferation, migration and invasion. Cancer Biol Ther 5(10):1375-1382) with antibody to the respective protein encoded by the gene SNCA, PARK8, or PARK2.

Figure 1:
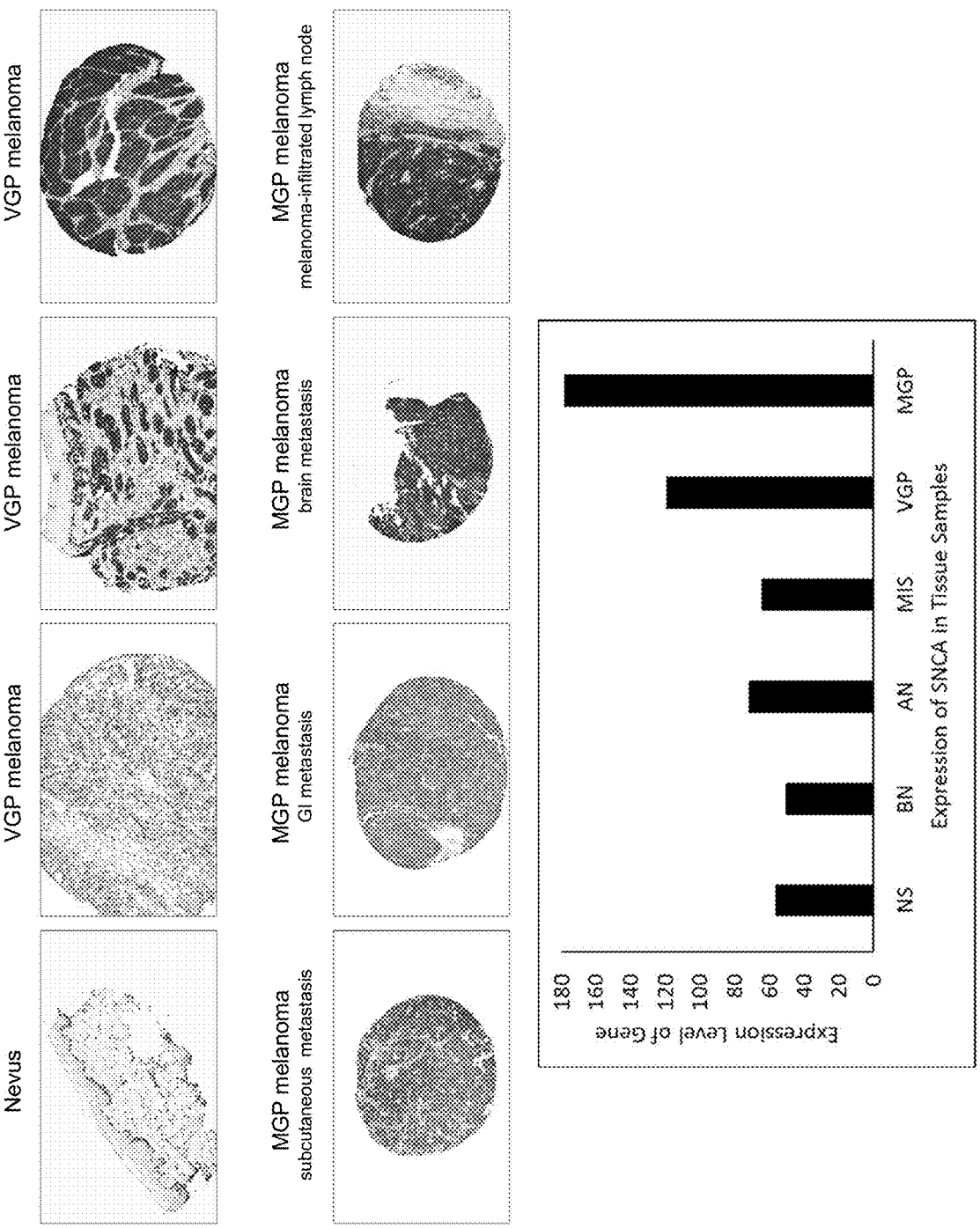
FIG. 1. Expression of α-synuclein/SNCA, LRRK2/PARK8, and Parkin/PARK2 in normal skin, and nevus and melanoma tissues.
Figure 1:
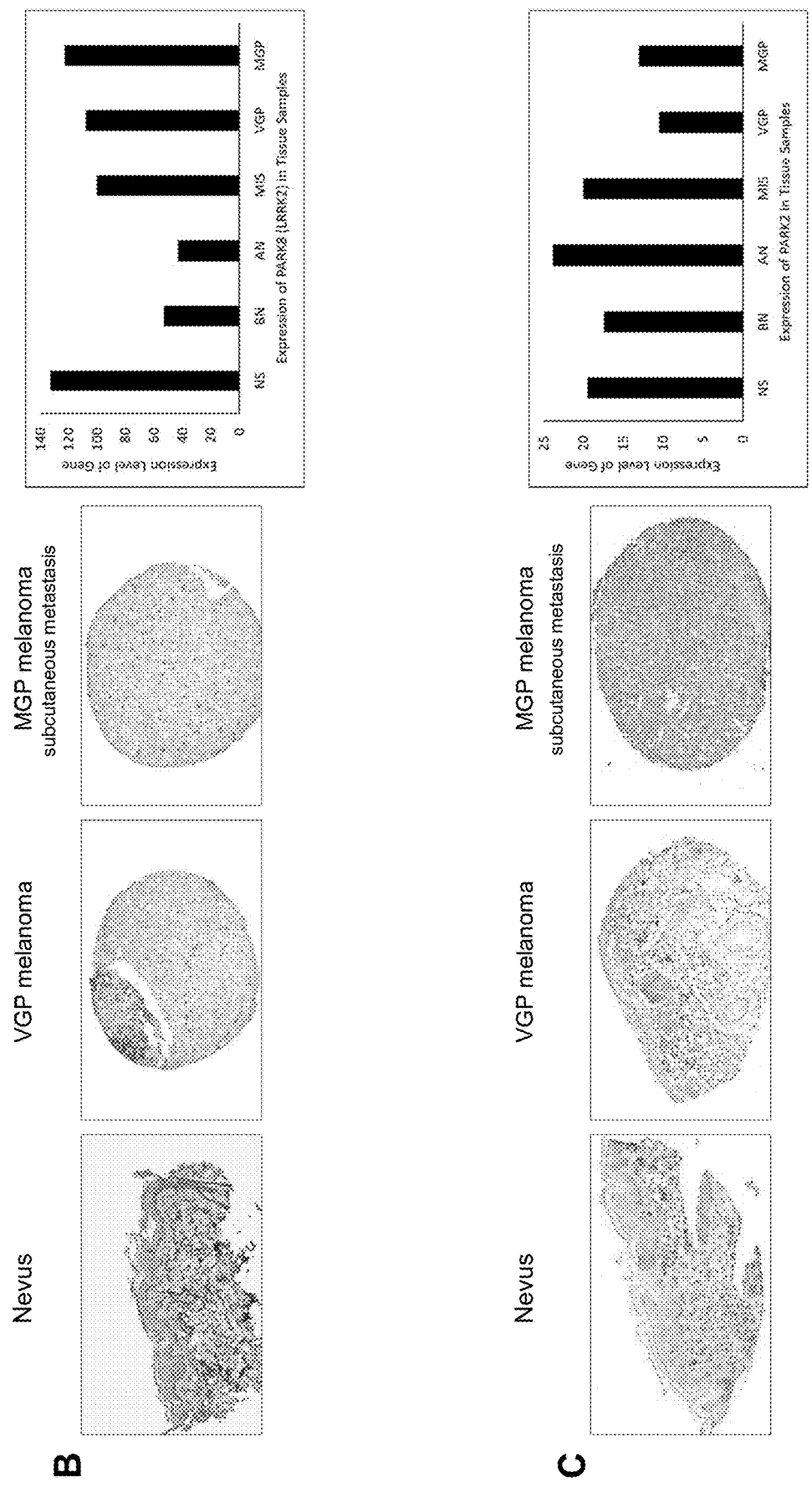

Depicted in FIG. 1A are examples of α-synuclein expression in TMA cores representing a nevus, three primary melanomas in the vertical growth phase (VGP melanoma), and four melanomas in the metastatic growth phase (MGP melanoma) obtained from different organ sides.

The results of this analysis revealed that α-synuclein was expressed primarily if not exclusively in melanoma cells in both VGP and MGP melanoma tissue cores, and in nevus tissue cores, it was expressed primarily in melanocytes residing along the epidermal-dermal junction; a finding that is in agreement with previously reported data (Matsuo Y & Kamitani T 2010. Parkinson's disease-related protein, alpha-synuclein, in malignant melanoma. PLoS One 5(5):e10481).

Since our analysis demonstrated strongest expression of α-synuclein in TMA cores representing advanced melanoma, we queried the Gene Expression Omnibus (GEO) DataSet GSE4587 from a whole-genome expression profiling study, we had previously conducted (Smith A P, Hoek K, & Becker D (2005). Whole-genome expression profiling of the melanoma progression pathway reveals marked molecular differences between nevi/melanoma in situ and advanced-stage melanomas. Cancer Biol Ther 4(9):1018-1029.), for the level of expression of the SNCA gene in tissues ranging from normal skin>MGP melanoma. Our data, obtained upon profiling of non-microdissected tissue samples representing normal skin (NS), benign nevi (BN), atypical nevi (AN), melanoma in situ (MIS), and VGP and MGP melanomas, suggest that SNCA is expressed at elevated levels in VGP and MGP melanomas compared with MIS and AN (FIG. 1A, Bar graph).

Probing the TMAs with an antibody to LRRK2 (FIG. 1B) showed that unlike α-synuclein, LRKK2 was not expressed in every melanoma cell in the VGP and MGP melanoma TMA cores, and only a few melanocytes in the nevus TMA cores showed expression of LRRK2 (FIG. 1B). Furthermore, while the PARK8 (LRRK2) expression profile (FIG. 1B, Bar graph) suggests that expression of the PARK8 (LRRK2) gene is higher in MIS and in VGP and MGP melanoma compared with BN and AN, its level of expression is highest in NS. Regarding Parkin (FIG. 1C), our TMA analysis showed that it is expressed primarily in melanoma cells, but unlike in the case of α-synuclein, not all of the melanoma TMA cores revealed expression of Parkin, and melanocytes in the nevus tissue cores showed relatively weak expression. Furthermore, our whole-genome expression profiling data (FIG. 1C, Bar graph) suggest that expression of the PARK2 gene is lower in VGP and MGP melanoma compared with NS, BN, AN, and MIS.

Example 2

Level of Expression, Subcellular Localization, and State of α-Synuclein Protein in VGP and MGP Melanoma Cells To determine the level of expression and subcellular localization of α-synuclein protein in cell lines derived from tumors representing advanced melanoma, we performed immunoblot analyses of the VGP melanoma cell line WM983-A, the three MGP melanoma cell lines WM983-B, SK-MEL-5, WM852, and the WM1158 melanoma cell line that was established from a superficial spreading melanoma in the radial growth phase (RGP)/VGP. As shown in FIG. 2A, the cell lines WM983-A and WM983-B, which were derived from a VGP and an MGP melanoma of the same patient, and the MGP melanoma cell line, SK-MEL-5, express high levels of α-synuclein. In comparison, the WM852 (MGP) and the WM1158 (RGP/VGP) melanoma cell lines contain lower levels of α-synuclein protein (FIG. 2A).

To determine the subcellular localization of α-synuclein in these cell lines, we performed immunofluorescence studies with two different antibodies to α-synuclein. Both antibodies detected α-synuclein throughout the nucleus and cytoplasm of the melanoma cell lines WM983-B (FIG. 2B and FIG. 6), WM983-A and SK-MEL-5 (FIG. 6), and at a low level in WM1158 (FIG. 6).

Previously, it has been reported that following phosphorylation at Ser129, α-synuclein is translocated to the cell surface (Lee B R, Matsuo Y, Cashikar A G, & Kamitani T (2013) Role of Ser129 phosphorylation of alpha-synuclein in melanoma cells. J Cell Sci 126(Pt 2):696-704.) from where, as shown in the case of SK-MEL-5 cells (Hansen C, et al. (2011) alpha-Synuclein propagates from mouse brain to grafted dopaminergic neurons and seeds aggregation in cultured human cells. J Clin Invest 121(2):715-725.), it is released and spreads, possibly by way of melanoma exosomes, to other cells where it is endocytosed.

Performing immunofluorescence analysis, we obtained evidence that α-synuclein is phosphorylated at Ser129 in WM983-B melanoma cells, (FIG. 2B). In addition, WM983-B melanoma whole-cell lysate, separated by size exclusion chromatography (SEC) (FIG. 7) followed by filter trap—dot blot analysis of the collected fractions with an anti-α-synuclein antibody, showed monomeric α-synuclein as well as its distribution in fractions of higher molecular weight species between 17 to 158 kD and >670 kD (FIG. 2C), indicating that in these cells, α-synuclein is oligomerized and also likely interacting with other proteins.

Example 3

Treatment of Melanoma Cells, Expressing High Levels of α-Synuclein, with Oligomer Modulators Affecting α-Synuclein, Causes Overt Changes in Melanoma Cell Morphology and Inhibits Melanoma Cell Proliferation To gain insights into the possible function(s) of the α-synuclein protein in advanced melanoma, we treated the melanoma cell lines WM983-A, WM983-B, SK-MEL-5, WM852, and WM1158 with a panel of diphenyl-pyrazole (DPP) compounds. The DPP scaffold, identified from the small molecule DIVERSet libraries (Chem-Bridge Corp., San Diego, Calif.) by way of inhibition of prion protein aggregation, followed by medicinal chemistry optimization of DPP compounds, led to the identification of anle138b and anle138c (Wagner et al. Acta Neuropathol. 2013 June; 125(6):795-813). Neither of these two compounds binds to α-synuclein monomers (Deeg et al., Biochim Biophys Acta. 2015 1850(9):1884-90), but they both reduce the formation of toxic oligomers and therefore, also indirectly fibrils.

From an initial screen of sixteen compounds from the DPP library, we found that anle138b, sery334b, anle138c, and anle253b significantly affected the high-level α-synuclein expressing cell lines WM983-B. The strongest and most rapid effect was observed for anle138b.

To assess the possible impact of anle138b as well as anle138c on the different melanoma cell lines, WM983-A, WM983-B and SK-MEL-5, we treated them with increasing doses of either compound, dissolved in dimethyl sulfoxide (DMSO), and added to serum-free culture medium. The two melanoma cell lines WM983-B and SK-MEL-5, expressing high levels of α-synuclein, demonstrated, time- and dose-dependently, major morphological changes manifested first by the formation of cell clusters, followed by increasing detachment from the surface of the tissue culture dish. FIG. 3A shows representative images of WM983-B and SK-MEL-5 melanoma cells treated for 48 hr with a single dose of 10 μM of either anle138b or anle138c. We also observed that treatment with anle138b caused a more rapid morphological change than anle138c. To determine whether the effect of the two anle compounds was related to the amount of α-synuclein produced by the cells, we compared the proliferation of the (VGP) WM983-A high-level and the (RGP/VGP) WM1158 low-level α-synuclein-producing melanoma cells over a period of 96 hr, with replenishment of each anle compound at 48 hr (FIGS. 8A and B). The morphological changes in the WM983-A and WM1158 cells lines did not occur as rapidly as in the case of the MGP melanoma cell lines, WM983-B and SK-MEL-5. However, residual WM983-A cells, which remained attached to the tissue culture dish at 96 hr, were not able to proliferate again after removal of the anle138b-containing culture medium, followed by rinsing three-times with fresh medium and subsequent incubation in serum-free medium. In contrast, the WM1158 cells did not show a significantly altered morphology by the treatment with anle138b or anle138c, showed reduced proliferation only after 48 hr, and were able to recover proliferation normally following removal of anle138b at 96 hr and addition of fresh culture medium containing serum.

Since the morphological changes in the high-level α-synuclein-expressing melanoma cells occurred more rapidly following addition of anle138b than anle138c, we performed the subsequent studies primarily with anle138b, which has no anti-oxidative effects and does not impair the expression or degradation of α-synuclein, and unlike anle138c, has an excellent oral bioavailability and blood-brain-barrier penetration (Wagner et al. Acta Neuropathol. 2013 June; 125 (6):795-813).

To compare how rapidly anle138b affected the proliferation of melanoma cells, expressing α-synuclein at a high level, we treated the melanoma cell lines, WM983-A (VGP) and WM983-B (MGP), for 24, 48 or 72 hr with 10 μM of anle138b, with replenishment of the compound (10 μM) at 48 hr. As shown in FIG. 3B, in as little as 24 hr, a single dose of 10 μM of anle138b inhibited the proliferation of both cell lines to a significant extent.

Example 4

Anle138b Treatment of Melanoma Cells Damages their Plasma Membrane, Disrupts their Mitochondrial Membrane Potential, and Dysregulates Autophagy To determine the effect of increasing doses of anle138b on melanoma cell viability and whether it is cytotoxic to the cells and thus, compromises their plasma membrane integrity, we performed a lactate dehydrogenase (LDH) cytotoxicity assay of culture supernatants, collected from WM983-B as well as WM852 melanoma cells that were treated for 96 hr with increasing doses of anle138b, with replenishment of an equivalent dose of the compound at 48 hr. As shown in FIG. 4A, the high-level α-synuclein-expressing WM983-B cells showed strong killing that reached a maximum at a 10 μM dose of anle138b, possibly due to its low solubility above this dose in serum-free medium. In comparison, the number of cells killed in response to anle138b treatment was significantly lower in the case of the low-level α-synuclein-expressing WM852 cells (FIG. 4A).

Although the morphological changes in the WM983-A, WM983-B, and SK-MEL-5 melanoma cell lines following addition of anle138b occurred quite rapidly, they were not indicative of the cells undergoing apoptosis. This observation was supported by the fact that neither the anle138b- nor the anle138c-treated cells exhibited abnormal condensation and fragmentation of chromatin, nor were they positive for cleaved caspase 3. However, as shown in FIG. 4B, the mitochondrial membrane potential of WM983-B and SK-MEL-5 melanoma cells was significantly reduced as early as 24 hr following addition of a single 10 μM dose of anle138b, while the low-level α-synuclein-expressing WM1158 cells started to show some reduction in mitochondrial membrane potential only after 48 hr of anle138b treatment. Differential interference contrast (DIC) images of the morphology of the anle138b-treated WM983-B, SK-MEL-5, and WM1158 melanoma cells from the same panels are shown in FIG. 9.

We observed a clear effect of the anle compounds on the autophagy pathway of the melanoma cells. WM983-B cells, treated with anle138b, demonstrated prominent punctuate upregulation of the autophagosome marker, microtubule-associated protein 1 light chain 3B (LC3), in about 60% of the cells still attached at 24 hr and in 95% of the cells remaining on the cell culture dish at 48 hr, whereas WM983-B cells that had received DMSO only showed less than 1% cells with LC3 puncta at 96 hr (FIG. 4C). Following addition of anle138c, the effect was seen later with levels of 8% at 24 hr and 78% after 96 hr. Similar levels of punctuate LC3 loci were also observed for the SK-MEL-5 melanoma cells upon treatment with anle138b (FIG. 4C), and even higher levels with anle138c.

To determine how soon following addition of anle138b to high-level α-synuclein-expressing melanoma cells autophagy was dysregulated, and whether a dose below 10 μM of anle138b would suffice, we treated WM983-B melanoma cells with 7.5 μM of anle138b for 24, 48 or 72 hr, with replenishment of an equivalent dose of the compound at 48 hr. Probing WM983-B melanoma whole-cell lysates with an antibody to the protein, p62/SQSTM1, which is required for the aggregation of ubiquitinylated proteins and their clearance via autophagy, showed that anle138b treatment for 24 hr did not lead to an increase in p62/SQSTM1 expression (FIG. 4D, lane 1). However, after 48 and 72 hr of anle138b treatment (FIG. 4D, lanes 2, 3), the level of expression of this autophagy cargo adaptor protein was noticeably elevated compared with WM983-B cells that had received DMSO only (FIG. 4D, lane 4).

Example 5

Anle138b Administered, Systemically, to Nude Mice Bearing High-Level α-Synuclein-Expressing Human Melanoma Xenografts, Reaches the Tumors and Affects their Morphology and Autophagy To determine whether the DPP compound, anle138b, when administered systemically to human MGP melanoma cells grown as subcutaneous tumors in nude mice, would reach the tumors, we performed the following study. A nude mouse, bearing high-level α-synuclein-expressing (MGP) WM983-B human melanoma xenografts on its lower right and on its lower left dorsal side, received, for seven days, food pellets mixed with anle138b. A second nude mouse, also bearing WM983-B tumors on its lower right as well as on its lower left dorsal side, received, for seven days, the same type of food pellets not containing anle138b. After the mice were sacrificed, we performed the following analyses on the post-mortem resected and thereafter, cryopreserved tumors.

Figure 10A:
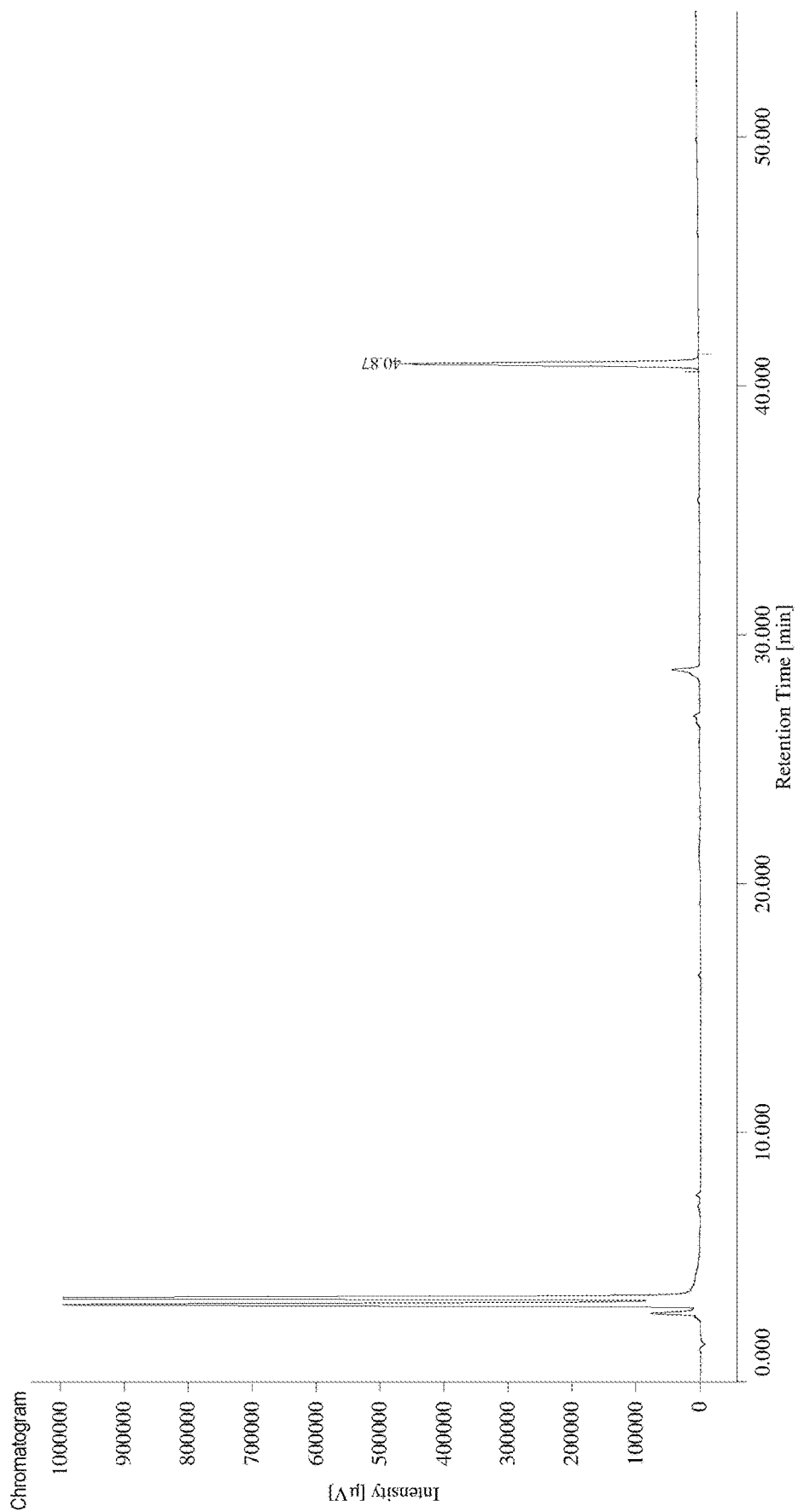
Figure 10B:
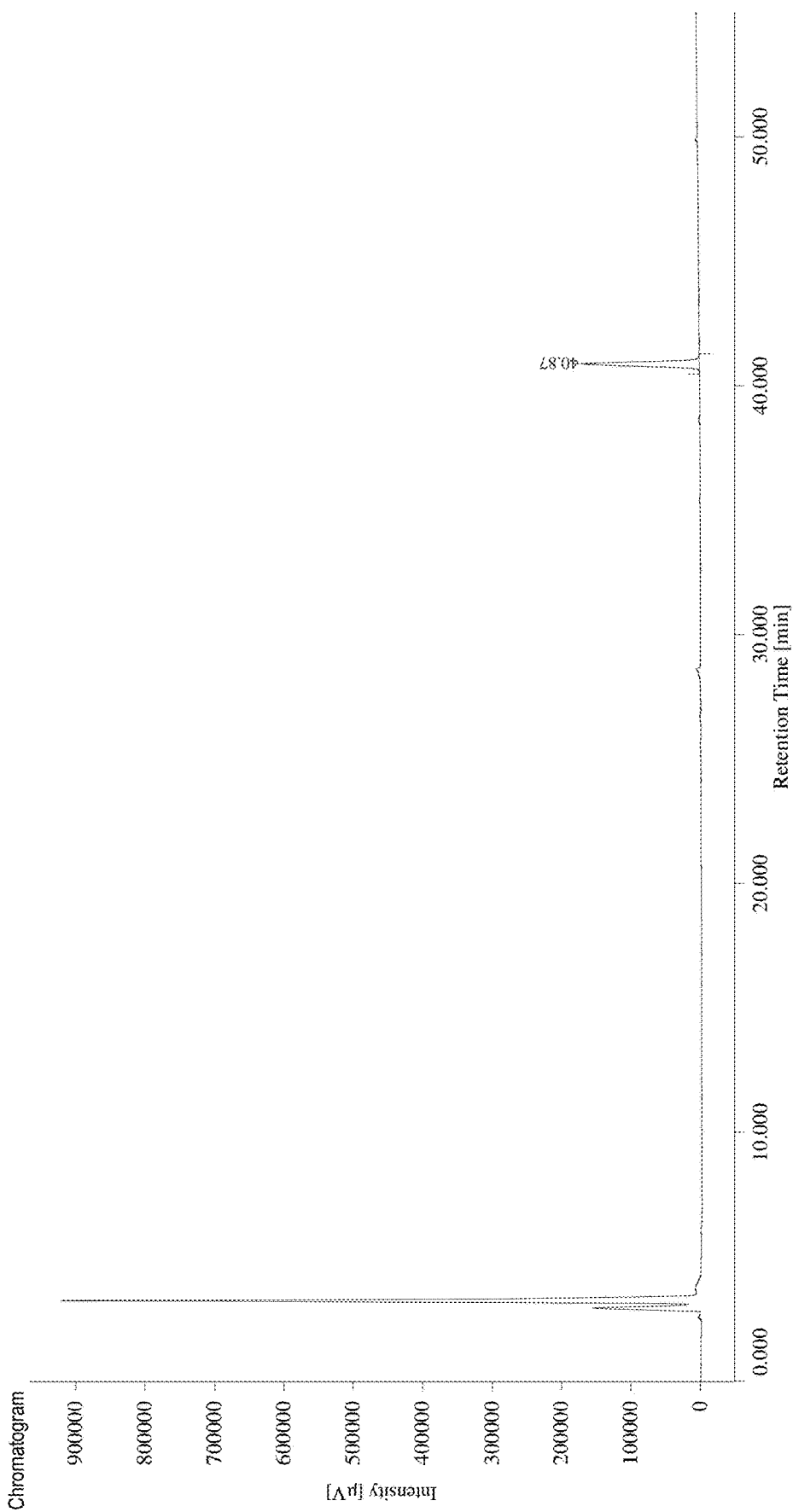
Figure 10C:
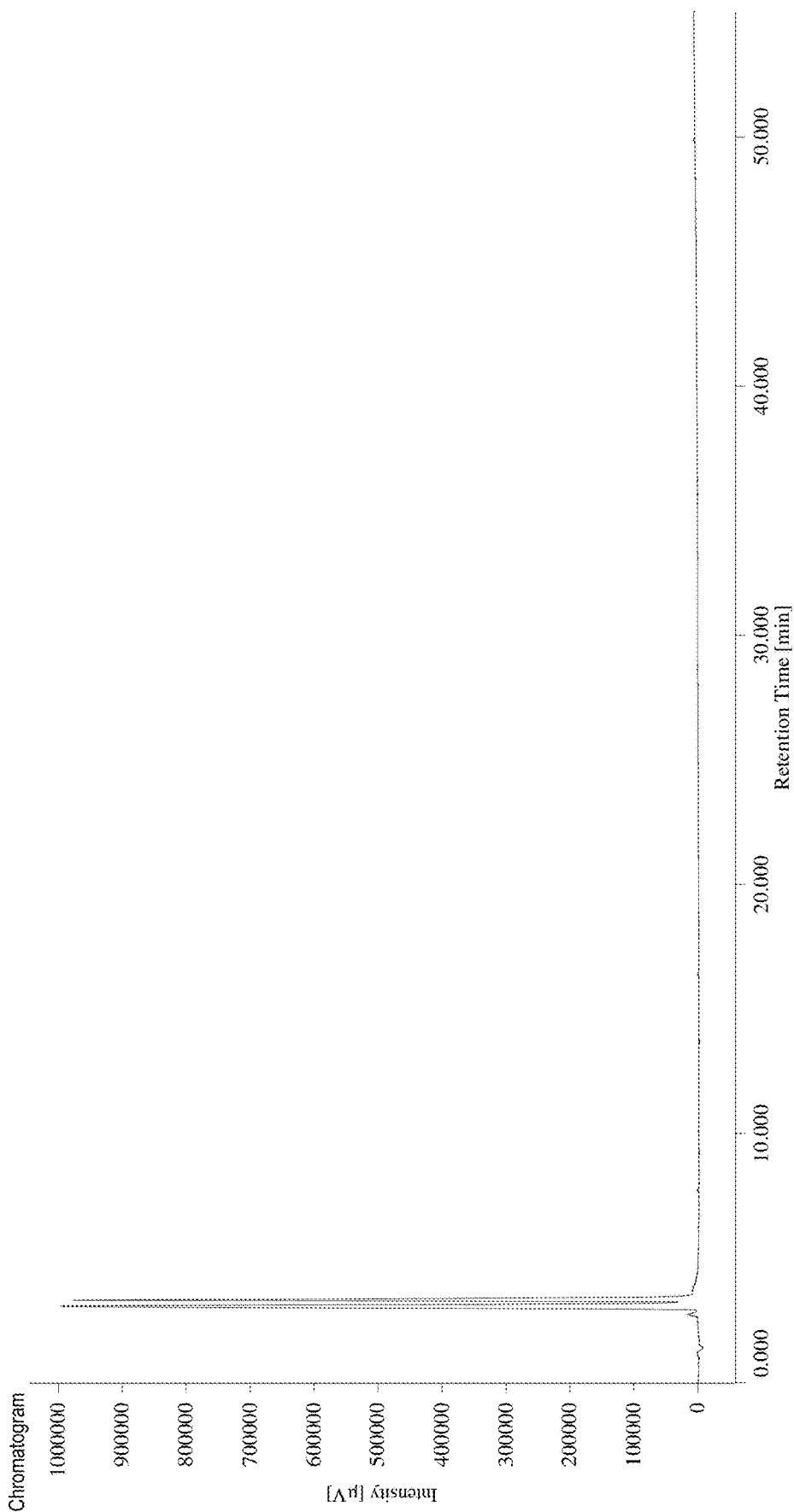
Figure 10D:
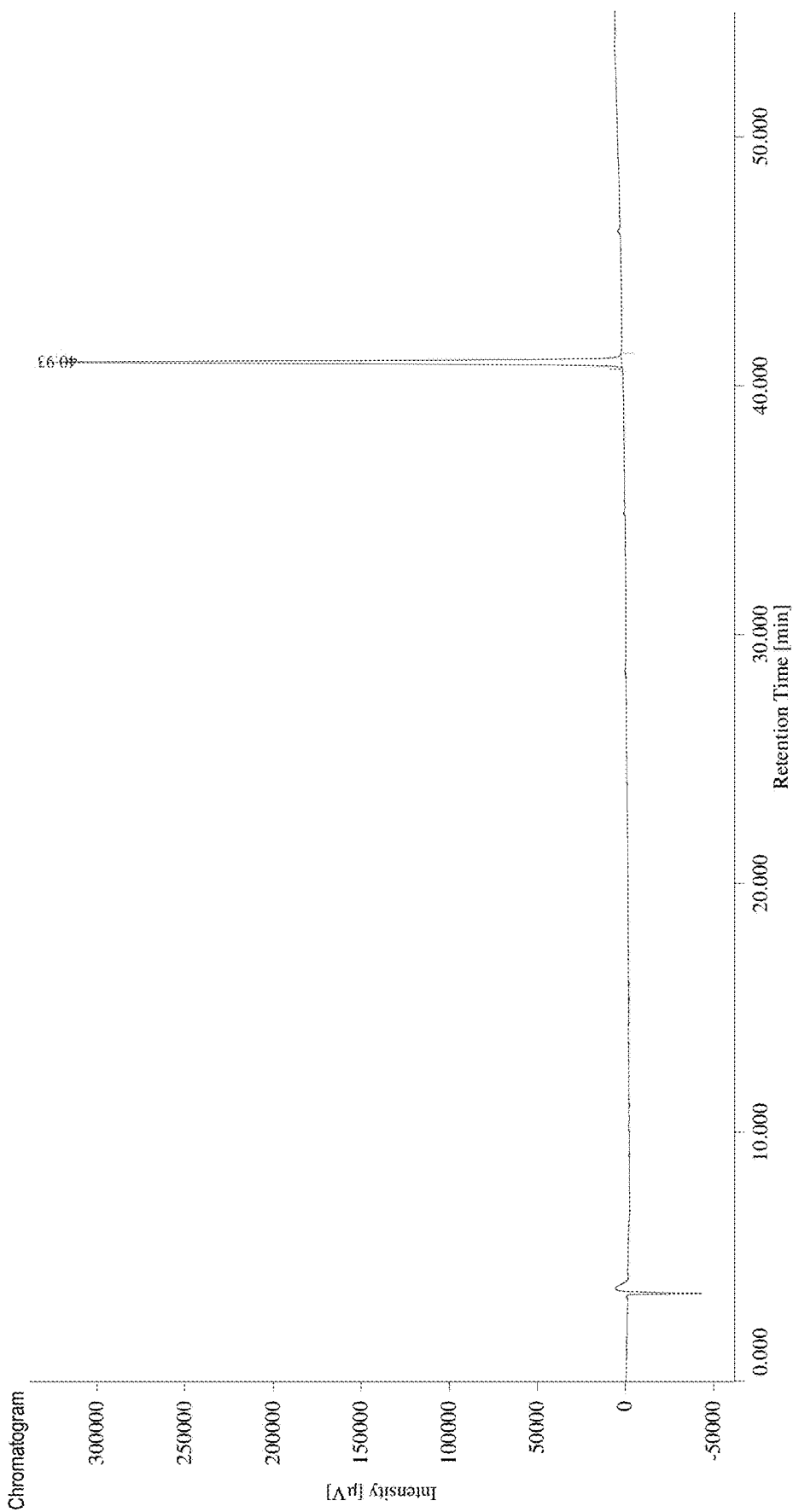

Firstly, the results of our pharmacokinetic (PK) analysis of the resected tumors showed that anle138b was present at a level of 125 μM in the tumor (weight of tumor—57 mg) resected from the right dorsal side (FIG. 10A), and at a level of 110 μM in the tumor (weight of tumor—218 mg) resected from the left dorsal side (FIG. 10B) of the WM983-B human melanoma xenograft-bearing animal that had received food pellets mixed with anle138b. In contrast, anle138b was not detected in a tumor resected from the WM983-B human melanoma xenograft-bearing mouse that had received food pellets without anle138b (FIG. 10C). Secondly, hematoxylin and eosin (H&E) staining of tissue sections, prepared from one of the WM983-B human melanoma xenografts that had been resected from the animal that had received the food pellets mixed with anle138b (FIGS. 5C and D), showed that the morphology of these tumor cells, arranged in a scattered pattern with focally pronounced disturbances in the tissue's architecture, differed from the morphology of the tumor cells in a WM983 control tumor that did not contain anle138b (FIGS. 5A and B). Thirdly, probed with anti-LC3 antibody, tissue sections from a WM983-B human melanoma xenograft, resected from the animal that had received anle138b-containing food pellets, showed more LC3-positive cells (FIG. 5F) compared with anti-LC3 antibody-probed tissue sections prepared from one of the WM983-B human melanoma xenograft control tumors that did not contain anle138b (FIG. 5E).

Discussion

Little if any information is yet available regarding the underlying mechanisms that are the reason for the epidemiological link between PD, which affects an estimated 7 to 10 million people worldwide and advanced melanoma, the most aggressive type of skin cancer that accounts for 75% of all skin cancer-related death. Since it has been ruled out that genetic factors link these two diseases, we explored the possibility that the association could be α-synuclein, LRRK2, or Parkin, which are the key regulators of PD.

We provide tissue-based evidence that unlike LRRK2 and Parkin, it is α-synuclein that is expressed almost exclusively in melanoma cells. Interestingly, the Gene Expression Omnibus (GEO) profiles of the NCI-60 cancer cell line panel also show that compared with cell lines derived from cancer tissue from nine different origin types (breast, central nervous system, colon, leukemia, melanoma, non-small cell lung, ovarian, prostate, renal), malignant melanoma cell lines have overall the highest level of SNCA expression (NCBI-Geo DataSet Browser (GDS 4296[ACCN]snca). Likewise, information available in the Human Protein Atlas (http://www.proteinatlas.org) shows strong expression of α-synuclein in advanced melanoma compared with other malignancies, including other types of skin cancer.

Mutations in the SNCA gene are rare while mutations in the PARK8 gene, which encodes the 2527 amino acid-long multi-domain LRRK2 protein, are the most common cause of autosomal dominant PD. The data of our nevus>advanced melanoma TMA analysis demonstrated that LRRK2 is expressed at various levels in some but not in all nevocytes and melanoma cells. Furthermore, in some of the VGP and MGP melanoma TMA cores, we also detected LRRK2 expression in cells interspersing the tumor cells. Mutations in the PARK2 gene, which encodes the E3-ubiquitin ligase Parkin, are the most frequent genetic cause of autosomal recessive juvenile PD. Like in the case of α-synuclein, our TMA analysis showed that Parkin is expressed in melanoma cells. However, compared with α-synuclein, the level of Parkin expression in the VGP and MGP melanoma TMA cores was significantly lower and not all of the melanoma TMA cores showed expression of Parkin, which supports the suggestion that in melanoma, PARK2 is a tumor suppressor (Hu H H, et al. 2016. PARKIN Inactivation Links Parkinson's Disease to Melanoma. J Natl Cancer Inst 108(3)). Two other genes, which have been linked to PD, are DJ-1 and ATP13A2. We did not determine the status of expression of DJ-1 in tissues ranging from nevi>advanced melanoma, but a histopathologic study has shown that in cutaneous melanoma, cytoplasmic expression of DJ-1 is decreased (Hintsala H R, Soini Y, Haapasaari K M, & Karihtala P 2015. Dysregulation of redox-state-regulating enzymes in melanocytic skin tumours and the surrounding microenvironment. Histopathology 67(3):348-357), while in the serum of patients with metastatic uveal melanoma it is elevated (Chen L L, et al. 2015. DJ-1: a promising marker in metastatic uveal melanoma. J Cancer Res Clin Oncol 141(2):315-321. Pardo M, et al. 2006). The characterization of the invasion phenotype of uveal melanoma tumour cells shows the presence of MUC18 and HMG-1 metastasis markers and leads to the identification of DJ-1 as a potential serum biomarker. Int J Cancer 119(5):1014-1022). To date, it is not known whether ATP13A2 plays a role in melanoma but in light of its putative interplay with α-synuclein (Lopes da Fonseca T & Outeiro T F 2014. ATP13A2 and Alpha-synuclein: a Metal Taste in Autophagy. Exp Neurobiol 23(4):314-323), it is noteworthy that the ATP13A2-specific DataSet from our previously conducted whole-genome expression profiling study indicates that like in the case of α-synuclein, the ATP13A2 gene is upregulated with progression from nevi>melanoma.

Gaining important insights into pertinent pro-survival mechanisms and pathways for advanced melanoma constitutes one of the essential tasks to finding effective therapies for patients with this disease. The novel and important finding, presented herein, is that treatment of high-level α-synuclein-expressing VGP and MGP melanoma cells with the α-synuclein and prion protein oligomer modulators represented by the formula (E), particularly anle138b or anle138c, leads to rapid melanoma cell death due to plasma membrane damage, a severe reduction in mitochondrial membrane potential, and a major dysregulation of autophagy. Furthermore, with a view towards potential future clinical applications for advanced melanoma, we provide, in the setting of a preclinical human melanoma xenograft study, first evidence that systemically administered compounds represented by the formula (E), particularly anle138b, not only reach the tumor, but also are present at high levels in the tumor cells, and that they affect their morphology and autophagy.

Our finding that treatment of high-level α-synuclein-expressing melanoma cells with anle138b leads to dysregulation of melanoma cell autophagy vis-à-vis the finding that in a mouse model of tauopathies, anle138b treatment did not change the level of the autophagy markers, LC3 and p62/SQSTM1 (Wagner J, et al. 2015. Reducing tau aggregates with anle138b delays disease progression in a mouse model of tauopathies. Acta Neuropathol 130(5):619-631) suggests that the biologic consequence(s) of treatment with anle138b is cell type-specific. This specificity may be linked to the deleterious effects α-synuclein has on neurons in a synucleinopathy such as PD; whereas in an aggressive malignancy such as advanced melanoma, high-level expression of α-synuclein is not only beneficial to the cells' survival, but possibly also promotes, probably by way of spreading via melanoma exosomes (Hansen C, et al. 2011. alpha-Synuclein propagates from mouse brain to grafted dopaminergic neurons and seeds aggregation in cultured human cells. J Clin Invest 121(2):715-725.), the formation and growth of melanoma brain metastases to which this disease is particularly prone.

By now, it is well established that in normal cells, autophagy has a protective role while in cancer it has a dual role—as a suppressor in the early stages of cancer development, and as a facilitator/promoter in the advanced stages (Galluzzi L, et al. 2015. Autophagy in malignant transformation and cancer progression. EMBO J 34(7):856-880. White E 2015. The role for autophagy in cancer. J Clin Invest 125(1):42-46. White E 2012. Deconvoluting the context-dependent role for autophagy in cancer. Nat Rev Cancer 12(6):401-410. Kroemer G & Levine B 2008. Autophagic cell death: the story of a misnomer. Nat Rev Mol Cell Biol 9(12):1004-1010). Thus far, little is known to what extent autophagy plays a role in nevus>melanoma progression, and in melanoma in its early versus advanced stages. However, it has been reported that RGP, VGP and in particular MGP melanomas express significantly lower levels of LC3 than nevi (Miracco C, et al. 2010. Beclin 1 and LC3 autophagic gene expression in cutaneous melanocytic lesions. Hum Pathol 41(4):503-512), and that median p62/SQSTM1 expression levels are lower in American Joint Committee on Cancer (AJCC) stage III/IV than in AJCC stage I/II melanomas (Ellis R A, et al. 2014. Prognostic impact of p62 expression in cutaneous malignant melanoma. J Invest Dermatol 134(5):1476-1478). This is in concordance with our finding that the two MGP melanoma cell lines, WM983-B and SK-MEL-5 that had received DMSO only, showed an LC3-positive phagosome signal in less than 1% of the cells, and that the level of p62/SQSTM1 expression in the DMSO-treated WM983-B cells was low. On the other hand, recent and increasing evidence, obtained primarily in the context of melanoma—BRAF inhibitor resistance studies, suggests that autophagy is a pertinent survival mechanism for advanced melanoma (Xie X, Koh J Y, Price S, White E, & Mehnert J M 2015. Atg7 Overcomes Senescence and Promotes Growth of BrafV600E-Driven Melanoma. Cancer Discov 5(4):410-423. Goodall M L, et al. 2014. Development of potent autophagy inhibitors that sensitize oncogenic BRAF V600E mutant melanoma tumor cells to vemurafenib. Autophagy 10(6):1120-1136. Ma X H, et al. 2014. Targeting ER stress-induced autophagy overcomes BRAF inhibitor resistance in melanoma. J Clin Invest 124(3):1406-1417. Maes H & Agostinis P 2014. Autophagy and mitophagy interplay in melanoma progression. Mitochondrion 19 Pt A:58-68. Maddodi N, et al. 2010. Induction of autophagy and inhibition of melanoma growth in vitro and in vivo by hyperactivation of oncogenic BRAF. J Invest Dermatol 130(6):1657-1667).

In summary, our findings presented herein, provide first evidence that α-synuclein, which in PD exerts severe toxic functions, promotes and thereby is highly beneficial to the survival of melanoma in its advanced stages. In addition, our data suggest that dysregulating autophagy in VGP and MGP melanoma cells by way of interfering with the aggregation of α-synuclein might be a novel and powerful approach to a triple combination therapy, encompassing a compound represented by the formula (E), such as anle138b, a small-molecule inhibitor targeting a key regulator of advanced melanoma, and deployment of a potent immunostimulatory antibody.

Materials and Methods
Melanoma Cell Lines, TMAs, GEO DataSets

The human melanoma cell lines WM983-A, WM983-B, WM852, and WM1158 were propagated in vitro as described (Becker D, Meier C B, & Herlyn M 1989. Proliferation of human malignant melanomas is inhibited by antisense oligodeoxynucleotides targeted against basic fibroblast growth factor. EMBO J 8(12):3685-3691). The human melanoma cell line SK-MEL-5, purchased from CLS Cell Lines Service GmbH (Eppelheim, Germany), was propagated in Eagle's Minimum Essential Medium (MEM) supplemented with non-essential amino acids, sodium pyruvate, and 10% fetal bovine serum (FBS).

Following antigen retrieval and prior staining of test TMAs to determine the optimal dilution (signal to noise performance) for each antibody, tissue cores of a nevus>melanoma progression TMA (Watson-Hurst K & Becker D 2006. The role of N-cadherin, MCAM and beta3 integrin in melanoma progression, proliferation, migration and invasion. Cancer Biol Ther 5(10):1375-1382) were probed by standard immunohistochemistry with antibody to α-synuclein [MJFR1], LRRK2 [MJFF2] or Parkin (Abcam, Cambridge, Mass., USA), followed by scanning of the TMA slides with an Aperio ScanScope (Leica Microsystems Inc., Buffalo Grove, Ill., USA) to generate digital images of the antibody-probed tissue cores.

From the DataSets of our whole-genome expression profiling study (Smith A P, Hoek K, & Becker D (2005) Whole-genome expression profiling of the melanoma progression pathway reveals marked molecular differences between nevi/melanoma in situ and advanced-stage melanomas. Cancer Biol Ther 4(9):1018-1029.), we previously deposited in the NCBI GEO database (DataSet GSE4587), we sourced the expression level of SNCA from the mean of the values listed for NS (n=2), AN (n=2), MIS (n=2), VGP melanoma (n=2), MGP melanoma (n=5) under profile GDS1989/236081, of PARK8 (LRRK2) under profile GDS1989/229584, and of PARK2 under profile GDS1989/207058.

Immunoblot Analysis

For the analysis of α-synuclein protein expression, whole-cell lysates were separated on 12% sodium dodecyl sulfate-polyacrylamide gels (SDS-PAGE), transferred onto polyvinylidene difluoride (PVDF) membrane, cross linked by a 30 min treatment at room temperature with 0.4% paraformaldehyde (PFA) in phosphate-buffered saline (PBS), blocked with 5% powdered milk, probed with antibody against α-synuclein [MJFR1] (Abcam), followed by incubation with a horseradish peroxidase-conjugated (HPR) secondary antibody and SuperSignal West Pico chemiluminescent substrate (Thermo Fisher Scientific Inc., Schwerte, Germany). Protein loading was determined by secondary probing with an anti-actin [ab1801] antibody (Abcam).

For the analysis of p62/SQSTM1 protein expression, WM983-B melanoma whole-cell lysates were separated on 12% SDS-PAGE, transferred onto nitrocellulose membrane, blocked with 3% bovine serum albumin (BSA), probed with an anti-p62/SQSTM1 antibody (Cell Signaling Technology, Inc. Danvers, Mass., USA), followed by incubation with a corresponding HPR-conjugated secondary antibody and chemiluminescent substrate (EMD Millipore, Billerica, Mass., USA). Protein loading was determined by secondary probing with an anti-GAPDH antibody (Thermo Fisher Scientific Inc.).

SEC—Filter Trap Assay

WM983-B melanoma cells were lysed in PBS containing 0.5% Triton X-100 and protease inhibitors. The protein lysate (2.2 mg/0.5 ml) was filtered through a 0.45 μm centrifuge tube filter prior to loading onto a Superose 6 10/300GL column (GE Healthcare Bio-Sciences, Pittsburgh, USA) connected to an ÄKTApurifier 10 (GE Healthcare Life Sciences, Uppsala, Sweden). The collected fractions were placed for 10 min in a 95° C. water bath and thereafter, the entire volume of every collected fraction was loaded onto nitrocellulose membranes by way of a dot blot vacuum system. After blocking in Tris-buffered saline-Tween 20 (TBST) containing 5% nonfat dry milk, the membranes were probed with a mouse monoclonal anti-α-synuclein [Syn-1] antibody (BD Biosciences, San Jose, Calif., USA), followed by incubation with a corresponding HRP-conjugated secondary antibody and chemiluminescent substrate (EMD Millipore). The SEC—filter trap assay was repeated twice.

Anle138b and anle138c Inhibitor Treatment, and Melanoma Cell Proliferation Analysis 10 or 30 mM stock solutions of anle138b or anle138c were made in DMSO. Since anle138b as well as anle138c bind strongly to FBS, melanoma cells, plated for 24 hr in tissue-culture medium containing 10% FBS, were rinsed three times with serum-free medium prior to addition of anle138b, anle138c, or an equivalent volume of DMSO only in serum-free medium. Forty-eight hours later, the cell culture medium was removed, followed by addition of an equivalent dose of anle138b or anle138c, or DMSO only in serum-free culture medium. Since the WM1158 (RGP/VGP) melanoma cells do not proliferate well in serum-free culture medium, 20 ng/ml of recombinant human basic fibroblast growth factor (bFGF) was added to the serum-free culture medium during treatment of these cells with anle138b or anle138c. Proliferation of melanoma cells that had received DMSO only, or were treated with anle138b was determined by counting the cells with a hemocytometer.

LDH Cytotoxicity Analysis

Replicates of WM983-B as well as WM852 melanoma cells were plated at $3\times10^5$ cells per well in 35 mm tissue culture plates. Twenty-four hours later, the cells were rinsed three times with serum-free medium, followed by addition of increasing doses of anle138b or DMSO only. Forty-eight hours later, the cell culture medium was removed, followed by addition of equivalent doses of anle138b or DMSO only in serum-free medium. Culture medium, collected 48 hr later, was centrifuged to pellet and remove cellular debris. Using a PHERAstar FS microplate reader (BMG LABTECH GmbH, Ortenberg, Germany) and spectrophotometric absorbance measurement, the release of LDH enzyme activity into the tissue culture medium was determined with an LDH cytotoxicity assay kit (Roche Diagnostics Deutschland GmbH, Mannheim, Germany). Serum-free culture medium supernatants from the WM983-B and WM852 melanoma cells that had received DMSO only served as background controls and their values were subtracted. Cells from the DMSO controls were trypsinized, counted, and lysed according to the manufacturer's instructions. The number of melanoma cells killed was obtained by normalizing LDH release, recorded for each dose of anle138b, to the LDH released upon lysis of a known number of melanoma cells (calibration curve). Standard curves for both cell lines were superimposable.

Cytology and Immunofluorescence

Cell morphology. Phase-contrast or DIC images of the melanoma cells that had been treated for various times with anle138b or anle138c, or had received DMSO only were captured with a 10×NA 0.6 objective on a Zeiss Axiovert 100 microscope with a Hamamatsu Orca charge-coupled device (CCD) camera. At least four images, at random areas per culture dish, were recorded for each time point.

Mitochondrial membrane potential. Melanoma cell lines WM983-B, SK-MEL-5 and WM1158 were treated with anle138b or received DMSO only for 24 or 48 hr. Prior to fixation with 3.7% PFA, the cells were incubated with 200 nM MitoTracker Red CMXRos (Thermo Fisher Scientific, Inc.) for 30 min at 37° C. Confocal image stacks were captured with a 63×NA 1.2 Apochromat water immersion lens on a Zeiss LSM 510 Meta confocal microscope in fluorescence and transmission modes.

α-Synuclein staining. WM983-B melanoma cells, fixed with 4% PFA, and blocked for 30 min at 37° C. with 5 mg/ml of BSA in 0.05% Triton-X 100/PBS, were probed with a rabbit polyclonal anti-α-synuclein [C-20] antibody (Santa Cruz Biotechnology, Inc., Dallas, Tex.), or a mouse monoclonal anti-phosphorylated α-synuclein [pSyn #64] antibody (Wako Chemicals GmbH, Neuss, Germany), and imaged with a 40×/0.60 objective on a Leica DMI6000B inverted microscope. Immunofluorescence comparison of α-synuclein protein expression in the melanoma cell lines, WM983-A, WM983-B, SK-MEL-5 and WM1158, was made by fixation of proliferating cells in 3.7% PFA for 20 min, permeabilization, blocking, and staining with a mouse monoclonal anti-α-synuclein [Syn211] antibody (EMD-Millipore, Darmstadt, Germany), followed by a goat anti-mouse Alexa-546 secondary antibody. Confocal image stacks were acquired with a 63×NA 1.4 oil immersion objective on a Zeiss LSM 510 Meta confocal microscope at the same gain and laser powers.

Autophagy. WM983-B and SK-MEL-5 cells that for 24 or 48 hr were treated with anle138 or had received DMSO only were fixed for 20 min with 3.7% PFA, permeabilized, blocked, and probed with an anti-LC3B [clone 2G6] antibody (nanoTools Antikörpertechnik GmbH & Co. KG, Teningen, Germany), followed by a donkey anti-mouse Alexa-488 secondary antibody and Draq5 DNA counterstain. Confocal image stacks were obtained with a 63×NA 1.2 objective on a Zeiss LSM 510 Meta confocal microscope.

Melanoma Xenograft Study 4-week-old, female nude mice (CAnN.Cg-Foxn1nu/Crl) (Charles River Laboratories, Research Models and Services, Germany GmbH, Sulzfeld, Germany) were injected subcutaneously on their lower right as well as lower left dorsal side with WM983-B (MGP) human melanoma cells ($1\times10^7$ cells per side). When the tumors had reached a size of 2.3 to 3.0 mm in any direction, the normal food pellet diet of one of the animals was replaced with food pellets mixed with anle138b [2 g of anle138b/kg of food pellets] (ssniff Spezialdiäten GmbH, Soest, Germany), while the normal food pellet diet of the other animal was replaced with food pellets (ssniff Spezialdiäten GmbH) not containing anle138b. Both tumor-bearing animals were sacrificed seven days after having received the food pellets with or without anle138, and the resected tumors were immediately frozen in liquid nitrogen. These studies were carried out under approved LAVES protocol (33.19-42502-04-14/1724).

Cryopreserved WM983-B human melanoma xenograft tissues were brought to 4° C. prior to their transfer into Precellys CKMix—2 mL tissue homogenizing tubes, and homogenization in 0.5 to 1.00 ml acetonitrile using a Precellys Evolution Super homogenizer (Bertin Instruments, Montigny-le-Bretonneux, France). Homogenization (6800 rpm, 8 cycles for 30 sec with a 30 sec pause between cycles) was repeated four times. Thereafter, the homogenate was ultrasonicated for 2 min at 25° C., and centrifuged for 2 min. A 100 μl aliquot of the supernatant was injected into a high-performance liquid chromatography (HPLC) system. Analytical HPLC was performed using a Waters HPLC system with a Waters 996 Photodiode Array Detector (Waters Corporation, Milford, Mass., USA). All separations involved a mobile phase of 0.1% trifluoroacetic acid (TFA) (v/v) in water (solvent A) and 0.1% TFA in acetonitrile (solvent B). HPLC was performed using reversed-phase (RP) column Eurospher RP 18, 100 Å, 5 μm, 250×4.6 mm at flow rates of 1 ml/min, with a gradient of solvent B from 0% to 100% in 50 min. The effluent was monitored for UV absorption at 260 nm. Samples were quantitated using peak area ratio of compounds to external standard.

Tissue sections, prepared from the WM983-B human melanoma xenografts, were fixed with methanol, treated with blocking solution (goat serum—0.25% Triton X-100), probed with an anti-LC3 [NB100-2220] antibody (Bio-Techne, Wiesbaden Nordenstadt, Germany), followed by addition of a goat anti-rabbit Alexa-488 secondary antibody, counterstaining with fluorescent 4',6-diamidino-2-phenylindole dihydrochloride (DAPI), and fluorescent mounting

(2E)-1-(3-Bromophenyl)-3-[4-(dimethylamino)phenyl]prop-2-en-1-one (anle458a)

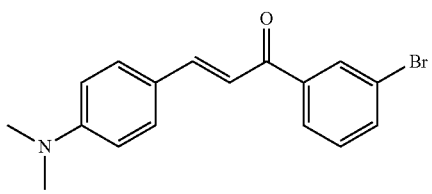 [SMILES: CN(C)c1ccc(/C=C/C(=O)c2cccc(Br)c2)cc1]

This compound has been reported previously (CAS 29170-76-1). A solution of 1-(3-bromophenyl)ethanone (1.99 g, 10 mmol), 4-(dimethylamino)benzaldehyde (1.49 g, 10 mmol), Ba(OH)$_2$.H$_2$O (200 mg, 0.63 mmol) and 40% aqueous NaOH solution (1 mL, 14.3 mmol) in MeOH (40 mL) and water (10 mL) was stirred at room temperature for 18 h. The reaction mixture was cooled to 0° C., the resulting precipitate was collected by filtration, washed with water and n-hexane (10 mL each), and air dried to provide the product anle458a (1.47 g, 4.45 mmol, 44%) as a yellow solid.

$^1$H NMR (400 MHz, DMSO-d$_6$) δ=8.26 (t, J=1.8 Hz, 1H), 8.11 (d, J=7.8 Hz, 1H), 7.82 (dd, J=7.7, 1.3 Hz, 1H), 7.74 (d, J=8.9 Hz, 2H), 7.72 (d, J=15.3 Hz, 1H), 7.64 (d, J=15.3 Hz, 1H), 7.51 (t, J=7.9 Hz, 1H), 6.75 (d, J=8.9 Hz, 2H), 3.01 (s, 6H).

$^{13}$C NMR (100.6 MHz, DMSO-d$_6$) δ=187.1, 152.1, 146.1, 140.4, 135.1, 131.1 (2C), 130.9, 130.7, 127.2, 122.2, 121.8, 115.5, 111.7 (2C), 39.7 (2C).

LC MS (RP18-100 Å, gradient 50% CH$_3$CN/50% H$_2$O→100% CH$_3$CN in 30 min), RT 17.1 min and mass 330.06 (100%), 332.01 (97%) ([M+H]$^+$).

M.p. 108-9° C.

4-[3-(3-Bromophenyl)-1,2-oxazol-5-yl]-N,N-dimethylaniline (anle458c)

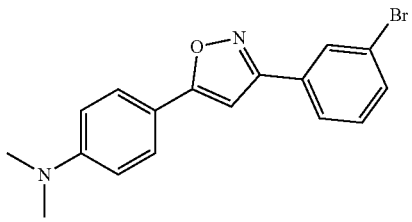 [SMILES: CN(C)c1ccc(-c2cc(-c3cccc(Br)c3)no2)cc1]

To a stirred solution of anle458a (1.34 g, 4.06 mmol) in chloroform (20 mL) was added dropwise a solution of bromine (650 mg, 4.07 mmol) in chloroform (5 mL) at 0° C. The mixture was stirred for at 0° C. and concentrated in vacuum. The residue was suspended in ethanol (30 mL), hydroxylamine hydrochloride (834 mg, 12 mmol) and 50% aqueous NaOH solution (1.92 g, 24 mmol) were added. The mixture was heated under reflux for 14 h with stirring and cooled to room temperature. The resulting precipitate was filtered off, air dried and recrystallized from ethanol to afford the product anle458c (251 mg, 0.73 mmol, 18% over two steps) as white solid.

$^1$H NMR (400 MHz, DMSO-d$_6$) δ=8.08 (t, J=1.6 Hz, 1H), 7.91 (d, J=7.8 Hz, 1H), 7.72 (m, 1H), 7.70 (d, J=8.8 Hz, 2H), 7.50 (t, J=7.9 Hz, 1H), 7.36 (s, 1H), 6.83 (d, J=8.9 Hz, 2H), 3.00 (s, 6H).

$^{13}$C NMR (100.6 MHz, DMSO-d$_6$) δ=171.0, 161.1, 151.4, 132.8, 131.3, 131.2, 129.0, 126.7 (2C), 125.4, 122.3, 114.0, 111.9 (2C), 95.3, 39.7 (2C).

LC MS (RP18-100 Å, gradient 50% CH$_3$CN/50% H$_2$O→100% CH$_3$CN in 30 min), RT 20.5 min and mass 343.04 (100%), 345.12 (97%) ([M+H]$^+$).

M.p. 141-2° C.

3-(1,3-Benzodioxol-5-yl)-5-(3,5-dichlorophenyl)-1,2,4-oxadiazole (anle171129)

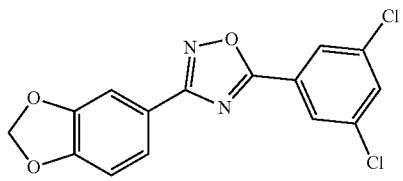 [SMILES: Clc1cc(Cl)cc(-c2nc(-c3ccc4c(c3)OCO4)no2)c1]

To a solution of N-hydroxy-1,3-benzodioxole-5-carboximidamide (180 mg, 1 mmol) and methyl 3,5-dichlorobenzoate (308 mg, 1.5 mmol) in DMSO (3 mL) powdered NaOH (60 mg, 1.5 mmol) was rapidly added. The solid precipitates after 15 min stirring. The heterogeneous mixture was stirred at room temperature for 2 h (TLC control, SiO$_2$, n-Hexane:EtOAc=1:1, educt Rf=0.32, product Rf=0.91). The reaction mixture was diluted with cold water (30 mL). The resulting precipitate was filtered off, washed with water (3×10 mL) and air dried at 50° C. to give the product anle171129 as a white crystalline solid (264 mg, 788 µmol, 79%).

$^1$H NMR (400 MHz, CDCl$_3$) δ=8.08 (d, J=1.9 Hz, 2H), 7.73 (dd, J=8.1, 1.6 Hz, 1H), 7.59 (d, J=1.6 Hz, 1H), 7.58 (d, J=1.9 Hz, 1H), 6.93 (d, J=8.1 Hz, 1H), 6.06 (s, 2H).

$^{13}$C NMR (100.6 MHz, DMSO-d$_6$) δ=173.1, 168.8, 150.4, 148.2, 136.1 (2C), 132.5, 126.8, 126.4 (2C), 122.5, 120.2, 108.7, 107.5, 101.7.

LC MS (RP18-100 Å, gradient 50% CH$_3$CN/50% H$_2$O→100% CH$_3$CN in 30 min), RT 27.1 min and mass 335.04 (100%), 337.12 (65%) ([M+H]$^+$).

M.p. 182-3° C.

5-[5-(3-Bromophenyl)-1H-pyrazol-3-yl]-1-methyl-1H-indole (anle253MIN)

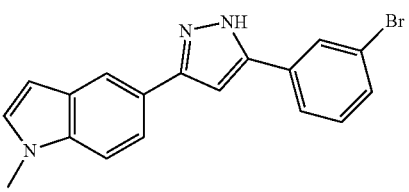 [SMILES: Cn1ccc2cc(-c3cc(-c4cccc(Br)c4)[nH]n3)ccc21]

To a solution of 1-(1-methyl-1H-indol-5-yl)ethanone (520 mg, 3.00 mmol) and methyl 3-bromobenzoate (839 mg, 3.9 mmol) in DMSO (7.5 mL) and THF (1.9 mL) sodium hydride (60% in oil, 3.9 mmol, 156 mg) was added. The reaction mixture was stirred at 20° C. for 15 h, poured into 60 mL of an ice and water containing AcOH (450 μL), stirred for 1 h, and extracted with CHCl$_3$ (4×10 mL). The combined organic layers were dried over Na$_2$SO$_4$ and concentrated in vacuo. To the residue EtOH (20 mL) 80% hydrazine hydrate (547 μL, 563 mg, 9 mmol) were added. The reaction mixture was stirred at 78° C. for 15 h, cooled down, the resulting precipitate was filtered off, washed with cold (0° C.) MeOH and dried in high vacuo at 20° C. for 15 h to afford the product 5-[5-(3-bromophenyl)-1H-pyrazol-3-yl]-1-methyl-1H-indole (623 mg, 1.77 mmol, 59% over two steps) as a tan solid.

$^1$H NMR (400 MHz, DMSO-d$_6$+0.5% TFA) δ=8.08 (t, J=1.6 Hz, 1H), 8.04 (d, J=1.4 Hz, 1H), 7.89 (d, J=7.8 Hz, 1H), 7.65 (dd, J=8.6, 1.4 Hz, 1H), 7.53 (d, J=8.6 Hz, 2H), 7.41 (t, J=7.8 Hz, 1H), 7.38 (d, J=3.0 Hz, 1H), 7.27 (s, 1H), 6.46 (d, J=3.0 Hz, 1H), 3.82 (s, 3H).

$^{13}$C NMR (100.6 MHz, DMSO-d$_6$+0.5% TFA) δ=147.4, 147.2, 136.3, 134.7, 131.0, 130.7 (d, J=8.8 Hz), 130.4, 128.1 (d, J=8.3 Hz), 127.7, 124.1, 122.2, 121.1, 119.1, 117.3, 110.2, 100.8, 99.5, 32.6.

LC MS (RP18-100 Å, gradient 50% CH$_3$CN/50% H$_2$O→100% CH$_3$CN in 30 min), RT 15.9 min and mass 352.12 (100%), 354.01 (97%) ([M+H]$^+$).

M.p. 204-6° C.

1-(3-Bromophenyl)-3-(3,4-dihydro-2H-1,5-benzodioxepin-7-yl)propane-1,3-dione (anle180216)

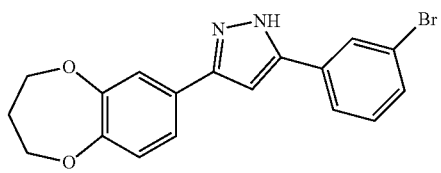 [SMILES: Brc1cccc(-c2cc(-c3ccc4c(c3)OCCCO4)n[nH]2)c1]

To a solution of 1-(3,4-dihydro-2H-1,5-benzodioxepin-7-yl)ethanone (500 mg, 2.6 mmol) and methyl 3-bromobenzoate (671 mg, 3.12 mmol) in DMSO (6 mL) and THF (1.5 mL) sodium hydride (60% in oil, 3.12 mmol, 125 mg) was added, and the mixture was stirred at 20° C. for 96 h. The reaction mixture was poured into 1M phosphate buffer pH 7 (10 mL), extracted with CHCl$_3$ (20 mL). The extract was washed with 1M phosphate buffer pH 7, brine, dried over Na$_2$SO$_4$ and concentrated in vacuum. The residue of the crude 1-(3-bromophenyl)-3-(3,4-dihydro-2H-1,5-benzodioxepin-7-yl)propane-1,3-dione was dissolved in EtOH (10 mL), hydrazine monohydrate (115 μL, 119 mg, 2.37 mmol) was added. The reaction mixture was stirred at 78° C. for 5 h, cooled down and diluted with water (20 mL). The resulting precipitate was filtered off, washed with water (4×5 mL), n-hexane (2×5 mL), and air dried to afford the product (370 mg, 1.0 mmol, 38% over two steps) as white solid.

$^1$H NMR (400 MHz, DMSO-d$_6$+0.5% TFA) δ=8.03 (t, J=1.6 Hz, 1H), 7.84 (d, J=7.8 Hz, 1H), 7.52 (d, J=8.5 Hz, 1H), 7.46 (d, J=2.1 Hz, 1H), 7.40 (t, J=7.8 Hz, 1H), 7.40 (dd, J=8.3, 2.1 Hz, 1H), 7.23 (s, 1H), 7.04 (d, J=8.3 Hz, 1H), 4.17 (q, J=5.8 Hz, 4H), 2.13 (quin, J=5.8 Hz, 2H).

$^{13}$C NMR (100.6 MHz, DMSO-d$_6$+0.5% TFA) δ=151.3, 150.9, 146.8, 145.7, 134.3, 131.0, 130.4, 127.6, 126.0, 124.0, 122.4, 122.1, 120.3, 118.4, 100.0, 70.5, 70.5, 31.5.

LC MS (RP18-100 Å, gradient 50% CH$_3$CN/50% H$_2$O→100% CH$_3$CN in 30 min), RT 16.5 min and mass 371.09 (100%), 373.10 (97%) ([M+H]$^+$).

M.p. 155-6° C.

5-(3-Fluorophenyl)-3-(4-nitrophenyl)-1,2-oxazole (anle 461a)

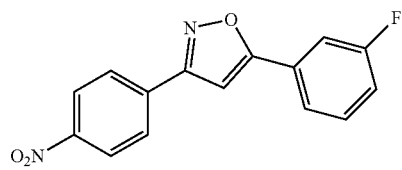

4-Nitrobenzaldehyde (1.51 g, 10 mmol) was added to the solution of hydroxylamine hydrochloride (730 mg, 10.5 mmol) in 40 mL of 1:1 t-BuOH:H$_2$O. To this was added NaOH (420 g, 10.5 mmol), and after being stirred for 30 min at ambient temperature, TLC analysis indicated that oxime formation was complete. Chloramine-T trihydrate (2.96 g, 10.5 mmol) was added in small portions over 5 min, followed by CuSO$_4$.5H$_2$O (75 mg, 0.3 mmol) and copper turnings (ca. 25 mg). 1-Ethynyl-3-fluorobenzene (1.26 g, 10.5 mmol) was added, pH was adjusted to ca. 6 by addition of a few drops of 1 N aqueous NaOH solution, and stirring was continued for another 15 h. The reaction mixture was poured into ice/water (75 mL), and 0.5 mL of 25% NH$_4$OH aqueous solution was added to remove all copper salts. The product was collected by filtration, air dried, redissolved in acetonitrile (100 mL), and passed through a short plug of silica gel affording after evaporation the title compound (1.2 g, 4.2 mmol, 42%) as a white solid.

$^1$H NMR (400 MHz, DMSO-d$_6$) δ=8.40 (ddd, J=8.9, 2.4, 2.0 Hz, 2H), 8.16 (ddd, J=8.9, 2.4, 2.0 Hz, 2H), 7.85 (s, 1H), 7.77 (d, J=8.7 Hz, 1H), 7.77 (d, J=7.9 Hz, 1H), 7.64 (ddd, J=8.3, 6.2, 6.0 Hz, 1H), 7.40 (ddd, J=8.6, 7.9, 5.1.0 Hz, 1H).

$^{13}$C NMR (100.6 MHz, DMSO-d$_6$) δ=169.2 (d, J=3.0 Hz), 162.4 (d, J=244.8 Hz), 161.3, 148.4, 134.3, 131.7 (d, J=8.5 Hz), 128.5 (d, J=8.7 Hz), 127.8 (2C), 124.4 (2C), 121.8 (d, J=2.9 Hz), 117.6 (d, J=21.3 Hz), 112.5 (d, J=23.8 Hz), 100.1.

LC MS (RP18-100 Å, gradient 50% CH$_3$CN/50% H$_2$O→100% CH$_3$CN in 30 min), RT 17.2 min and mass 285.00 (100%) ([M+H]$^+$).

M.p. 188-9° C.

4-[5-(3-fluorophenyl)-1,2-oxazol-3-yl]aniline (anle461b)

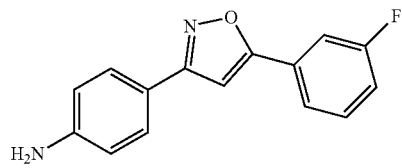 [SMILES: O=[N+]([O-])c1ccc(-c2cc(-c3cccc(F)c3)on2)cc1]

To a suspension of 5-(3-fluorophenyl)-3-(4-nitrophenyl)-1,2-oxazole anle461a (568 mg, 2.0 mmol) in dioxane (4.5 mL) a warm (ca. 60° C.) solution of sodium sulfide trihydrate (660 mg, 5.0 mmol) in water (4.5 mL) was added in one portion at 80° C. The mixture was stirred for 2 h, cooled down to room temperature and poured into ice water (20 mL). After 30 min stirring at 0° C. the resulting precipitate filtered off, washed with cold water (3×5 mL) and air dried. The crude product (409 mg) was dissolved in boiling acetonitrile, filtered (GHP Acrodisc® syringe filter 0.45 μm) and evaporated to afford the title compound (360 mg, 1.41 mmol, 71%) as an orange solid.

$^1$H NMR (400 MHz, DMSO-$d_6$) δ=7.73 (d, J=8.7 Hz, 1H), 7.71 (m, 1H), 7.60 (ddd, J=8.3, 6.1, 6.0 Hz, 1H), 7.57 (ddd, J=8.6, 2.6, 2.0 Hz, 2H), 7.49 (s, 1H), 7.36 (ddd, J=8.6, 7.9, 1.0 Hz, 1H), 6.67 (ddd, J=8.6, 2.6, 2.0 Hz, 2H), 5.60 (s, 2H).

$^{13}$C NMR (100.6 MHz, DMSO-$d_6$) δ=167.4 (d, J=3.0 Hz), 162.8, 162.4 (d, J=244.4 Hz), 150.9, 131.5 (d, J=8.5 Hz), 129.2 (d, J=8.6 Hz), 127.7 (2C), 121.6 (d, J=2.9 Hz), 117.0 (d, J=21.1 Hz), 115.1, 113.7 (2C), 112.3 (d, J=23.8 Hz), 99.0.

LC MS (RP18-100 Å, gradient 50% CH$_3$CN/50% H$_2$O→100% CH$_3$CN in 30 min), RT 6.5 min and mass 254.94 (100%) ([M+H]$^+$).

M.p. 160-1° C.

4-[5-(3-fluorophenyl)-1,2-oxazol-3-yl]N,N-dimethylaniline (anle461c)

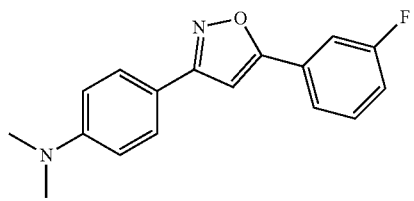 [SMILES: CN(C)c1ccc(-c2cc(-c3cccc(F)c3)on2)cc1]

To a stirred solution of 4-[5-(3-fluorophenyl)-1,2-oxazol-3-yl]aniline anle 461b (254 mg, 1.0 mmol) and formaldehyde (10 M aqueous solution, 1 mL, 10 mmol) in acetonitrile (5 mL) was added sodium cyanoborohydride (189 mg, 3 mmol). Acetic acid (114 μL, 120 mg, 2.0 mmol) was added and the mixture stirred for 2 h. Additional acetic acid (114 μL, 120 mg, 2.0 mmol) was then added and stirring was continued for 6 h. The mixture was diluted with ethyl acetate (20 mL), washed with saturated aqueous sodium hydrogencarbonate solution and brine (5 mL each), dried over sodium sulfate and evaporated to afford the title compound (210 mg, 0.74 mmol, 74%) as a yellowish solid.

$^1$H NMR (400 MHz, DMSO-$d_6$) δ=7.75-7.73 (m, 2H), 7.71 (d, J=8.9 Hz, 2H), 7.61 (ddd, J=8.3, 6.1, 6.0 Hz, 1H), 7.56 (s, 1H), 7.36 (ddd, J=8.6, 7.9, 1.0 Hz, 1H), 6.82 (dd, J=8.9, 2.6 Hz, 2H), 2.98 (s, 6H).

$^{13}$C NMR (100.6 MHz, DMSO-$d_6$) δ=167.6 (d, J=3.0 Hz), 162.6, 162.4 (d, J=244.4 Hz), 151.5, 131.5 (d, J=8.5 Hz), 129.1 (d, J=8.7 Hz), 127.5 (2C), 121.6 (d, J=2.9 Hz), 116.9 (d, J=21.2 Hz), 115.3, 112.3 (d, J=23.7 Hz), 112.0 (2C), 99.1, 39.8 (2C).

LC MS (RP18-100 Å, gradient 50% CH$_3$CN/50% H$_2$O→100% CH$_3$CN in 30 min), RT 12.2 min and mass 282.98 (100%) ([M+H]$^+$).

M.p. 152-3° C.

7-[5-(3-Bromophenyl)-1H-pyrazol-3-yl]-4-methyl-3,4-dihydro-2H-1,4-benzoxazine (anle180222)

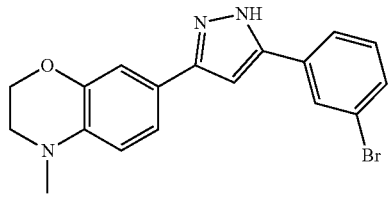 [SMILES: CN1CCOc2cc(-c3cc(-c4cccc(Br)c4)[nH]n3)ccc21]

Dicyclohexylcarbodiimide (807 mg, 3.91 mmol) was added to a stirred suspension of 4-methyl-3,4-dihydro-2H-1,4-benzoxazine-7-carboxylic acid (CAS 532391-89-2) (685 mg, 3.55 mmol) and pentafluorophenol (653 mg, 3.55 mmol) in 1,4-dioxane (15 mL). Stirring was continued for 17 h by which time a colorless precipitate had formed. The mixture was filtered and evaporated; the residue was dissolved in CH$_2$Cl$_2$ (20 mL) and evaporated to give the crude ester pentafluorophenyl 4-methyl-3,4-dihydro-2H-1,4-benzoxazine-7-carboxylate (1.4 g, 3.90 mmol, 100%) as a yellow oily solid which was used in the next step without purification. iPr$_2$NEt (523 μL, 388 mg, 3 mmol) was added to a stirred mixture of 1-(3-bromophenyl)ethanone (199 mg, 1 mmol) and MgBr$_2$.Et$_2$O (646 mg, 2.5 mmol) in CH$_2$Cl$_2$ (10 mL). The resulting suspension was stirred for 15 min, then pentafluorophenyl 4-methyl-3,4-dihydro-2H-1,4-benzoxazine-7-carboxylate (431 mg, 1.2 mmol) in CH$_2$Cl$_2$ (2 mL) was added dropwise. After 24 h 1-(3-bromophenyl)ethanone (199 mg, 1 mmol), MgBr$_2$.Et$_2$O (646 mg, 2.5 mmol), and iPr$_2$NEt (523 μL, 388 mg, 3 mmol) were added and the stirring was continued for further 24 h. 1N phosphate buffer pH 6 (20 mL) was added, stirred for 10 min, the organic phase was separated, the aqueous phase was extracted with CHCl$_3$ (10 mL), the combined organic extract was washed with saturated NaHCO$_3$ solution, brine, dried over Na$_2$SO$_4$ and concentrated in vacuo. The residue was purified by flash chromatography on silica gel (n-hexane/chloroform=1:1, R$_f$ 0.15) to afford 362 mg of crude product as yellow foam which was used in the next step without further purification. To a solution of crude 1-(3-bromophenyl)-3-(4-methyl-3,4-dihydro-2H-1,4-benzoxazin-7-yl)propane-1,3-dione (362 mg) in EtOH (10 mL) hydrazine monohydrate (194 μL, 200 mg, 4 mmol) was added. The reaction mixture was stirred at 78° C. for 15 h, cooled down to room temperature, the solvent and excess of hydrazine monohydrate were removed on the rotary evaporator. Toluene (20 mL) was added and the mixture was concentrated to dryness. The crude product (380 mg) was purified by flash chromatography on silica gel (chloroform/methanol=100:1, R$_f$ 0.26) to afford the product (30 mg, 0.08 mmol, 8% over three steps) as a white solid.

$^1$H NMR (400 MHz, DMSO-$d_6$+0.5% TFA) δ=8.04 (t, J=1.6 Hz, 1H), 7.86 (d, J=7.8 Hz, 1H), 7.52 (bd, J=8.5 Hz, 1H), 7.40 (t, J=7.8 Hz, 1H), 7.29 (dd, J=8.4, 1.8 Hz, 1H), 7.19 (d, J=1.8 Hz, 1H), 7.16 (s, 1H), 6.79 (d, J=8.4 Hz, 1H), 4.26 (bt, J=4.2 Hz, 2H), 3.30 (bt, J=4.2 Hz, 2H), 2.89 (s, 3H).

$^{13}$C NMR (100.6 MHz, DMSO-$d_6$+0.5% TFA) δ=147.3, 145.9, 144.0, 136.5, 134.4, 131.0, 130.5, 127.7, 124.2, 122.2, 119.5, 118.7, 112.8, 112.4, 99.1, 64.3, 48.3, 38.4.

LC MS (RP18-100 Å, gradient 50% CH$_3$CN/50% H$_2$O→100% CH$_3$CN in 30 min), RT 15.5 min and mass 370.08 (100%), 372.03 (97%) ([M+H]$^+$).

M.p. 210° C.

1-(Benzofuran-5-yl)-3-(3-bromophenyl)propane-1,3-dione (sery428a)

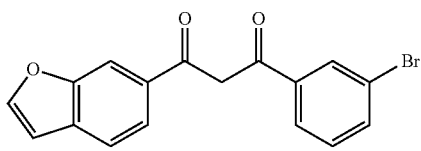 [SMILES: O=C(CC(=O)c1ccc2ccoc2c1)c1cccc(Br)c1]

The title compound was prepared according to the published protocol[1]. A 60% suspension of sodium hydride in mineral oil (0.048 g, 1.2 mmol) was washed with petroleum benzin (20 ml) twice, anhydrous DMSO (2 ml) was added. After being stirred for 30 min at room temperature under argon, the flask was cooled down to 15° C. and a solution of methyl 3-bromobenzoate (0.27 g, 1.2 mmol) and 6-acetyl-benzofuran (0.15 g, 0.94 mmol) in DMSO (1 ml) was added dropwise. Upon completion of addition the reaction mixture was stirred 15 h at room temperature, then poured slowly into crushed ice (50 g) containing 85 phosphoric acid (0.25 ml). The resulting precipitate was collected by filtration, washed with water (50 ml) and dried to provide crude sery428b (0.25 g) as a yellow powder that was used in next step without purification.

3-(Benzofuran-5-yl)-5-(3-bromophenyl)-1H-pyrazole (sery428b)

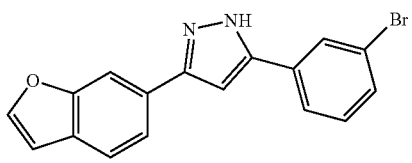 [SMILES: Brc1cccc(-c2cc(-c3ccc4ccoc4c3)n[nH]2)c1]

The title compound was prepared according to the published protocol[1]. A solution of sery428a (250 mg, 0.73 mmol) and hydrazine hydrate (50 mg, 1.0 mmol) in ethanol (8 ml) was heated under reflux 12 h with stirring. The clear yellow solution was evaporated under reduced pressure, water was added and the resulting precipitate was collected by filtration, washed with water, dried and recrystallized from ethanol to provide sery428b (124 mg, 50%) as a beige powder.

TLC (hexane:EtOAc, 3/1 v/v): RF=0.37.

$^1$H NMR (400 MHz, DMSO-$d_6$+1% conc. DCl) δ=8.09-8.06 (m, 2H), 8.04 (d, J=1.6 Hz, 1H), 7.88 (dt, J=7.9, 1.1 Hz, 1H), 7.78 (dd, J=8.2, 1.4 Hz, 1H), 7.73 (d, J=8.2 Hz, 1H), 7.53 (ddd, J=8.0, 1.8, 1.0 Hz, 1H), 7.42 (t, J=7.9 Hz, 1H), 7.39 (s, 1H), 6.99 (dd, J=2.1, 0.8 Hz, 1H).

$^{13}$C NMR (100.6 MHz, DMSO-$d_6$+1% conc. DCl) δ=154.8, 147.0, 146.8, 146.7, 134.1, 131.1, 130.5, 127.7, 127.2 (2C), 124.2, 122.3, 121.7, 120.6, 107.9, 106.9, 100.6.

LC MS (RP18-100 Å, gradient 0% CH$_3$CN/100% H$_2$O→100% CH$_3$CN in 50 min), RT 40.9 min and mass 339.05 (100%), 341.01 (100%) ([M+H]$^+$).

M.p. 201-202° C.

5-(3,4-dichlorophenyl)-oxazole (sery537)

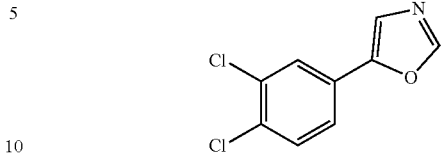

The title compound has been reported previously (CAS 503596-50-7). It was prepared according to the published protocol[2]. To a stirred mixture of 3,4-dichlorobenzaldehyde (1.75 g, 10 mmol) and TosMIC (2.05 g, 10.5 mmol) in methanol (50 mL) was added in one portion potassium carbonate (2.76 g, 20 mmol). After stirring at room temperature for 30 min, the resulting reaction mixture was heated under reflux for 4 h, concentrated under reduced pressure and treated with water (100 ml). A resulting precipitate was collected by filtration, washed with water (20 ml) and dried to provide sery537 (2.08 g, 97%) as a yellow solid.

TLC (hexane:EtOAc, 3/1 v/v): RF=0.44.

$^1$H NMR (400 MHz, DMSO-$d_6$) δ=8.50 (s, 1H), 7.97 (dd, J=1.8 Hz, 1H), 7.84 (s, 1H), 7.71 (d, J=8.4 Hz, 1H), 7.67 (dd, J=8.4, 1.8 Hz, 1H).

$^{13}$C NMR (100.6 MHz, DMSO-$d_6$) δ=152.5, 148.3, 132.0, 131.4, 130.9, 127.9, 125.7, 124.1, 123.8.

LC MS (RP18-100 Å, gradient 0% CH$_3$CN/100% H$_2$O→100% CH$_3$CN in 50 min), RT 39.3 min and mass 213.87 (100%), 215.9 (65%) ([M+H]$^+$).

M.p. 100-101° C.

5-(3,4-dichlorophenyl)-2-(3-nitrophenyl)oxazole (sery539)

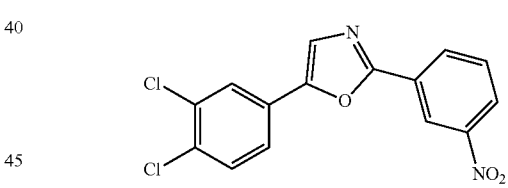

The title compound was prepared according to the published protocol[3]. A mixture of sery537 (1.07 g, 5 mmol), 1-iodo-3-nitrobenzene (1.49 g, 6 mmol), CuI (1.14 g, 6 mmol), PPh$_3$ (265 mg, 1 mmol) and Na$_2$CO$_3$ (1.06 g, 10 mmol) in dry DMF (10 ml) was stirred at 160° C. for 2 h under an inert atmosphere (Ar). After cooling to room temperature, the mixture was poured into 2M ammonium chloride aq. solution (150 ml) and extracted with ethyl acetate (3×100 ml). Combined organic fractions were washed with brine (20 ml), dried (Na$_2$SO$_4$) and evaporated. A resulting solid was recrystallized from acetonitrile to provide sery539 (0.87 g, 52%) as a yellow solid.

TLC (hexane:EtOAc, 3/1 v/v): RF=0.53.

$^1$H NMR (400 MHz, DMSO-$d_6$) δ=8.79 (t, J=1.9 Hz, 1H), 8.54 (dt, J=7.9, 1.2 Hz, 1H), 8.37 (ddd, J=8.2, 2.3, 0.9 Hz, 1H), 8.21 (d, J=2.0 Hz, 1H), 8.08 (s, 1H), 7.91-7.83 (m, 2H), 7.77 (d, J=8.5 Hz, 1H).

$^{13}$C NMR (100.6 MHz, DMSO-$d_6$) δ=158.9, 149.5, 148.3, 132.2, 132.1, 131.4, 131.2, 131.0, 127.8, 127.5, 126.3, 125.9, 125.2, 124.3, 120.5.

LC MS (RP18-100 Å, gradient 0% CH$_3$CN/100% H$_2$O→100% CH$_3$CN in 30 min and 5 min 100% CH$_3$CN), RT 31.7 min and mass 335.09 (100%), 337.05 (65%) ([M+H]$^+$).

M.p. 199-201° C.

2-(3-aminophenyl)-5-(3,4-dichlorophenyl)oxazole (sery540)

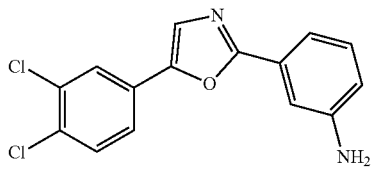 [SMILES: O=[N+]([O-])c1cccc(-c2ncc(-c3ccc(Cl)c(Cl)c3)o2)c1]

The title compound was prepared according to the published protocol[1]. To a suspension of sery539 (860 mg, 2.6 mmol) in dioxane (10 mL) a warm (ca. 60° C.) solution of sodium sulfide trihydrate (855 mg, 6.5 mmol) in water (10 mL) was added in one portion at 80° C. The mixture was stirred for 2 h, cooled down to room temperature and poured into ice water (20 mL). After 30 min stirring at 0° C. the resulting precipitate was filtered off, washed with cold water (2×10 mL) and air dried. The crude product was recrystallized from n-butanol to provide sery540 (433 mg, 55%) as a brown solid.

TLC (chloroform:MeOH, 40/1 v/v): RF=0.44.

$^1$H NMR (400 MHz, DMSO-d$_6$) δ=8.07 (d, J=1.6 Hz, 1H), 7.93 (s, 1H), 7.78-7.75 (m, 2H), 7.35 (t, J=1.8 Hz, 1H), 7.29 (d, J=7.8 Hz, 1H), 7.2 (t, J=7.8 Hz, 1H), 6.75 (dd, J=7.8, 1.8 Hz, 1H), 5.4 (bs, 2H).

$^{13}$C NMR (100.6 MHz, DMSO-d$_6$) δ=161.7, 149.3, 148.0, 132.1, 131.4, 130.6, 129.6, 128.1, 127.0, 126.0, 125.4, 123.9, 116.4, 113.7, 110.0.

LC MS (RP18-100 Å, gradient 0% CH$_3$CN/100% H$_2$O→100% CH$_3$CN in 50 min), RT 33.5 min and mass 305.02 (100%), 336.98 (65%) ([M+H]$^+$).

M.p. 179-180° C.

2-(3-bromophenyl)-4-(2,3-dihydro-1,4-benzodioxin-6-yl)oxazole (sery534)

The title compound was prepared according to the published protocol[4]. A mixture of 1-(2,3-dihydro-1,4-benzodioxin-6-yl)ethanone (890 mg, 5.0 mmol) and HDNIB (2.81 g, 6.0 mmol) in acetonitrile (50 ml) was heated under reflux for 2.5 h. 3-bromobenzamide (3.0 g, 15 mmol) was added in one portion and stirring was continued for additional 12 h with reflux. After cooling to room temperature, solvent was evaporated under reduced pressure. DCM (100 ml), water (50 ml) and saturated aq. NaHCO$_3$ solution (50 ml) were added to the residual solid. The organic phase was separated, washed with water (50 ml), brine (20 ml), dried over Na$_2$SO$_4$, filtered and evaporated under reduced pressure. The crude product was purified by column chromatography on silica gel (DCM/n-hexane=2:1 v/v) to provide sery534 (700 mg, 39%) as a white solid.

TLC (DCM/n-hexane, 2:1 v/v): RF=0.52.

$^1$H NMR (400 MHz, DMSO-d$_6$) δ=8.63 (s, 1H), 8.14 (t, J=1.8 Hz, 1H), 8.01 (d, J=7.9 Hz, 1H), 7.74 (d, J=7.9 Hz, 1H), 7.51 (t, J=7.9 Hz, 1H), 7.38-7.31 (m, 2H), 6.93 (d, J=8.2 Hz, 1H), 4.28 (s, 4H).

$^{13}$C NMR (100.6 MHz, DMSO-d$_6$) δ=159.2, 143.6, 143.5, 140.9, 135.2, 133.3, 131.4, 128.8, 128.3, 125.0, 123.8, 122.3, 118.4, 117.4, 113.9, 64.2, 64.1.

LC MS (RP18-100 Å, gradient 0% CH$_3$CN/100% H$_2$O→100% CH$_3$CN in 50 min), RT 45.2 min and mass 358.09 (100%), 359.98 (100%) ([M+H]$^+$).

M.p. 125-126° C.

2-(3-bromophenyl)-5-(3-methoxyphenyl)-1H-imidazole (sery547)

The title compound was prepared according to the published protocol with minor modifications[1]. A mixture of 3-bromobenzamidine hydrochloride (706 mg, 3.0 mmol) and sodium bicarbonate (840 mg, 10.0 mmol) in THF (10 ml) and water (2.5 ml) was heated under reflux. A solution of 2-bromo-1-(3-methoxyphenyl)ethanone (687 mg, 3.0 mmol) in THF (2.5 ml) was added dropwise over a period of 10 min, while keeping the mixture under reflux. After addition, the mixture was heated under reflux for 6 h and THF was evaporated under reduced pressure. Ethyl acetate (20 ml) and saturated aq. NaHCO$_3$ solution (20 ml) were added to the mixture. The organic phase was separated, washed with the brine (10 ml), dried over Na$_2$SO$_4$ and evaporated under reduced pressure. The resulting crude product was recrystallized from a mixture of petroleum ether/chloroform (2/1 v/v) to provide sery547 (640 mg, 65%) as a white solid.

TLC (chloroform:MeOH, 100/1 v/v): RF=0.34.

$^1$H NMR (400 MHz, DMSO-d$_6$+0.5% TFA) δ=8.32 (s, 1H), 8.18 (s, 1H), 8.07 (d, J=7.7 Hz, 1H), 7.78 (d, J=7.9 Hz, 1H), 7.57 (t, J=7.9 Hz, 1H), 7.52-7.45 (m, 2H), 7.42 (t, J=8.2 Hz, 1H), 6.98 (d, J=7.9 Hz, 1H), 3.84 (s, 3H).

$^{13}$C NMR (100.6 MHz, DMSO-d$_6$+0.5% TFA) δ=159.8, 143.3, 135.5, 133.5, 131.3, 130.2, 130.0, 129.1, 127.5, 125.5, 122.4, 117.7, 117.5, 114.2, 110.8, 55.3.

LC MS (RP18-100 Å, gradient 0% CH$_3$CN/100% H$_2$O→100% CH$_3$CN in 50 min), RT 29.2 min and mass 328.99 (100%), 331.01 (100%) ([M+H]$^+$).

M.p. 136-137° C.

5-(3-chlorophenyl)-3-(4-methoxyphenyl)-1,2,4-oxadiazole (sery562)

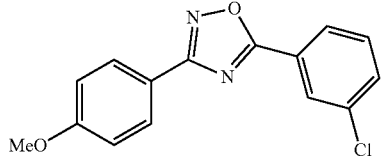 [SMILES: COc1ccc(-c2noc(-c3cccc(Cl)c3)n2)cc1]

The title compound was prepared according to the published protocol[5]. To a solution of 4-methoxybenzamidoxime (332 mg, 2 mmol) and methyl 3-chlorobenzoate (554 mg, 3 mmol) in DMSO (3 mL) powdered NaOH (120 mg, 3.0 mmol) was rapidly added. The solid precipitate was formed after 15 min stirring. The heterogeneous mixture was stirred at room temperature for 3 h. The reaction mixture was diluted with cold water (60 mL). The resulting precipitate was filtered off, washed with water (3×30 mL) and air dried to provide the product sery562 as a white crystalline solid (520 mg, 91%).

TLC (hexane:EtOAc, 7/1 v/v): RF=0.50.

$^1$H NMR (400 MHz, DMSO-$d_6$) δ=8.16 (t, J=1.6 Hz, 1H), 8.13 (d, J=7.8 Hz, 1H), 8.03 (d, J=8.8 Hz, 2H), 7.80 (m, 1H), 7.69 (t, J=7.2 Hz, 1H), 7.14 (d, J=8.8 Hz, 2H), 3.85 (s, 3H).

$^{13}$C NMR (100.6 MHz, DMSO-$d_6$) δ=173.9, 168.0, 161.9, 134.1, 133.1, 131.6, 128.8, 127.4, 126.6, 125.3, 118.2, 114.7, 55.4.

LC MS (RP18-100 Å, gradient 0% CH$_3$CN/100% H$_2$O→100% CH$_3$CN in 50 min), RT 46.8 min and mass 287.06 (100%), 288.95 (35%) ([M+H]$^+$).

M.p. 130° C.

3-(1,3-Benzodioxol-5-yl)-5-(3-bromophenyl)-1,2,4-oxadiazole (sery564)

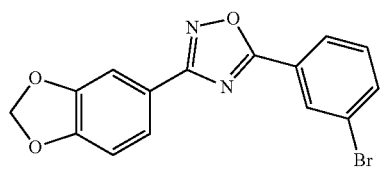 [SMILES: Brc1cccc(-c2nc(-c3ccc4c(c3)OCO4)no2)c1]

The title compound was prepared according to the published protocol[5]. To a solution of N-hydroxy-1,3-benzodioxole-5-carboximidamide (360 mg, 2 mmol) and methyl 3-bromobenzoate (645 mg, 3 mmol) in DMSO (3 mL) powdered NaOH (120 mg, 3.0 mmol) was rapidly added. The solid precipitate was formed after 15 min stirring. The heterogeneous mixture was stirred at room temperature for 3 h. The reaction mixture was diluted with cold water (60 mL). The resulting precipitate was filtered off, washed with water (3×30 mL) and air dried to provide the product sery564 as a white crystalline solid (545 mg, 79%).

TLC (hexane:EtOAc, 7/1 v/v): RF=0.55.

$^1$H NMR (400 MHz, CDCl$_3$) δ=8.35 (t, J=1.6 Hz, 1H), 8.12 (dt, J=7.8, 1.3 Hz, 1H), 7.75-7.70 (m, 2H), 7.59 (d, J=1.7 Hz, 1H), 7.42 (t, J=7.8 Hz, 1H), 6.93 (d, J=8.1 Hz, 1H), 6.05 (s, 2H).

$^{13}$C NMR (100.6 MHz, CDCl$_3$) δ=174.2, 168.8, 150.4, 148.3, 135.8, 131.2, 130.8, 126.7, 126.4, 123.3, 122.6, 120.6, 108.8, 107.7, 101.8.

LC MS (RP18-100 Å, gradient 0% CH$_3$CN/100% H$_2$O→100% CH$_3$CN in 50 min), RT 46.9 min and mass 344.92 (100%), 346.95 (100%) ([M+H]$^+$).

M.p. 163-164° C.

1-(3-chlorophenyl)-3-(2,3-dihydro-1,4-benzodioxin-6-yl)propane-1,3-dione (sery595)

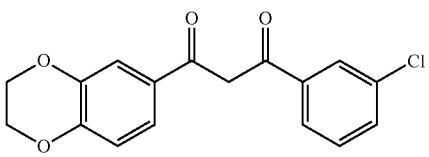 [SMILES: O=C(CC(=O)c1ccc2c(c1)OCCO2)c1cccc(Cl)c1]

The title compound was prepared according to the published protocol[1]. A 60% suspension of sodium hydride in mineral oil (0.2 g, 5.0 mmol) was washed with petroleum benzin (20 ml) twice, anhydrous DMSO (4 ml) was added. After being stirred for 30 min at room temperature under argon, the flask was cooled down to 15° C. and a solution of methyl 3-chlorobenzoate (0.853 g, 5.0 mmol) and 1-(2,3-dihydro-1,4-benzodioxin-6-yl)ethanone (0.712 g, 4.0 mmol) in DMSO (4 ml) was added dropwise. Upon completion of addition, the reaction mixture was stirred 24 h at room temperature, then poured slowly into crushed ice (50 g) containing 85% phosphoric acid (1 ml). The resulting precipitate was collected by filtration, washed with water (50 ml) and air dried. The resulting crude product was recrystallized from methanol to provide sery595 (590 mg, 47%) as a light-yellow powder.

TLC (hexane:EtOAc, 3/1 v/v): RF=0.53.

$^1$H NMR (400 MHz, DMSO-$d_6$) δ=8.24 (t, J=1.8 Hz, 1H), 8.10 (d, J=7.8 Hz, 1H), 7.79-7.73 (m, 2H), 7.69 (m, 1H), 7.58 (t, J=7.8 Hz, 1H), 7.32 (s, 1H), 7.02 (d, J=8.3 Hz, 1H), 4.39-4.29 (m, 4H), (in $^1$H NMR spectrum 6.5% of diketone form is present).

$^{13}$C NMR (100.6 MHz, DMSO-$d_6$) δ=186.2, 181.6, 148.1, 143.5, 136.6, 133.8, 132.4, 130.7, 127.8, 126.9, 125.8, 121.7, 117.4, 116.7, 93.1, 64.6, 63.9.

LC MS (RP18-100 Å, gradient 0% CH$_3$CN/100% H$_2$O→100% CH$_3$CN in 50 min), RT 45.8 min and mass 317.04 (100%), 318.99 (35%) ([M+H]$^+$).

M.p. 106-107° C.

3-(3-chlorophenyl)-5-(2,3-dihydro-1,4-benzodioxin-6-yl)-1H-pyrazole (sery599)

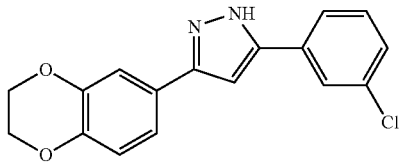 [SMILES: Clc1cccc(-c2cc(-c3ccc4c(c3)OCCO4)n[nH]2)c1]

The title compound was prepared according to the published protocol[1]. A solution of sery595 (400 mg, 1.27 mmol) and hydrazine hydrate (95 mg, 1.9 mmol) in ethanol (10 ml) was heated under reflux 14 h with stirring. After addition of water (1 ml) to the hot reaction mixture, the solution was cooled down to the room temperature and kept 1 h at −20° C. The resulting precipitate was collected by filtration, washed with water (5 ml), dried and recrystallized from methanol to provide sery599 (335 mg, 84%) as a white powder.

TLC (hexane:EtOAc, 3/1 v/v): RF=0.25.

$^1$H NMR (400 MHz, DMSO-$d_6$+1% conc. DCI) δ=7.90 (t, J=1.8 Hz, 1H), 7.81 (dt, J=7.8, 1.1 Hz, 1H), 7.47 (t, J=7.9, 1H), 7.38 (m, 1H), 7.35 (d, J=2.1 Hz, 1H), 7.31 (dd, J=8.4, 2.1 Hz, 1H), 7.21 (s, 1H), 6.94 (d, J=8.4 Hz, 1H), 4.27 (s, 4H).

$^{13}$C NMR (100.6 MHz, DMSO-$d_6$+1% conc. DCI) δ=147.0, 145.9, 143.7, 143.6, 134.1, 133.7, 130.8, 127.6, 124.8, 123.8, 123.7, 118.5, 117.6, 114.0, 99.9, 64.24, 64.19.

LC MS (RP18-100 Å, gradient 0% CH$_3$CN/100% H$_2$O→100% CH$_3$CN in 50 min), RT 37.9 min and mass 313.05 (100%), 314.94 (35%) ([M+H]$^+$).

M.p. 155-156° C.

1-(3-Bromophenyl)-3-(quinoxalin-6-yl)propane-1,3-dione (sery606)

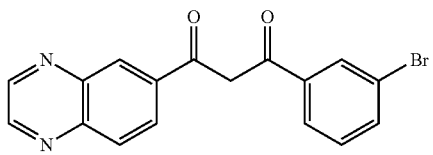 [SMILES: O=C(CC(=O)c1ccc2nccnc2c1)c1cccc(Br)c1]

The title compound was prepared according to the published protocol[1]. Dicyclohexylcarbodiimide (681 mg, 3.3 mmol) was added to a stirred suspension of 6-quinoxalinecarboxylic acid (522 mg, 3.0 mmol) and pentafluorophenol (552 mg, 3.0 mmol) in 1,4-dioxane (15 mL). Stirring was continued for 15 h by which time a colorless precipitate had formed. The mixture was filtered, the precipitate was washed on the filter with dioxane (5 ml) and the combined solution was concentrated under reduced pressure. The residue was dissolved in CH$_2$Cl$_2$ (20 mL) and evaporated to give the crude pentafluorophenyl ester of 6-quinoxalinecarboxylic acid as an oily solid which was used in the next step without purification. iPr$_2$NEt (890 mg, 6.9 mmol) was added to a stirred mixture of 1-(3-bromophenyl)ethanone (459 mg, 2.3 mmol) and MgBr$_2$.Et$_2$O (1.49 g, 5.75 mmol) in CH$_2$Cl$_2$ (20 mL). The resulting suspension was stirred for 15 min, then pentafluorophenyl ester of 6-quinoxalinecarboxylic acid (431 mg, 1.2 mmol) in CH$_2$Cl$_2$ (5 mL) was added dropwise. After 7 h of stirring at room temperature 1-(3-bromophenyl)ethanone (150 mg, 0.7 mmol) was added and the stirring was continued for another 14 h. The resulting solution was poured into a mixture of water (100 ml), DCM (300 ml) and 1M aq. HCl solution (7 ml), the organic phase was separated, washed with saturated aq. NaHCO$_3$ solution (50 ml) (20 ml), dried over Na$_2$SO$_4$ and concentrated in vacuo. The residue was purified by flash chromatography on silica gel (n-hexane/chloroform=2/1) to afford 770 mg of crude product as a beige powder, which was used in the next step without further purification.

TLC (DCM:MeOH, 100/1 v/v): RF=0.34.

3-(3-bromophenyl)-5-(quinoxalin-6-yl)-1H-pyrazole (sery607)

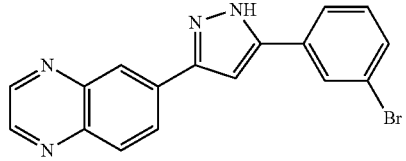 [SMILES: Brc1cccc(-c2cc(-c3ccc4nccnc4c3)n[nH]2)c1]

The title compound was prepared according to the published protocol[1]. A solution of sery606 (620 mg, 1.75 mmol) and hydrazine hydrate (200 mg, 4 mmol) in ethanol (15 ml) was heated under reflux 24 h with stirring. After cooling of the reaction mixture to room temperature, the resulting precipitate was collected by filtration, washed with cold ethanol (10 ml) and then with water (2×10 ml), and air dried to provide sery607 (420 mg, 68%) as a white powder.

TLC (chloroform:MeOH, 95/5 v/v): RF=0.23.

$^1$H NMR (400 MHz, DMSO-$d_6$+1% conc. DCI) δ=8.96 (d, J=1.8 Hz, 1H), 8.92 (d, J=1.8 Hz, 1H), 8.54 (d, J=1.8 Hz, 1H), 8.37 (dd, J=8.8, 2.0 Hz, 1H), 8.16 (d, J=8.8 Hz, 1H), 8.10 (d, J=1.7 Hz, 1H), 7.90 (d, J=7.8 Hz, 1H), 7.61 (s, 1H), 7.54 (ddd, J=8.1, 1.8, 0.9 Hz, 1H), 7.43 (t, J=7.8 Hz, 1H).

$^{13}$C NMR (100.6 MHz, DMSO-$d_6$+1% conc. DCI) δ=146.5, 146.4, 146.1, 145.5, 142.7, 142.0, 133.4, 132.9, 131.2, 130.7, 129.8, 127.8, 127.7, 124.23, 124.19, 122.4, 101.8.

LC MS (RP18-100 Å, gradient 0% CH$_3$CN/100% H$_2$O→100% CH$_3$CN in 50 min), RT 42.0 min and mass 351.00 (100%), 353.02 (100%) ([M+H]$^+$).

M.p. 228-229° C.

(2E)-1-(3-Bromophenyl)-3-(3,4-dihydro-2,2-dimethyl-2H-1-benzopyran-6-yl)prop-2-en-1-one (sery596)

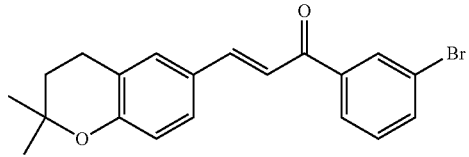 [SMILES: CC1(C)CCc2cc(/C=C/C(=O)c3cccc(Br)c3)ccc2O1]

The title compound was prepared according to the published protocol[1]. A solution of 1-(3-bromophenyl)ethanone (497 mg, 2.5 mmol), 3,4-dihydro-2,2-dimethyl-2H-1-benzopyran-6-carboxaldehyde (475 mg, 2.5 mmol), Ba(OH)$_2$—H$_2$O (20 mg, 0.06 mmol) and NaOH (3 mg) in MeOH (7 mL) was stirred at room temperature for 24 h. The reaction mixture was kept for 2 h at −20° C., the resulting precipitate was collected by filtration, washed with cold methanol (3 ml) and air dried to provide the product sery596 (710 mg, 77%) as a yellow solid.

TLC (hexane:EtOAc, 7/1 v/v): RF=0.51.

$^1$H NMR (400 MHz, DMSO-$d_6$) δ=8.28 (t, J=1.9 Hz, 1H), 8.14 (dt, J=7.9, 1.3 Hz, 1H), 7.84 (ddd, J=7.9, 1.9, 0.9 Hz, 1H), 7.77 (d, J=14.0 Hz, 1H), 7.73-7.67 (m, 2H), 7.64 (dd, J=8.4, 2.1 Hz, 1H), 7.52 (t, J=7.9 Hz, 1H), 6.78 (d, J=8.4 Hz, 1H), 2.78 (t, J=6.7 Hz, 2H), 1.80 (t, J=6.7 Hz, 2H), 1.30 (s, 6H).

$^{13}$C NMR (100.6 MHz, DMSO-d$_6$) δ=187.5, 156.4, 145.3, 140.0, 135.5, 131.1, 130.9, 130.8, 128.8, 127.4, 126.2, 122.3, 121.5, 118.4, 117.3, 75.2, 31.9, 26.6, 21.7.

LC MS (RP18-100 Å, gradient 0% CH$_3$CN/100% H$_2$O→100% CH$_3$CN in 50 min), RT 46.8 min and mass 371.12 (100%), 373.07 (100%) ([M+H]$^+$).

M.p. 127-128° C.

2,3-Dibromo-1-(3-bromophenyl)-3-(3,4-dihydro-2,2-dimethyl-2H-1-benzopyran-6-yl)propan-1-one (sery597)

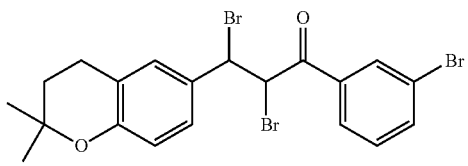 [SMILES: CC1(C)CCc2cc(C(Br)C(Br)C(=O)c3cccc(Br)c3)ccc2O1]

The title compound was prepared according to the published protocol[1]. To a stirred solution of sery596 (371 mg, 1.0 mmol) in chloroform (7 ml) a solution of bromine (160 mg, 1.0 mmol) in chloroform (7 ml) was added dropwise at 0° C. After being stirred for 30 min at 0° C. and then 4 h at room temperature the reaction mixture was concentrated in vacuo. The residue was triturated in n-hexane (15 ml), the resulting precipitate was collected by filtration, washed with n-hexane (5 ml) and air dried to provide sery597 (310 mg, 58%) as a white solid.

TLC (hexane:EtOAc, 3/1 v/v): RF=0.49.

$^1$H NMR (400 MHz, CDCl$_3$) δ=8.21 (t, J=1.8 Hz, 1H), 8.02 (ddd, J=7.9, 1.7, 1.1 Hz, 1H), 7.78 (ddd, J=7.9, 1.9, 1.1 Hz, 1H), 7.43 (t, J=7.9 Hz, 1H), 7.25 (dd, J=8.5, 2.3 Hz, 1H), 7.20 (d, J=2.3 Hz, 1H), 6.82 (d, J=8.5 Hz, 1H), 5.74 (d, J=11.3 Hz, 1H), 5.60 (d, J=11.3 Hz, 1H), 2.82 (t, J=6.8 Hz, 2H), 1.84 (t, J=6.8 Hz, 2H), 1.36 (s, 3H), 1.35 (s, 3H).

$^{13}$C NMR (100.6 MHz, CDCl$_3$) δ=190.3, 155.1, 137.1, 136.4, 132.0, 130.7, 129.8, 128.8, 127.5, 127.4, 123.5, 121.4, 117.9, 75.0, 50.9, 47.2, 32.7, 27.2, 27.0, 22.6.

LC MS (RP18-100 Å, gradient 0% CH$_3$CN/100% H$_2$O→100% CH$_3$CN in 50 min), RT 40.2 min and mass 530.11 (50%), 532.20 (100%), 534.03 (50%) ([M+H]$^+$).

M.p. 135° C.

5-(3-Bromophenyl)-3-(3,4-dihydro-2,2-dimethyl-2H-1-benzopyran-6-yl)-1H-pyrazole (sery603)

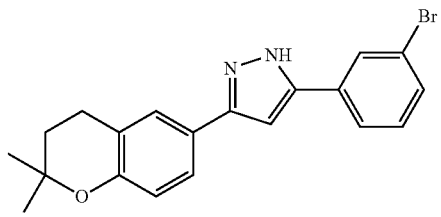 [SMILES: CC1(C)CCc2cc(-c3cc(-c4cccc(Br)c4)[nH]n3)ccc2O1]

The title compound was prepared according to the published protocol[1]. A solution of sery597 (200 mg, 0.38 mmol) and hydrazine hydrate (100 mg, 2.0 mmol) in ethanol (4 ml) was heated under reflux 16 h with stirring and then concentrated under reduced pressure. Ethyl acetate (20 ml) and water (15 ml) were added to the mixture. The organic phase was separated, washed with water (10 ml) and brine (10 nil), dried over Na$_2$SO$_4$ and evaporated under reduced pressure. The crude product was purified by flash chromatography on silica gel (gradient EtOAc/n-hexane=1:5 v/v to EtOAc/n-hexane=1:4 v/v) to provide sery603 (60 mg, 41%) as a white solid.

TLC (hexane:EtOAc, 3/1 v/v): RF=0.36.

$^1$H NMR (400 MHz, DMSO-d$_6$+1% conc. DCI) δ=8.06 (t, J=1.6 Hz, 1H), 7.86 (d, J=7.9 Hz, 1H), 7.59 (d, J=1.7 Hz, 1H), 7.56-7.49 (m, 2H), 7.40 (t, J=7.9 Hz, 1H), 7.20 (s, 1H), 6.78 (d, J=8.5 Hz, 1H), 2.78 (t, J=6.6 Hz, 2H), 1.79 (t, J=6.6 Hz, 2H), 1.29 (s, 6H).

$^{13}$C NMR (100.6 MHz, DMSO-d$_6$+1% conc. DCI) δ=154.0, 147.0, 146.2, 134.2, 131.1, 130.6, 127.8, 126.8, 124.6, 124.2, 122.3, 121.6, 121.4, 117.2, 99.5, 74.6, 32.1, 26.7, 21.9.

LC MS (RP18-100 Å, gradient 0% CH$_3$CN/100% H$_2$O→100% CH$_3$CN in 50 min), RT 44.1 min and mass 383.13 (100%), 385.09 (100%) ([M+H]$^+$).

M.p. 182-183° C.

REFERENCES

1. Wagner, J. et al. AnIe138b: a novel oligomer modulator for disease-modifying therapy of neurodegenerative diseases such as prion and Parkinson's disease. *Acta Neuropathol.* 125, 795-813 (2013).
2. Besselievre, F. et al. Ligandless microwave-assisted Pd/Cu-catalyzed direct arylation of oxazoles. *J. Org. Chem.* 73, 3278-3280 (2008).
3. Yoshizumi, T. et al. Synthesis of 2,5-diaryloxazoles through van Leusen reaction and copper-mediated direct arylation. *Tetrahedron Lett.* 50, 3273-3276 (2009).
4. Lee, J. C. et al. Facile synthesis of oxazoles starting from ketones. *Synth. Commun.* 33, 1611-1614 (2003)
5. Baykov, S. et al. The first one-pot ambient-temperature synthesis of 1,2,4-oxadiazoles from amidoximes and carboxylic acid esters. *Tetrahedron* 73, 945-951 (2017).

Example 6

Effect of DPP Compounds on Morphology and Cell Death of High-Level α-Synuclein-Expressing Human Melanoma Cells To determine the impact of the DPP compounds on high-level α-synuclein-expressing human melanoma cells, WM983-B melanoma cells were plated, in duplicate, in 12-well tissue culture plates in cell culture medium containing 10% fetal bovine serum. Twenty-four hours later, the cells were rinsed three-times with serum-free medium, followed by addition of serum-free medium containing each DPP compound at a dose of 10 μM. Following incubation of the DPP compound-treated cells at 37° C. for 48 hr, each DPP compound was added to the cells at a second 10 μM dose. Using light microscopy, changes in the cells' morphology>detachment of the cells from the cell culture dish/floating in the cell culture medium>cell death were recorded on a scale of 0, +, ++, +++, ++++ at the 24 hr, 48 hr, 72 hr and 96 hr time-point following addition of DPP compound. WM983-B melanoma cells, which had received DMSO only, and WM983-B melanoma cells that received neither DPP compound nor DMSO served as controls. The results are shown in Table 1.

TABLE 1

Test screening of DPP compounds in human metastatic melanoma cells

| Compound | Activity* |
|---|---|
| anle180216 | ++++ |
| sery315b | ++++ |
| sery534 | ++++ |
| sery607 | ++++ |
| anle138b | +++ |
| anle138c | +++ |
| anle180222 | +++ |
| anle253b | +++ |
| sery109 | +++ |
| sery117 | +++ |
| sery140 | +++ |
| sery345 | +++ |
| sery363a | +++ |
| sery540 | +++ |

TABLE 1-continued
Test screening of DPP compounds in human metastatic melanoma cells
| Compound | Activity* |
|---|---|
| 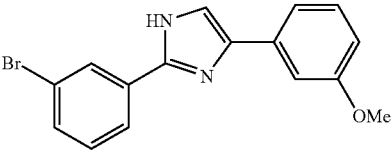 sery547 | +++ |
| 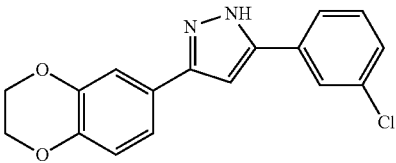 sery599 | +++ |
| 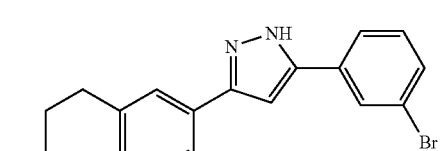 sery603 | +++ |
| 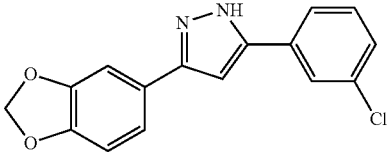 sery335b | +++ |
| 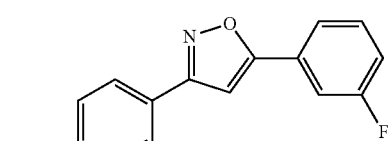 anle461c | ++ |
| 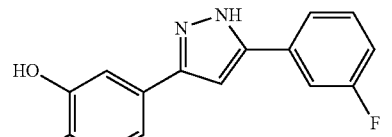 sery85 | ++ |
| 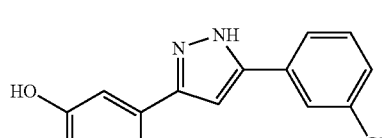 sery320c | ++ |
| 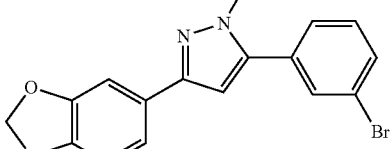 sery392b | ++ |
| 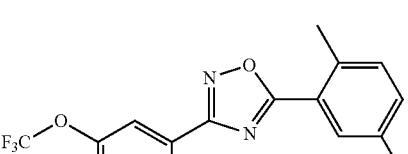 sery542 | ++ |
|  sery428b | ++ |
| 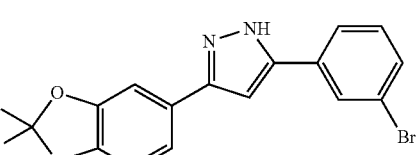 anle270 | + |
| 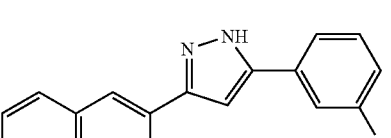 sery292b | + |
| 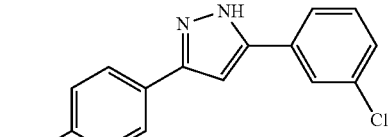 sery383 | + |
| 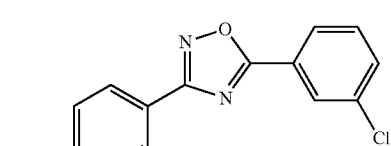 sery562 | + |

TABLE 1-continued

Test screening of DPP compounds in human metastatic melanoma cells

| Compound | Activity* |
|---|---|
| 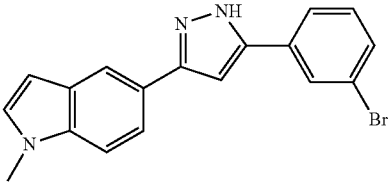 anle253min | + |
| 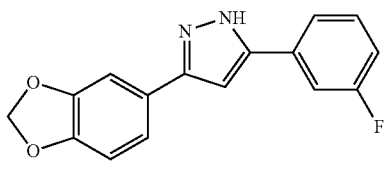 anle186b | − |
| 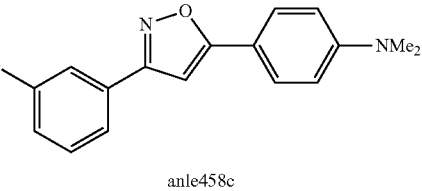 anle458c | − |
| 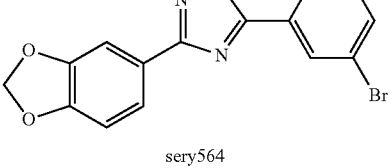 sery564 | − |
| 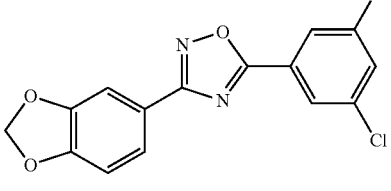 anle171129 | − |

Upon addition of a 10 μM dose of compound to the cells propagated in serum-free culture medium, the read-out activity was recorded as cell death The DPP compounds were added to α-synuclein-expressing WM983-B human metastatic melanoma cells. The activity of the evaluated DPP compounds was:

++++ 100% cell death at 48 h following addition of DPP compound

+++ 100% cell death at 96 h following addition of DPP compound

++ 50-90% cell death at 96 h following addition of DPP compound

+ 20-50% cell death at 96 h following addition of DPP compound

− less than 20% cell death at 96 h following addition of DPP compounds or precipitation of compound in medium

The invention claimed is:

1. A method of treating or preventing melanoma comprising administering to a subject in need thereof a therapeutically effective amount of a compound of formula (E)

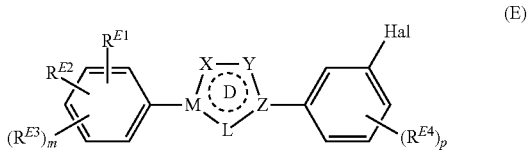

(E)

wherein the ring D containing X, Y, L, M, and Z is selected directionally from the following structures:

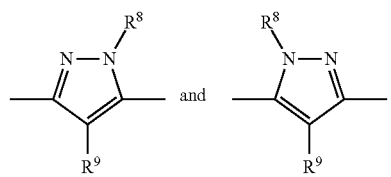

wherein $R^8$ is selected from hydrogen; $C_{1-4}$ alkyl; —$CH_2O$—$P(=O)(OR)(OR)$; —$C_{1-4}$ alkylene-halogen; and $C_{6-10}$ aryl, wherein the aryl ring can be optionally substituted by $C_{1-4}$ alkyl or halogen;

$R^9$ is selected from hydrogen; $C_{1-4}$ alkyl; —$C_{1-4}$ alkylene-halogen; and $C_{6-10}$ aryl, wherein the aryl ring can be optionally substituted by $C_{1-4}$ alkyl or halogen;

Hal is selected from F, Cl, Br, and I;

$R^{E1}$ is selected from hydroxy, $C_{1-6}$ alkoxy, and —$NR^{E5}R^{E6}$;

$R^{E2}$ is selected from hydrogen, halogen, hydroxy, $C_{1-6}$ alkoxy, and —$NR^{E5}R^{E6}$; or if $R^{E1}$ and $R^{E2}$ are attached to adjacent carbon atoms, $R^{E1}$ and $R^{E2}$ together can alternatively non-directionally form a structure -T-$(CR^{E7}R^{E8})_n$—V—, wherein T is selected from $CR^{E9}R^{E10}$, NR* and O and V is selected from $CR^{E9}R^{E10}$, NR* and O, as well as corresponding structures in which a double bond is present;

$R^{E5}$ and $R^{E6}$ are selected independently from hydrogen and $C_{1-6}$ alkyl;

$R^{E7}$ and $R^{E8}$ are independently H or F;

$R^{E9}$ and $R^{E10}$ are independently H or F;

n is 1 to 3;

$R^{E3}$ is a $C_{1-6}$ alkyl group or a $C_{6-10}$ aryl group;

p is 0 to 2;

$R^{E4}$ is a halogen atom, a $C_{1-6}$ alkyl group or a $C_{6-10}$ aryl group;

p is 0 to 1;

R is a hydrogen atom or a cation;

R* is a hydrogen atom or a $C_{1-6}$ alkyl group;

as well as an ether, ester, solvate or salt of the compound represented by formula (E).

2. The method according to claim 1 wherein the compound represented by formula (E) is a compound represented by formula (A) or (B)

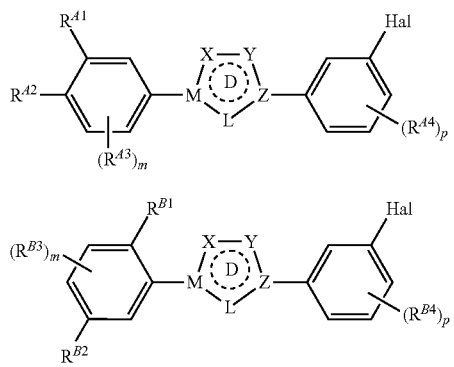

(A)

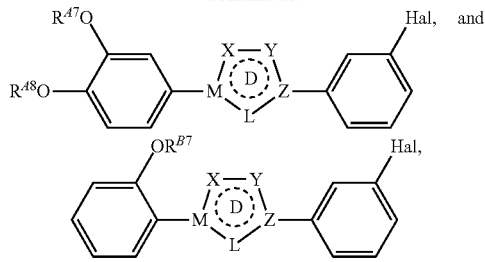

(B)

wherein in formula (A):
$R^{A1}$ and $R^{A2}$ are each selected independently from hydrogen, halogen, hydroxy, $C_{1-6}$ alkoxy, and $-NR^{A5}R^{A6}$; or with the proviso that at least one of $R^{A1}$ and $R^{A2}$ is hydroxy, $C_{1-6}$ alkoxy, or $-NR^{A5}R^{A6}$;
alternatively, $R^{A1}$ and $R^{A2}$ can together non-directionally form a structure $-T-(CR^{E7}R^{E8})_n-V-$;
$R^{A3}$ is a $C_{1-6}$ alkyl group or a $C_{6-10}$ aryl group;
$R^{A4}$ is a halogen atom, a $C_{1-6}$ alkyl group or a $C_{6-10}$ aryl group; and
$R^{A5}$ and $R^{A6}$ are selected independently from hydrogen and $C_{1-6}$ alkyl;
wherein in formula (B):
$R^{B1}$ is selected from hydroxy, $C_{1-6}$ alkoxy, and $-NR^{B5}R^{B6}$;
$R^{B2}$ is selected from hydrogen, halogen, hydroxy, $C_{1-6}$ alkoxy, and $-NR^{B5}R^{B6}$;
$R^{B3}$ is a $C_{1-6}$ alkyl group or a $C_{6-10}$ aryl group;
$R^{B4}$ is a halogen atom, a $C_{1-6}$ alkyl group or a $C_{6-10}$ aryl group; and
$R^{B5}$ and $R^{B6}$ are selected independently from hydrogen and $C_{1-6}$ alkyl;
as well as an ether, ester, solvate or salt of the compound represented by formula (A) or (B).

3. The method according to claim 1,
wherein:
$R^9$ is H;
as well as an ether, ester, solvate or salt of these compounds.

4. The method according to claim 1, wherein the compound is selected from the group consisting of:

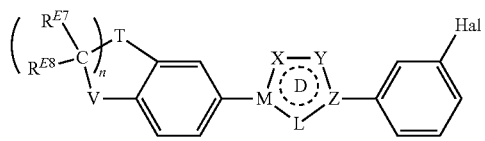

as well as corresponding structures in which a double bond is present in $-T-(CR^{E7}R^{E8})_n-V-$,

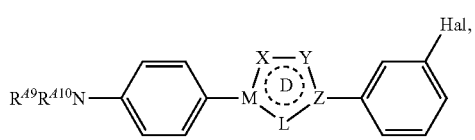

wherein
$R^{A7}$ is H or $C_{1-4}$ alkyl;
$R^{A8}$ is H or $C_{1-4}$ alkyl;
$R^{A9}$ is H or $C_{1-4}$ alkyl;
$R^{A10}$ is H or $C_{1-4}$ alkyl; and
$R^{B7}$ is H or $C_{1-4}$ alkyl;
as well as an ether, ester, solvate or salt of these compounds.

5. The method according to claim 4, wherein the compound is selected from the group consisting of:

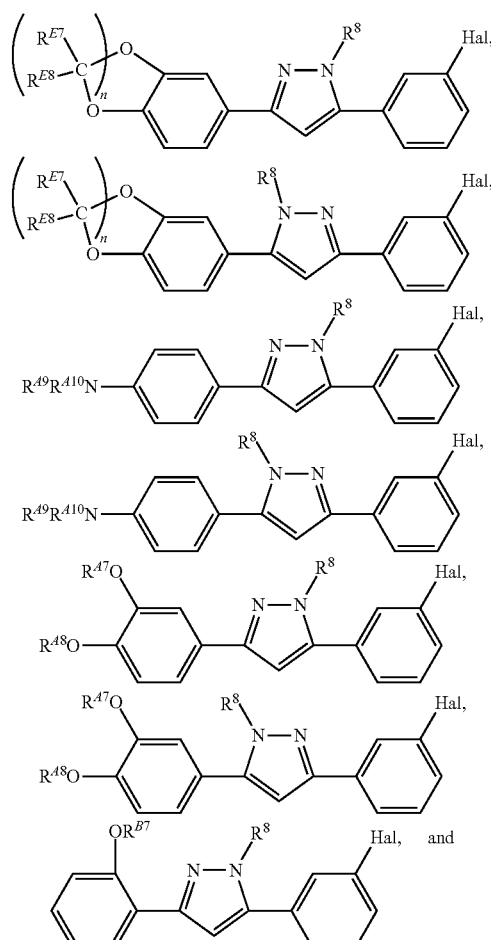

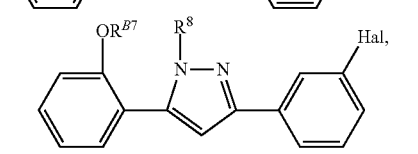

wherein:
$R^8$ is selected from hydrogen; $C_{1-4}$ alkyl; —CH$_2$O—P(=O)(OR)(OR); and —$C_{1-4}$ alkylene-halogen;
Hal is selected from F, Cl, Br, and I;
$R^{E7}$ and $R^{E8}$ are independently H or F;
$R^{A7}$ is H or $C_{1-4}$ alkyl;
$R^{A8}$ is H or $C_{1-4}$ alkyl;
$R^{A9}$ is H or $C_{1-4}$ alkyl;
$R^{A10}$ is H or $C_{1-4}$ alkyl;
$R^{B7}$ is H or $C_{1-4}$ alkyl; and
R is H or a cation;
as well as an ether, ester, solvate or salt of these compounds.

6. The method according to claim 5, wherein the compound is selected from the group consisting of:

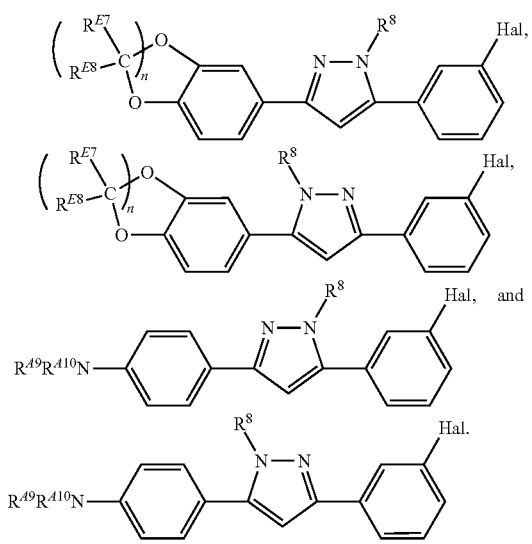

wherein
n is 1 to 3;
$R^{E7}$ and $R^{E8}$ are independently H or F;
$R^{A9}$ is H or $C_{1-4}$ alkyl;
$R^{A10}$ is H or $C_{1-4}$ alkyl;
$R^8$ is selected from hydrogen; $C_{1-4}$ alkyl; —CH$_2$O—P(=O)(OR)(OR); and —$C_{1-4}$ alkylene-halogen;
Hal is selected from F, Cl, Br, and I;
as well as an ether, ester, solvate or salt of these compounds.

7. The method according to claim 1, wherein the ring D is selected from the group consisting of:

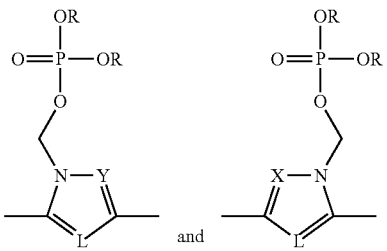

and as well as an ether, ester, solvate or salt of these compounds.

8. The method according to claim 1, wherein
if $R^{E1}$ is —NR$^{E5}$R$^{E6}$ then $R^{E1}$ is attached in para position compared to the carbon atom, which binds the phenyl ring to ring D;
as well as an ether, ester, solvate or salt of these compounds.

9. A method of treating or preventing melanoma comprising administering to a subject in need thereof a therapeutically effective amount of a compound of a formula selected from:

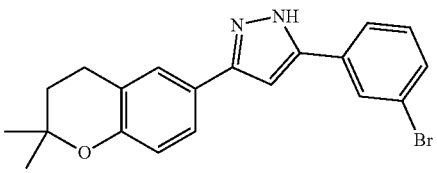 [SMILES: CC1(C)CCc2cc(-c3cc(-c4cccc(Br)c4)[nH]n3)ccc2O1]

* * * * *

UNITED STATES PATENT AND TRADEMARK OFFICE
CERTIFICATE OF CORRECTION

PATENT NO. : 11,180,518 B2  Page 1 of 1
APPLICATION NO. : 16/612717
DATED : November 23, 2021
INVENTOR(S) : Dorothea Becker et al.

It is certified that error appears in the above-identified patent and that said Letters Patent is hereby corrected as shown below:

In the Claims

Claim 1, Column 66, Line 55:
Please delete: "p is 0 to 2;"
Please replace with: "m is 0 to 2;"

Claim 7, Column 70, Lines 10-20:

Please delete: " 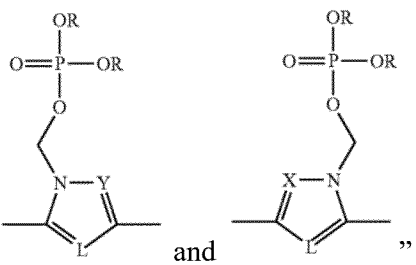 "

Please replace with: " 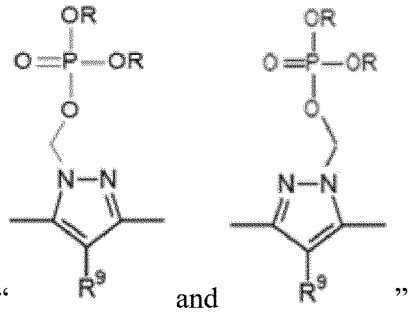 "

Signed and Sealed this
Tenth Day of May, 2022

Katherine Kelly Vidal
*Director of the United States Patent and Trademark Office*